US011046945B2

(12) United States Patent
Stalnecker et al.

(10) Patent No.: US 11,046,945 B2
(45) Date of Patent: Jun. 29, 2021

(54) LABELED GLUTAMINASE PROTEINS, ISOLATED GLUTAMINASE PROTEIN MUTANTS, METHODS OF USE, AND KIT

(71) Applicant: CORNELL UNIVERSITY, Ithaca, NY (US)

(72) Inventors: Clint A. Stalnecker, Ithaca, NY (US); Jon W. Erickson, Freeville, NY (US); Sekar Ramachandran, Ithaca, NY (US); Rick Cerione, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 669 days.

(21) Appl. No.: 14/771,085

(22) PCT Filed: Feb. 27, 2014

(86) PCT No.: PCT/US2014/019073
§ 371 (c)(1),
(2) Date: Aug. 27, 2015

(87) PCT Pub. No.: WO2014/134329
PCT Pub. Date: Sep. 4, 2014

(65) Prior Publication Data

US 2016/0002619 A1 Jan. 7, 2016

Related U.S. Application Data

(60) Provisional application No. 61/770,197, filed on Feb. 27, 2013.

(51) Int. Cl.
*C12N 9/80* (2006.01)
*G01N 33/533* (2006.01)
*G01N 33/58* (2006.01)
*A61K 38/00* (2006.01)

(52) U.S. Cl.
CPC ........ *C12N 9/80* (2013.01); *C12Y 305/01002* (2013.01); *G01N 33/582* (2013.01); *G01N 2333/98* (2013.01); *G01N 2500/04* (2013.01); *G01N 2500/20* (2013.01)

(58) Field of Classification Search
CPC .... G01N 33/582; G01N 33/6809; C12N 9/80; C12Y 305/01002
See application file for complete search history.

(56) References Cited

U.S. PATENT DOCUMENTS 6,183,996 B1 * 2/2001 Stewart .................... C12N 9/93 435/320.1
6,872,537 B1 3/2005 Vale et al.
2004/0258698 A1 * 12/2004 Wightman ............ A61K 47/50 424/178.1
2007/0054278 A1 3/2007 Cargill
2013/0116302 A1 * 5/2013 Kumar Gurumurthy .................... C12N 15/1137 514/44 A
2014/0186325 A1 * 7/2014 Haigis ................ A61K 31/7088 424/94.5

OTHER PUBLICATIONS

Hartwick et al. (2012) BPTES inhibition of hGA124-551, a truncated form of human kidney-type glutaminase, J Enz. Inh. Medic. Chem., vol. 27, No. 6, p. 861-867.*
Tian et al. (2012) Mitochondrial Glutaminase Release Contributes to Glutamate-Mediated Neurotoxicity during Human Immunodeficiency Virus-1 Infection, J. Neuroimmune. Pharmacol., vol. 7, No. 3, pp. 619-628.*
Holcomb et al. (2000) Isolation, characterization and expression of a human brain mitochondrial glutaminase cDNA, Mol. Braimn Res., vol. 76, pp. 56-63.*
Al-Khodor et al., "Functional Diversity of Ankyrin Repeats in Microbial Proteins," Trends Microbiol. 18(3):132-139 (2009).
Bera et al., "Interdomain Signaling in Glutamine Phosphoribosylpyrophosphate Amidotransferase," J. Biol. Chem. 274 (51):36498-36504 (1999).
Kim et al., "Glutaminase Kidney Isoform, Mitochondrial Isoform 1 Precursor [*Homo sapiens*]," NCBI Reference Sequence NP_055720.3 (downloaded Jul. 18, 2014).
Robinson et al., "Novel Mechanism of Inhibition of Rat Kidney-Type Glutaminase by Bis-2-(5-phenylacetamido-1,2,4-thiadiazol-2-yl)Ethyl Sulfide (BPTES)," Biochem. J. 406:407-414 (2007).
"NHS-Fluroescein," Thermo Scientific, 46409/46410(2082.1): 4 pages (2011).
International Search Report and Written Opinion corresponding to PCT/US2014/019073 dated Aug. 12, 2014.
Stalnecker et al., Poster, "Development of a Real Time FRET Assay to Study Glutaminase Activation and Inhibition by Small Molecules That Target Glutamine Metabolism" (presented Feb. 27, 2013).
PCT/US2014/019073, International Preliminary Report on Patentability (dated Sep. 1, 2015).
Stalnecker et al., "Mechanism by Which a Recently Discovered Allosteric Inhibitor Blocks Glutamine Metabolism in Transformed Cells," PNAS 112(2):394-99 (2015).

* cited by examiner

*Primary Examiner* — Scarlett Y Goon
*Assistant Examiner* — Samuel W Liu
(74) *Attorney, Agent, or Firm* — Troutman Pepper Hamilton Sanders LLP (Rochester)

(57) ABSTRACT

The present invention relates to a labeled glutaminase (GLS) protein comprising a GLS protein and a fluorescent reporter group attached to the GLS protein, wherein the fluorescent reporter group is attached to the GLS protein within the glutaminase domain pfam04960 of GLS. The present invention also relates to isolated glutaminase protein mutants. Also disclosed is a method of screening for compounds that allosterically bind to a glutaminase protein. The present invention also relates to a method of identifying compounds that inhibit or stabilize tetramer formation of glutaminase protein. The present invention further relates to a screening kit for compounds that inhibit or stabilize tetramer formation.

1 Claim, 18 Drawing Sheets

Specification includes a Sequence Listing.

Glutaminase [Mus musculus] kidney isoform 2: NP_001106854.1
Matched peptides underscored
Anti-GAC antibody recognition sequence in bold

```
  1 mmrlrgsaml relllrppaa vgavlrraqp lgtlcrrprg gsrptaglva aarlhpwwgg
 61 ggrakgpgag glssspseil qelgkggtpp qqqqqqqqqp gasppaapgp kdspgetdaf
121 gnsegkemva agdnkikqgl lpsledllfy tiaegqekip vhkfitalks tglrtsdprl
181 kecmdmlrlt lqttsdgvml dkdlfkkcvq snivlltqaf rrkfvipdfm sftshidely
241 esakkqsggk vadyipqlak fspdlwgvsv ctvdgqrhsi gdtkvpfclq scvkplkyai
301 avndlgteyv hryvgkepsg lrfnklflne ddkphnpmvn agaivvtsli kqgvnnaekf
361 dyvmqflnkm agneyvgfsn atfqseresg drnfaigyyl kekkcfpegt dmvgildfyf
421 qlcsievtce sasvmaatla nggfcpitge rvlspeavrn tlslmhscgm ydfsgqfafh
481 vglpaksgva ggillvvpnv mgmmcwsppl dkmgnsvkgi hfchdlvslc nfhnydnlrh
541 fakkldprre ggdqrhsfgp ldyeslqqel alkdtvwkkv spessddtst tvvyrmeslg
```

*FIG. 8C*

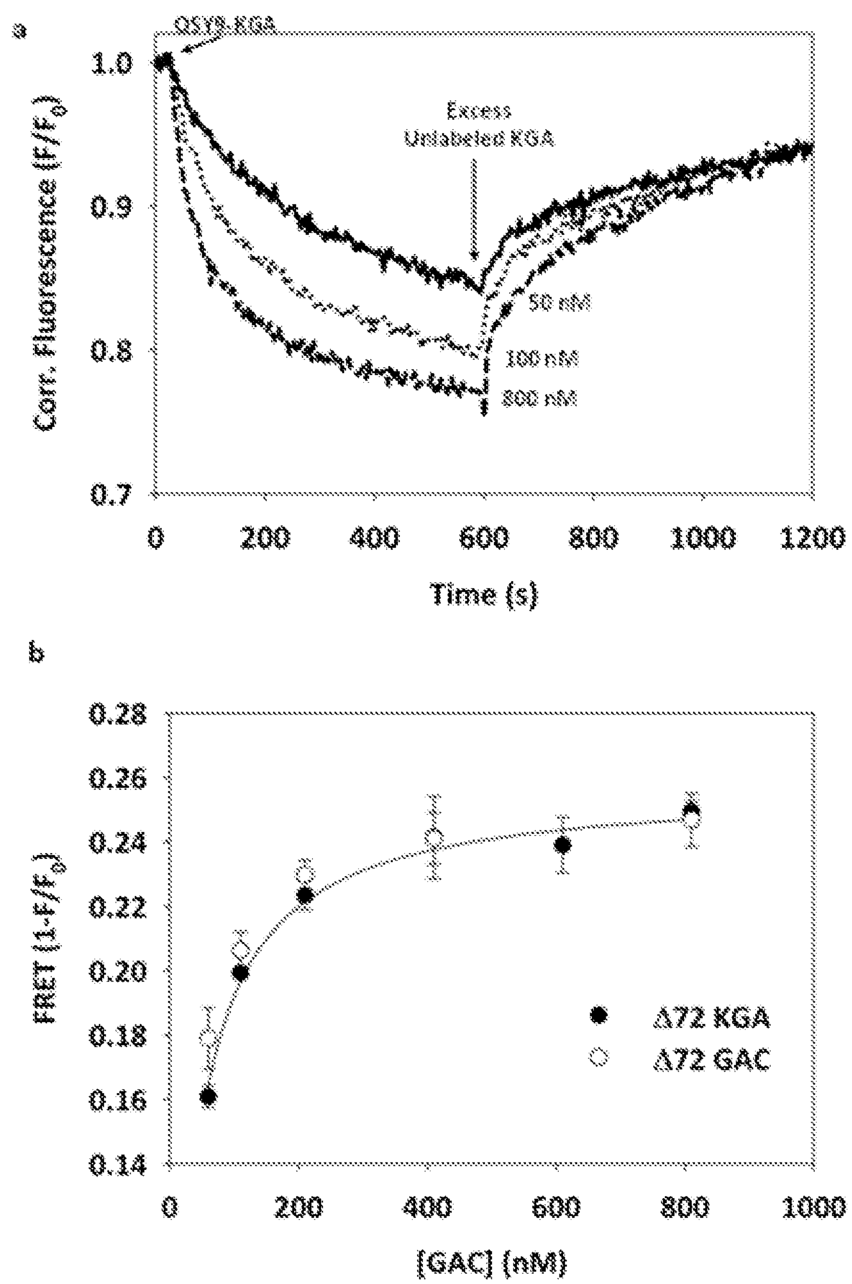
*FIGS. 9A-B*

*FIG. 11*

```
Mus musculus KGA   MMRLRGSGMLRDLLLRSPAGVSATLRRAQPLVTLCRRPRGGGRPAAGPAAAARLHPWWGG 60
Homo sapiens KGA   MMRLRGSAMLRELLLRPPAAVGAVLRRAQPLGTLCRRPRGGSRPTAGLVAAARLHPWWGG 60
Mus musculus GAC   MMRLRGSGMLRDLLLRSPAGVSATLRRAQPLVTLCRRPRGGGRPAAGPAAAARLHPWWGG 60
Homo sapiens GAC   MMRLRGSAMLRELLLRPPAAVGAVLRRAQPLGTLCRRPRGGSRPTAGLVAAARLHPWWGG 60
                   *******.***:****.**.*.*.******* *********.**:** .***********

Mus musculus KGA GGWPAEPLARGLSSSPSEILQELGKGSTHPQ--------PGVSPPAAPAAPGPKDGPGET 112
Homo sapiens KGA GGRAKGPGAGGLSSSPSEILQELGKGGTPPQQQQQQQQQPGASP---PAAPGPKDSPGET 117
Mus musculus GAC GGWPAEPLARGLSSSPSEILQELGKGSTHPQ--------PGVSPPAAPAAPGPKDGPGET 112
Homo sapiens GAC GGRAKGPGAGGLSSSPSEILQELGKGGTPPQQQQQQQQQPGASP---PAAPGPKDSPGET 117
                 ** .  * * ****************.* **        **.**   ********.****

Mus musculus KGA DAFGNSEGKELVASGENKIKQGLLPSLEDLLFYTIAEGQEKIPVHKFITALKSTGLRTSD 172
Homo sapiens KGA DAFGNSEGKEMVAAGDNKIKQGLLPSLEDLLFYTIAEGQEKIPVHKFITALKSTGLRTSD 177
Mus musculus GAC DAFGNSEGKELVASGENKIKQGLLPSLEDLLFYTIAEGQEKIPVHKFITALKSTGLRTSD 172
Homo sapiens GAC DAFGNSEGKEMVAAGDNKIKQGLLPSLEDLLFYTIAEGQEKIPVHKFITALKSTGLRTSD 177
                 **********:**:*:********************************************

Mus musculus KGA PRLKECMDMLRLTLQTTSDGVMLDKDLFKKCVQSNIVLLTQAFRRKFVIPDFMSFTSHID 232
Homo sapiens KGA PRLKECMDMLRLTLQTTSDGVMLDKDLFKKCVQSNIVLLTQAFRRKFVIPDFMSFTSHID 237
Mus musculus GAC PRLKECMDMLRLTLQTTSDGVMLDKDLFKKCVQSNIVLLTQAFRRKFVIPDFMSFTSHID 232
Homo sapiens GAC PRLKECMDMLRLTLQTTSDGVMLDKDLFKKCVQSNIVLLTQAFRRKFVIPDFMSFTSHID 237
                 ************************************************************

Mus musculus KGA ELYESAKKQSGGKVADYIPQLAKFSPDLWGVSVCTVDGQRHSTGDTKVPFCLQSCVKPLK 292
Homo sapiens KGA ELYESAKKQSGGKVADYIPQLAKFSPDLWGVSVCTVDGQRHSIGDTKVPFCLQSCVKPLK 297
Mus musculus GAC ELYESAKKQSGGKVADYIPQLAKFSPDLWGVSVCTVDGQRHSTGDTKVPFCLQSCVKPLK 292
Homo sapiens GAC ELYESAKKQSGGKVADYIPQLAKFSPDLWGVSVCTVDGQRHSIGDTKVPFCLQSCVKPLK 297
                 ****************************************** *****************

Mus musculus KGA YAIAVNDLGTEYVHRYVGEEPSGLRFNKLFLNEDDKPHNPMVNAGAIVVTSLIKQGVNNA 352
Homo sapiens KGA YAIAVNDLGTEYVHRYVGEEPSGLRFNKLFLNEDDKPHNPMVNAGAIVVTSLIKQGVNNA 357
Mus musculus GAC YAIAVNDLGTEYVHRYVGEEPSGLRFNKLFLNEDDKPHNPMVNAGAIVVTSLIKQGVNNA 352
Homo sapiens GAC YAIAVNDLGTEYVHRYVGEEPSGLRFNKLFLNEDDKPHNPMVNAGAIVVTSLIKQGVNNA 357
                 ************************************************************

Mus musculus KGA EKFDYVMQFLNKMAGNEYVGFSNATFQSERESGKRNFAIGYYLKEKKCFPEGTDMVGILD 412
Homo sapiens KGA EKFDYVMQFLNKMAGNEYVGFSNATFQSERESGKRNFAIGYYLKEKKCFPEGTDMVGILD 417
Mus musculus GAC EKFDYVMQFLNKMAGNEYVGFSNATFQSERESGKRNFAIGYYLKEKKCFPEGTDMVGILD 412
Homo sapiens GAC EKFDYVMQFLNKMAGNEYVGFSNATFQSERESGKRNFAIGYYLKEKKCFPEGTDMVGILD 417
                 ************************************************************

Mus musculus KGA FYFQLCSIEVTCESASVMAATLANGGFCPITGERVLSPEAVENTLSLMHSCGMYDFSGQF 472
Homo sapiens KGA FYFQLCSIEVTCESASVMAATLANGGFCPITGERVLSPEAVENTLSLMHSCGMYDFSGQF 477
Mus musculus GAC FYFQLCSIEVTCESASVMAATLANGGFCPITGERVLSPEAVENTLSLMHSCGMYDFSGQF 472
Homo sapiens GAC FYFQLCSIEVTCESASVMAATLANGGFCPITGERVLSPEAVENTLSLMHSCGMYDFSGQF 477
                 ************************************************************

Mus musculus KGA AFHVGLPAKSGVAGGILLVVPNVMGMMCWSPPLDKMGNSVKGIHFCHDLVSLCNFHNYDN 532
Homo sapiens KGA AFHVGLPAKSGVAGGILLVVPNVMGMMCWSPPLDKMGNSVKGIHFCHDLVSLCNFHNYDN 537
Mus musculus GAC AFHVGLPAKSGVAGGILLVVPNVMGMMCWSPPLDKMGNSVKGIHFCHDLVSLCNFHNYDN 532
Homo sapiens GAC AFHVGLPAKSGVAGGILLVVPNVMGMMCWSPPLDKMGNSVKGIHFCHDLVSLCNFHNYDN 537
                 ************************************************************

Mus musculus KGA LRHFAKKLDPRREGGDQRVKSVINLLFAAYTGDVSALRRFALSAMDMEQRDYDSRTALHV 592
Homo sapiens KGA LRHFAKKLDPRREGGDQRVKSVINLLFAAYTGDVSALRRFALSAMDMEQRDYDSRTALHV 597
Mus musculus GAC LRHFAKKLDPRREGGDQ---------------------RHSFGPLDYES--LQQELALKE 569
Homo sapiens GAC LRHFAKKLDPRREGGDQ---------------------RHSFGPLDYES--LQQELALKD 574
                 *****************                     *.::..:* *.   :.. **:

Mus musculus KGA AAAEGHVEVVKFLLEACKVNPFPKDRWNNTPMDEALHFGHHDVFKILQEYQVQYTPQGDS 652
Homo sapiens KGA AAAEGHVEVVKFLLEACKVNPFPKDRWNNTPMDEALHFGHHDVFKILQEYQVQYTPQGDS 657
Mus musculus GAC TVWK-------------KVSPESNEDISTTVVYRMESLGEKS------------------ 598
Homo sapiens GAC TVWK-------------KVSPESSDDTSTTVVYRMESLGERS------------------ 603
                           :. :             **.* ..:  ..* : .   :*.:.

Mus musculus KGA DNGKENQTVHKNLDGLL 669
Homo sapiens KGA DDGKGNQTVHKNLDGLL 674
Mus musculus GAC -----------------
Homo sapiens GAC -----------------
```

LABELED GLUTAMINASE PROTEINS, ISOLATED GLUTAMINASE PROTEIN MUTANTS, METHODS OF USE, AND KIT

This application is a national stage application under 35 U.S.C. § 371 of PCT Application No. PCT/US2014/019073, filed Feb. 27, 2014, which claims the priority benefit of U.S. Provisional Patent Application Ser. No. 61/770,197, filed Feb. 27, 2013, which is hereby incorporated by reference in its entirety.

FIELD OF THE INVENTION

The present invention relates to labeled glutaminase proteins, isolated glutaminase protein mutants, methods of screening for compounds that allosterically bind to glutaminase proteins, methods of identifying compounds that inhibit or stabilize tetramer formation of glutaminase proteins, and screening kits for compounds that inhibit or stabilize tetramer formation of glutaminase.

BACKGROUND OF THE INVENTION

Recently, the role of the mitochondrial enzyme glutaminase ("GLS") has gained significant attention as a therapeutic target for cancer (DeBerardinis et al., "Q's Next: The Diverse Functions of Glutamine in Metabolism, Cell Biology and Cancer," *Oncogene* 29:313-324 (2010)). GLS catalyzes the hydrolysis of glutamine to glutamate, which is then used in the TCA cycle of cancer cells undergoing an aberrant glycolytic flux (i.e., the "Warburg effect") as a non-glucose derived source for anaplerosis. The elevation in glutamine metabolism exhibited by cancer cells ("glutamine addiction") is thought to be critical for sustaining their proliferative capacity as well as for other aspects of their transformed phenotypes (Wise et al., "Glutamine Addiction: A New Therapeutic Target in Cancer," *Trends Biochem. Sci.* 35(8): 427-433 (2010); Vander Heiden et al., "Understanding the Warburg Effect: The Metabolic Requirements of Cell Proliferation," Science 324:1029-1033 (2009); Wang et al., "Targeting Mitochondrial Glutaminase Activity Inhibits Oncogenic Transformation," *Cancer Cell* 18:207-219 (2010); Gao et al., "c-Myc Suppression of miR-23a/b Enhances Mitochondrial Glutaminase Expression and Glutamine Metabolism," *Nature* 458:762-76r (2009); Ward et al., "Metabolic Reprogramming: A Cancer Hallmark Even Warburg Did Not Anticipate," *Cancer Cell* 21:297-309 (2012)). Work from the inventors' laboratory has shown that a specific GLS splice variant, called GAC, plays an essential role in the transformation of fibroblasts by oncogenic Dbl (for Diffuse B Cell lymphoma), a guanine nucleotide exchange factor (GEF) that activates the small GTPases Cdc42, Rac, and Rho (Wang et al., "Targeting Mitochondrial Glutaminase Activity Inhibits Oncogenic Transformation," *Cancer Cell* 18:207-219 (2010); Lin et al., "Specific Contributions of the Small GTPases Rho, Rac, and cdc42 to Dbl Transformation," *J. Biol. Chem.* 274:23633-23641 (1999)). Likewise, it has been found that the growth of fibroblasts transformed by oncogenic Rho GTPase mutants, as well as the proliferative and invasive activities of a variety of cancer cells, are dependent upon GAC activity (Katt et al., "Dibenzophenanthridinones as Inhibitors of Glutaminase C and Cancer Cell Proliferation," *Mol. Cancer Ther.* 11:1269-1278 (2012)). Thus, given the importance of GAC expression and activation for oncogenic transformation, the identification of small molecule inhibitors that target this metabolic enzyme offers new opportunities for the development of anti-cancer drugs.

A commonly used active site-directed inhibitor of members of the glutaminase family is DON (for Diazo-O-norleucine), a glutamine derivative that forms a stable acyl-enzyme intermediate with the catalytic serine residue responsible for deamidase activity. Because DON reacts with the highly conserved glutaminase active site which is present in all members of the β-lactamase superfamily (Thangavelu et al., "Structural Basis for the Active Site Inhibition Mechanism of Human Kidney-Type Glutaminase (KGA)," *Scientific Reports* 4:3827 (1-7) (2014); Shelton et al., "Glutamine Targeting Inhibits Systemic Metastasis in the VM-M3 Murine Tumor Model," *Int. J. Cancer* 127(10): 2478-2485 (2010)), it has been shown to have severe off-target effects and, therefore, does not represent an ideal candidate for selectively inhibiting the elevated glutamine metabolism characteristic of cancer cells (Rahman et al., "Phase I Study and Clinical Pharmacology of 6-diazo-5-oxo-L-norleucine (DON)," *Investigational New Drugs* 3:369-374 (1985)). However, two classes of allosteric inhibitors of GAC have been identified which offer more promising options as lead compounds for the development of cancer therapeutics. One of these is BPTES (bis-2-(5-phenylacetamido-1,2,4-thiadiazol-2-yl)ethyl sulfide), a reversible inhibitor of GAC which has been extensively characterized both biochemically and through steady state kinetic analyses. High-resolution x-ray structures of the GAC-BPTES complex show that BPTES effectively traps GAC as an inactive tetramer (DeLaBarre et al., "Full-Length Human Glutaminase in Complex with an Allosteric Inhibitor," *Biochemistry* 50:10764-10770 (2011); Thangavelu et al., "Structural Basis for the Allosteric Inhibitory Mechanism of Human Kidney-Type Glutaminase (KGA) and its Regulation by Raf-Mek-Erk Signaling in Cancer Cell Metabolism," *Proc. Natl. Acad. Sci.* 109(20):7705-7710 (2012); Cassago et al., "Mitochondrial Localization and Structure-Based Phosphate Activation Mechanism of Glutaminase C with Implications for Cancer Metabolism," *Proc. Natl. Acad. Sci.* 109(4):1092-1097 (2012)).

A more recently identified class of allosteric inhibitors of GAC which offer the advantage of being highly specific in their ability to inhibit the growth and invasive activity of cancer cells, while having little effect on normal (non-transformed) cells, is represented by the benzophenanthridinone, designated as 968 (Wang et al., "Targeting Mitochondrial Glutaminase Activity Inhibits Oncogenic Transformation," *Cancer Cell* 18:207-219 (2010); Katt et al., "Dibenzophenanthridinones as Inhibitors of Glutaminase C and Cancer Cell Proliferation," *Mol. Cancer Ther.* 11:1269-1278 (2012)). The specificity exhibited by 968 for inhibiting the transformed features of cancer cells holds exciting promise for selectively attacking those metabolic changes critical for malignant transformation. However, thus far very little is known regarding how 968 binds to GAC and the mechanisms by which it blocks GAC activation.

The present invention is directed to overcoming these and other deficiencies in the art.

SUMMARY OF THE INVENTION

One aspect of the present invention relates to a labeled glutaminase (GLS) protein comprising a GLS protein and a fluorescent reporter group attached to the GLS protein, where the fluorescent reporter group is attached to the GLS protein within the glutaminase domain pfam04960 of GLS.

Another aspect of the present invention relates to an isolated glutaminase (GLS) protein or protein fragment comprising a mutated glutaminase domain pfam04960 of SEQ ID NO:19.

A further aspect of the present invention relates to a method of screening for compounds that allosterically bind to a glutaminase (GLS) protein. This method involves providing the labeled GLS protein of the present invention under conditions effective for the fluorescent reporter group attached to the GLS protein to produce fluorescence at a first level. The labeled GLS protein is contacted with one or more candidate compounds. Candidate compounds where said contacting causes the fluorescent reporter group to emit fluorescence at a level above or below the first level are identified as being compounds capable of allosteric binding to the GLS protein.

Yet another aspect of the present invention relates to a method of identifying compounds that inhibit or stabilize tetramer formation of glutaminase (GLS) protein. This method involves providing a first labeled GLS dimer protein comprising a GLS protein and a fluorescent donor attached to the GLS dimer protein. A second labeled GLS dimer protein comprising a GLS protein and a fluorescent acceptor attached to the GLS protein is also provided, where binding of the first labeled GLS protein and the second labeled GLS protein forms a GLS protein tetramer and results in an interaction between the fluorescent donor and the fluorescent acceptor which produces a fluorescence resonance energy transfer at a first level. The first labeled GLS dimer protein and the second labeled GLS dimer protein are contacted under conditions effective for the first labeled GLS dimer protein and the second labeled GLS dimer protein to bind and form a GLS protein tetramer. The GLS protein tetramer is contacted with a candidate compound. The method further involves detecting whether said contacting with the candidate compound alters the fluorescence resonance energy transfer at the first level. Detection of the fluorescence resonance energy transfer at the first level indicates that the candidate compound neither inhibits nor stabilizes GLS protein tetramer formation and detection of the fluorescence resonance energy transfer at a level above or below the first level indicates that the candidate compound inhibits or stabilizes tetramer formation of GLS protein.

Yet a further aspect of the present invention relates to a screening kit for compounds that inhibit or stabilize tetramer formation. The kit includes a first labeled GLS dimer protein comprising a GLS protein and a fluorescent donor attached to the GLS dimer protein. Also included in the kit is a second labeled GLS dimer protein comprising a GLS protein and a fluorescent acceptor attached to the GLS protein. Binding of the first labeled GLS protein and the second labeled GLS protein forms a GLS protein tetramer and results in an interaction between the fluorescent donor and the fluorescent acceptor which produces a fluorescence resonance energy transfer.

In the present invention, the binding of 968 to a mutant form of a GLS protein splice variant that is trapped in the monomeric state is characterized, and it is shown that this binding correlates with inhibition of recombinant GLS in a real-time coupled binding and activity assay. Novel fluorescence read-outs are used that, for the first time, allow definitive demonstration that 968 and related compounds directly bind to GLS. Moreover, it is shown that the binding of 968 to the GLS splice variant correlates well with its inhibition of the protein's activity, and importantly, with its ability to block the growth of transformed cells. These findings permit the development of an important new class of cancer therapeutics.

BRIEF DESCRIPTION OF THE DRAWINGS

FIG. 1A is a schematic model of a FRET assay developed to detect dynamic tetramer formation. FIG. 1B illustrates the kinetics of labeling wild type ("WT") GAC with ALEXA FLUOR® 488 succinimidyl ester analyzed by SDS-PAGE and visualized under UV illumination. 488-labeled GAC was analyzed using analytical gel filtration to illustrate the purification of a covalently modified GAC along with eluting at the same volume as an equivalent concentration of unlabeled WT-GAC. FIG. 1C shows that 25 nM 488-WT-GAC fluorescence is quenched upon addition of QSY® 9-WT-GAC (acceptor) in a dose dependent manner (quantified in FIG. 1D), and can be rescued by addition of a 10-fold excess unlabeled WT-GAC. In FIG. 1D, FRET values from FIG. 1C (left axis) were overlaid with concentration dependent activation (in absence of $P_i$) of WT-GAC (right axis) in the presence of 20 mM glutamine measured in an independent two-step activity assay. As illustrated in FIG. 1E, QSY® 9-GAC-488-GAC tetramers were equilibrated by adding 100 nM QSY® 9-WT-GAC to 25 nM 488-WT-GAC, and the effects of phosphate addition on FRET was followed by addition of various phosphate concentrations at 630 seconds. In FIG. 1F, FRET values that resulted from injection of phosphate from FIG. 1E (left axis) were overlaid with phosphate activation of 50 nM WT-GAC in the presence of 20 mM glutamine (right axis) measured in an independent two-step activity assay.

FIG. 2A is the crystal structure of the tetramer form of GAC (PDB 3SS3), highlighting critical contacts for monomer-monomer contact (top) and dimer-dimer contact (bottom). Interfaces are presented as B-factor representations and not cartoons to facilitate visualization of the interactions. FIG. 2B is an overlay of Superdex200 preparative chromatograms of purified mutants.

FIG. 3A is a graph of analytical gel filtration profiles of WT GAC from a 250 μL injection of either 5 mg/mL or 0.5 mg/mL samples in the presence or absence of 50 mM $K_2HPO_4$ in the gel filtration buffer showing a strong correlation of oligomeric state with GAC concentration and inorganic phosphate, whereas the same conditions of the D391K-GAC (FIG. 3B) or K316E-D391K-R459E-GAC (FIG. 3C) does not affect oligomerization. Notably, D391K-GAC (FIG. 3B) was found to have two populations when 0.5 mg/mL samples were injected but not 5 mg/mL, characteristic of a monomer and dimer population that is concentration dependent.

In FIG. 4E, 200 nM of QSY® 9-WT-GAC, QSY® 9-D391K-GAC, or QSY® 9-K316E-D391K-R459E was added to 20 nM of 488-WT-GAC. In FIG. 4F, WT GAC and GAC mutants were titrated and added to an assay of 20 mM glutamine in the absence of phosphate to show no concentration dependent activation was observed of purified GAC mutants.

FIG. 5A is a graph showing that addition of 10 μM BPTES to an equilibrated sample of 20 nM 488-GAC and 200 nM QSY® 9-GAC induces tetramer formation that is not reversible by addition of a 10-fold excess of unlabeled GAC, whereas addition of 25 μM of 968 induces a marked quench in 488-GAC fluorescence with partial recovery by the addition of a 10-fold excess of unlabeled GAC. In FIG. 5B, fluorescence quenching upon addition of 968 to 10 nM 488-GAC in the absence of QSY® 9-GAC shows a concentration dependent quenching interaction. FIG. 5C is an overlay of 968 inhibition of 10 nM WT-GAC activity and 968 quenching of 10 nM 488-GAC fluorescence.

FIG. 6A is a schematic model of a real time drug binding assay coupled to a real-time activity assay. Binding is first monitored by observing 488-GAC fluorescence, followed by observation of NADH fluorescence that is produced upon the addition of the substrate for GAC, glutamine, and the activator inorganic phosphate, in the presence of 10 Units/mL glutamate dehydrogenase (GDH) and 2 mM $NAD^+$. In the graph of FIG. 6B, 10 nM 488-GAC (520 nm emission) was monitored upon addition of 968, BPTES, or DMSO at 30 seconds, and NADH fluorescence (460 nm emission) was monitored following the addition of 20 mM glutamine and 50 mM phosphate at 120 seconds. FIGS. 6C-D illustrate the results of a coupled real time binding and activity assay of 10 nM 488-GAC and 10 nM WT-GAC using 968 and a less potent 968-analogue, WPK968. FIGS. 6E-F illustrate the results of a coupled real time binding and activity assay of 10 nM 488-GAC with 968-analogues 031 and 742, previously reported as GAC inhibitors.

FIG. 7A is a plot illustrating 488 fluorescence quenching of 20 nM 488-labeled WT GAC, dimer, and monomer GAC mutants upon 968 titration. FIG. 7B shows in vitro inhibition curves of 50 nM (closed circles) and 5 nM WT-GAC (open circles) with increasing concentrations of pre-incubated 968, where primary GAC species at each concentration is a dimer/tetramer or monomer/dimer, respectively. Overlaid is the dose dependent 968 inhibition of the ability of Dbl-transformed MEFs to form foci (triangles), adapted from Wang et at, "Targeting Mitochondrial Glutaminase Activity Inhibits Oncogenic Transformation," Cancer Cell 18:207-219 (2010), which is hereby incorporated by reference in its entirety. "[968] (μM)" in FIGS. 7A and 7B refers to the concentration (in μM) of inhibitory compound 968.

FIGS. 8A-C illustrate the identification of a small molecule probe labeling site. In FIG. 8A, 0.6 mg/mL 488 labeled KGA and GAC samples were incubated with 25 μg/mL porcine trypsin (Sigma) on ice for 15 minutes or 60 minutes, at which point Soy Bean Trypsin Inhibitor (SBTI, Sigma) was added to make 20 μg/mL. Loading buffer was added and samples were heated at 95° C. for 2 min and ran on a precast 4-12% Tris-Glycine gel (Invitrogen) for SDS PAGE. The gel was visualized under UV illumination and then transferred to a PVDF membrane to be developed following Western immunoblot with rabbit HRP conjugated anti-GAC antibody raised against the C-terminal GAC peptide (SEQ ID NO:3) highlighted in FIG. 8C. The anti-GAC antibody recognition sequence (SEQ ID NO:13) is set forth in bold in FIG. 8C. (SEQ ID NO: 3 is the full sequence set forth in FIG. 8C, SEQ ID NO: 13 is residues 531-550 of the sequence set forth in FIG. 8C.) In FIG. 8B, the same protocol was followed as in FIG. 8A, where 2.85 mg/mL 488 labeled GAC was incubated with 16.7 μg/mL porcine trypsin on ice for 15 minutes (left of standards) or 30 minutes (right of standards) after which 50 μg/mL SBTI was added. Samples were separated on a 4-12% Tris-Glycine gel following SDS PAGE, and samples for sequencing were cut from adjacent lanes before transfer to a PVDF membrane under UV illumination to identify the peptide fragment of approximately 25 kD. Samples were submitted to Cornell University Mass Spectrometry Core facility, and the resulting identified peptides are underlined in FIG. 8C, resulting in identification of site of modification to be within the glutaminase domain.

FIGS. 9A-B illustrate that the alternate splice variant KGA behaves like GAC in a FRET assay. In FIG. 9A, 10 nM 488-KGA was equilibrated in 50 mM Tris-Acetate (pH=8.5) 0.1 mM EDTA at 20° C. for 2 minutes before adding 40 μL of the appropriate concentration of QSY® 9-KGA and allowed to equilibrate for 5 minutes while monitoring 488-KGA fluorescence. After 5 minutes, the appropriate volume of 33.25 μM (for concentrations up to 200 nM labeled protein) or 69.5 μM (for concentrations above 200 nM labeled protein) unlabeled WT-KGA was added to make the final concentration of unlabeled KGA to be ten-times the concentration of labeled KGA. The FRET values at 5 minutes were quantified and displayed in FIG. 9B versus total labeled protein concentration and combined with FRET measurements from 488-GAC and QSY® 9-GAC titration.

In FIG. 10A, 5 nM 488-D391K-GAC was equilibrated in 50 mM Tris-Acetate (pH=8.5) 0.1 mM EDTA at 20° C. for 2 minutes before the experiment was started. An appropriate volume of 4.4 μM QSY® 9-D391K-GAC was added to 5 nM 488-D391K-GAC and 520 nm emission was monitored for 10 minutes. In FIG. 10B, FRET values from FIG. 10A were plotted in a sigma plot and fit to non-linear regression simple ligand binding equation (line).

FIG. 11 is a sequence alignment of four mutated GLS proteins according to one aspect of the present invention, including mouse GAC (SEQ ID NO:12), human GAC (SEQ ID NO:11), mouse KGA (SEQ ID NO:10), and human KGA (SEQ ID NO:9).

DETAILED DESCRIPTION OF THE INVENTION

Figure 1A:
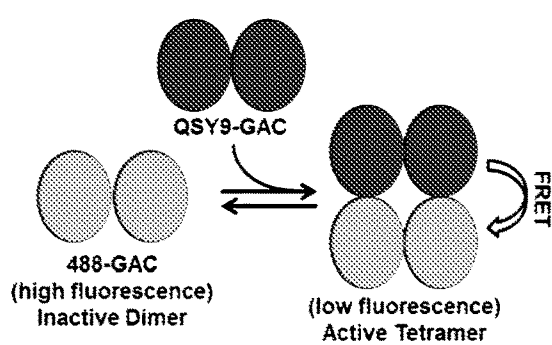
FIGS. 1A-F illustrate the development of a fluorescence assay to monitor subunit interactions.

The present invention relates to labeled glutaminase proteins and isolated glutaminase protein mutants. In addition, the present invention relates to methods of using these proteins in a method for screening for compounds that allosterically bind to a glutaminase protein and a method of identifying compounds that inhibit or stabilize tetramer formation of a glutaminase protein. The present invention further relates to a screening kit for compounds that inhibit or stabilize tetramer formation.

According to a first aspect, the present invention relates to a labeled glutaminase (GLS) protein comprising a GLS protein and a fluorescent reporter group attached to the GLS protein, where the fluorescent reporter group is attached to the GLS protein within the glutaminase domain pfam04960 of GLS.

According to this aspect of the present invention, glutaminase proteins include wild type proteins, including, for example, GLS isoforms GAC and KGA from human and mouse. The GLS isoforms GAC and KGA are splice variants of each other. Specifically, their C-terminal regions are unique (i.e., residues 550-603 of mouse GAC and residues 550-674 of mouse KGA). Likewise, human GAC and KGA proteins each have unique C-terminal regions (i.e., residues 545-598 of human GAC and residues 545-669 of human KGA). In each of the mouse and human GAC and KGA proteins, amino acid residues 1-72 comprise the mitochondrial targeting sequence.

The human GAC protein is set forth in GenBank Accession No. NP_001243239.1, which is hereby incorporated by reference in its entirety, and has the amino acid sequence of SEQ ID NO:1, as follows:

```
Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365
```

-continued

```
Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575

Pro Glu Ser Asn Glu Asp Ile Ser Thr Thr Val Val Tyr Arg Met Glu
            580                 585                 590

Ser Leu Gly Glu Lys Ser
```

The cDNA sequence encoding the human KGA protein, infra, is set forth in GenBank Accession No. NM_014905.4, which is hereby incorporated by reference in its entirety, and has the nucleotide sequence of SEQ ID NO:2, as follows:

```
agtgcggagc cttaggcgga gcgaagagaa ccggtcgcgg caatcctagc gcgcagcagc    60

agcagcagca gcagcagcag cagcagcagc agcagcagca cccgcatccg ctgcgggagt   120

ccgagccgga accacaccca agtagctgcc ctttcctctt ctgtcatctc accgccccac   180

cacagaccgc gttccccgag gaaaccggcc gcccacgccc ggagcatcct cccctgttga   240

gcgggcgctg acggacccgg cggcatgatg cggctgcgag gctcggggat gctgcgggac   300

ctgctcctgc ggtcgcccgc cggcgtgagc gcgactctgc ggcgggcaca gcccttggtc   360

accctgtgcc ggcgtccccg aggcggggga cggccggccg cgggcccggc tgccgccgcg   420

cgactccacc cgtggtgggg cgggggcggc tggccggcgg agcccctcgc gcggggcctg   480

tccagctctc cttcggagat cttgcaggag ctgggcaagg ggagcacgca tccgcagccc   540

ggggtgtcgc cacccgctgc cccggcggcg cccggcccca aggacggccc cggggagacg   600

gacgcgtttg gcaacagcga gggcaaagag ctggtggcct caggtgaaaa taaaataaaa   660

cagggtctgt tacctagctt ggaagatttg ctgttctata caattgctga aggacaagag   720

aaaatacctg ttcataaatt tattacagca ctcaaatcta caggattgcg aacgtctgat   780

cccaggttga aagagtgtat ggatatgtta agattaactc ttcaaacaac atcagatggt   840

gtcatgctag acaaagatct ttttaaaaaa tgtgttcaga gcaacattgt tttgttgaca   900

caagcattta gaagaaagtt tgtgattcct gactttatgt cttttacctc acacattgat   960
```

-continued

```
gagttatatg aaagtgctaa aaagcagtct ggaggaaagg ttgcagatta tattcctcaa  1020
ctggccaaat tcagtcccga tttgtggggt gtgtctgttt gtacagtaga tggacagagg  1080
cattctactg gagataccaa agttcccttc tgtcttcagt cctgtgtaaa acctttgaaa  1140
tatgccattg ctgttaatga tcttggaact gaatatgtgc atcgatatgt tggaaaagag  1200
ccgagtggac taagattcaa caaactattt ttgaatgaag atgataaacc acataatcct  1260
atggtaaatg ctggagcaat tgttgtgact tcactaataa agcaaggagt aaataatgct  1320
gaaaaatttg actatgtcat gcagtttttg aataagatgg ctggtaatga atatgttgga  1380
ttcagtaatg caacgtttca gtctgaaaga gaaagtggag atcgaaattt tgcaatagga  1440
tattacttaa aagaaaagaa gtgttttcca gaaggcacag acatggttgg tatattagac  1500
ttctacttcc agctgtgctc cattgaagtg acttgtgaat cagccagtgt gatggctgcg  1560
acactggcta atggtggttt ctgcccaatt actggtgaaa gagtactgag ccctgaagca  1620
gttcgaaata cattgagttt gatgcattcc tgtggcatgt atgacttctc agggcagttt  1680
gctttccatg ttggtcttcc tgcaaaatct ggagttgctg gggcattct tttagttgtc  1740
cccaatgtta tgggtatgat gtgctggtct cctcctctgg ataagatggg caacagtgtt  1800
aagggaattc acttttgtca cgatcttgtt tctctgtgta atttccataa ctatgataat  1860
ttgagacact ttgcaaaaaa acttgatcct cgaagagaag gtggtgatca aagggtaaag  1920
tcagtgataa atcttttgtt tgctgcatat actggagatg tgtctgcact tcgaagattt  1980
gctttgtcag ctatggacat ggaacagcgg gactatgatt ctagaacagc actccatgta  2040
gctgctgcag agggtcatgt tgaagttgtt aaatttttgc tggaagcctg caaagtaaac  2100
cctttcccca aggacaggtg gaataacact cccatggatg aagcactgca ctttggacac  2160
catgatgtat ttaaaattct ccaagaatac caagtccagt acacacctca aggagattct  2220
gacaacggga aggaaaatca aaccgtccat aagaatcttg atggattgtt gtaatggtct  2280
caaatcccaa gatttaaatc acttacctat ttaattgtgg aaaatgatta tgaagaacat  2340
gtgtatttct atctggtagt gatgtatatt ttacatttgt catttcagtg ttactggagt  2400
tttcttcatt gtgcacacag gacaaatctg atctctttgg gaaaaaatag aaataaaaca  2460
atctccctcc ataatgtgag caatattacc tcgtgcattg tataatttga tgtaaaagaa  2520
atagttacca atgctagctt gtgtggtctt ccatgattta tttgtgtttt gtgaattttc  2580
aatttatggt gatgatctgc tgatatgcat ttataaagta agctctgttg tacagtctgt  2640
ccaaatgggt caaggttgcc tttagaagca aatagtgtga ttttcaagac ttcaaataca  2700
aatttagttt aagtgtttga acaactatat gcacttacgg ttgtgtgttt aaaatgtctc  2760
tctcaccccc tagcttcatg atgtgactct taaaaaacta taatagttaa caactgttag  2820
taagatagac caattctgat tagactttat cagggaatct gtttaagata tgtttggtga  2880
ccaaaacgta tgtgtgaatg tagttataat gcttttgaaa aattttcctt tttctatatc  2940
cccttagtcc agcctctctt ctcagacatt tagctatctg cctctttcct ttagctggga  3000
aagtgagagc tggcatacta tgcagttttt atgttttcca tagtaagtca gaaaatgcct  3060
cctatttctg gcatcagaac tttgccattt gtctacagaa gacgaaccag agacaaaatt  3120
actaagtata aattagtcaa gtttatcagt ctaaaaaacg aagggatgtg caactgcagc  3180
tctttaagaa gttttttttt tttagcttct agggtaaaga taaattcaga aatgctctaa  3240
gctaccaaag ttattctgaa agtatgggaa ctgctacaac taacaaacat ttgtttccaa  3300
gcctgtcatt aagagtctgc atcaagagat ttgtcctcct tgggggacca ctggatcatt  3360
ccagatttct tgtgattttt ctattgtgta attcttggtg ggctctgtag tttaataata  3420
```

-continued agaaaaaggc catttcattt taaattgtga cctataattc tttgtcttgg gttggtaatt 3480
caggattcat ttggaaagtg ggtaaaaggg gcttcaaaaa acggatagaa caggattttc 3540
taggagttac acatacattt tatcctgtca tacctcgaga taaagtggca tgttagtgag 3600
gagttctgat attaagcaca cacacacatg cacacaaatg gacttctctg aagctgtgtt 3660
tagtgaaatg agctcaagta catgaatgtt agttgttatc acatacagca aattcctttt 3720
tttttctttt tctatgagca cactctgctg cttctaaact ttacatgcct gatggcacct 3780
tactccagca gcctccaggt gctttcattt tcacttccag tctaagccag tggctcctgc 3840
cactgccctc ccattaccta gatggcacct cctttggtga aaccacggcc aatgttcctt 3900
agctgcacca ggcccgaagc tgttcccatg cttgagcttc catggggagg atgctgagtg 3960
agcagtttcc taccccgtgg atctagcaag ccatggagac aggtagcatt tgtaagatgc 4020
tgcacaggag cagcattatc cccaaagata ttacagggta gacacgtttt aactgaaatc 4080
aatcaagata actttattca aagagcagcc cgctttgtgt gactaaaatg aaacaagaca 4140
gttgaattgt gtgacttgaa gattaccaat gattttgagg cttttctata ataaaaagag 4200
gttctaacca ttatttggga acaaagagag ttttcatctt ttttcagatc aaaaccattc 4260
tgtaaaatct ttgttgttta attaaatgtg ccgttattta cccctgatgt tatttatgac 4320
tatgtgccga ttcctgctcg ggctgtttgc tgttggctgg taataatata tttgatttaa 4380
atgctgttga ctgtgctatt aactgctgcc gtcagtaaac tccaaagatc tttttgtttt 4440
ggctttagta tcatatgtgc tttttctgta tcctgagcgc tctatatgat catgttaatt 4500
taaagcttta tacacattgt tgtttttgct ggtctcatct ttggtaatat gctatacccc 4560
actgctgccc gacactgccc tttagctgca gagctggatt agctgttgac catttgatgc 4620
tgttgtctgt ctggcaggga ctgaatgacc tgatgtcaga tttagattct tcctggggat 4680
tacacagcta tgaatgtatt tgcttctaaa acctcccaaa gtgaatctaa tcttaaaact 4740
acaagttgta agtattctga aattgggaaa catttatttt aaatgcaatc aggtagtgtt 4800
gctttttaca gcataataaa tatatgtatc aaaaaaaaaa aaaaaaaaaa 4850

The mouse GAC protein is set forth in GenBank Accession No. NP_001106854.1, which is hereby incorporated by reference in its entirety, and has the amino acid sequence of SEQ ID NO:3, as follows:

Met Met Arg Leu Arg Gly Ser Ala Met Leu Arg Glu Leu Leu Leu Arg
1 5 10 15

Pro Pro Ala Ala Val Gly Ala Val Leu Arg Arg Ala Gln Pro Leu Gly
20 25 30

Thr Leu Cys Arg Arg Pro Arg Gly Gly Ser Arg Pro Thr Ala Gly Leu
35 40 45

Val Ala Ala Ala Arg Leu His Pro Trp Trp Gly Gly Gly Gly Arg Ala
50 55 60

Lys Gly Pro Gly Ala Gly Gly Leu Ser Ser Ser Pro Ser Glu Ile Leu
65 70 75 80

Gln Glu Leu Gly Lys Gly Gly Thr Pro Pro Gln Gln Gln Gln Gln Gln
85 90 95

Gln Gln Gln Pro Gly Ala Ser Pro Pro Ala Ala Pro Gly Pro Lys Asp
100 105 110

Ser Pro Gly Glu Thr Asp Ala Phe Gly Asn Ser Glu Gly Lys Glu Met
115 120 125

-continued

```
Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg His Ser Phe Gly Pro
545                 550                 555                 560
```

-continued

```
Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
            580                 585                 590

Val Tyr Arg Met Glu Ser Leu Gly Glu Arg Ser
        595                 600
```

The cDNA sequence encoding the above mouse GAC protein is set forth in GenBank Accession No. NM_001113383.1, which is hereby incorporated by reference in its entirety, and has the nucleotide sequence of SEQ ID NO:4, as follows:

```
tgagcgtcag tctcagtgcg gagctcgcgg cggccagagc aacttcggct ggctgcaggc    60

tgggcggcgg cggcggcgag ggcggcggcg ttggcggcgg gagcggcgga gctggggcca   120

caccccgtcc cggacttttt ctctttccag tcctctcccc gccgtgcggg acacggttcc   180

gggagcagag cggccgccca cgccccaagc atcctcatct gacgagcggg cgccggcggt   240

atgatgcggc tgcgaggctc ggcgatgcta cgggagctgc tcttaaggcc gcccgccgcc   300

gtcggagccg tcctgcggcg cgcgcagccc ctcggcacgc tgtgccggcg cccccggggc   360

gggagccggc cgaccgctgg cctggtggcc gctgcgcgac tccacccgtg gtggggcggg   420

ggcggccgcg cgaagggccc cggcgcgggc ggcctgtcca gttcgccctc ggagatccta   480

caggagctgg ggaagggggg tacgccgcca cagcagcagc agcagcagca gcagcagcca   540

ggggcgtcgc cacccgcagc cccgggcccc aaggacagcc cgggggagac cgacgcgttc   600

ggcaacagcg agggcaagga gatggtggcc gcgggcgaca ataaaaataa acagggtctg   660

ttacctagct tggaagattt gctgttctat acaattgcag aaggacaaga aaagatacct   720

gttcacaagt ttattacagc actcaaatct acaggattgc gaacatctga tcccaggttg   780

aaagagtgta tggatatgtt aagattaact cttcagacaa cgtcagatgg tgtcatgcta   840

gacaaagatc tttttaaaaa gtgtgttcaa agcaacattg ttttgttgac acaagcattt   900

agaagaaagt ttgtcattcc tgactttatg tcttttacct cacacatcga tgagttatat   960

gaaagtgcta aaaagcagtc tggagggaag gttgctgatt atattcctca gctggccaaa  1020

ttcagtcctg atttgtgggg tgtatctgtc tgtactgtag atgggcaaag gcattctatt  1080

ggagatacca aagttccttt ttgtcttcag tcctgtgtaa aacccctgaa atatgcaatt  1140

gctgttaatg acctgggaac tgagtatgta catcgctatg ttgggaagga gccaagtgga  1200

ttaagattca acaaactctt tttgaatgaa gatgataaac cacataatcc tatggtaaat  1260

gctggagcaa ttgttgtgac ttctctaata aagcaaggag taaataatgc tgagaagttt  1320

gactacgtga tgcaattttt gaataagatg gctggtaatg aatatgttgg attcagtaat  1380

gcaacgtttc agtctgaacg agaaagtgga gatcgaaatt ttgcaatagg atattactta  1440

aaagaaaaga agtgttttcc agaaggcaca gacatggttg ggatactaga tttttacttc  1500

cagctgtgct ctattgaagt gacatgtgaa tcagcaagtg tgatggctgc caccttggct  1560

aatggtggtt tctgcccaat tactggtgaa agagtcctca gtcctgaggc agttcggaat  1620

acactgagct tgatgcattc ttgtggcatg tatgacttct cagggcagtt tgcgttccat  1680

gttggtcttc ctgcaaaatc tggagttgct gggggtattc ttttagttgt ccccaacgtc  1740

atgggcatga tgtgttggtc tcctcctctt gacaagatgg gcaacagtgt taagggaatt  1800

cacttttgtc acgatcttgt ttctctgtgt aacttccata actatgataa tttgagacac  1860

tttgcaaaaa aacttgatcc tcggagagaa ggaggtgatc aaaggcattc ctttggacca  1920
```

-continued

```
ttggactatg agagtctcca gcaagaactt gctttaaaag acacagtatg gaaaaaagtg  1980
tcacctgagt caagtgacga cacctctaca actgtagtat atagaatgga gagtctgggg  2040
gagaggagct agagatgggc tctagctaca gaacagaacg attctccttt taacatcgga  2100
aacatcttta ggcttttgtt tcttgtttat ctttccaaac taagtattta ttcaagtatt  2160
ctattgttat cagttttggg tactggagcc ataaatttaa aaaaaggttc tgttttggtt  2220
tggttttttt tcgcttgtaa tctttgtata aaaaacattt gttatttttt aaaagagcat  2280
ttacaaataa agcaaatttg ctttattttt taaaactttt ttaaaaaatg caatttcctt  2340
aattacatta aaaatttaac tataaaattt ggtaaccaca ttgtttttct tagttctgaa  2400
gcctgcatat taaactgagg cgtattgttg gatttgtctt ttcctttcca gttttataat  2460
tgataggcta tattggtagt gacagaaagt acttccatgc taaatataaa actaaaaagg  2520
caaagtaatc aaaattattt aaaagagtac tagattataa aattagcttt agtttacaca  2580
tatgccagtt atagcggtag attggctttg aatatttaaa atgcaaatac ttttaaatat  2640
gtcttttttt ttgtttgaaa agttctgtcc tgtcagaatc acaatgtatt aggaatgttt  2700
cacatcactg aaacactcca gccaaagaat tgcagatgtg tgagaatggc atgccctgtt  2760
atttaaaagc tacaatggtt agttgctcag aaaaagagtc aataactatc ttcaaaatgg  2820
attgtatttt catattcttc atgtaatttt tttgttgtat ttaagtatga acggtaaatt  2880
ttgctttttt agcttttagt aattttatta tgtttcataa gtgctaatga atattttgtg  2940
ataattataa catctcataa attttgttct ttttgaactt ttattagcat acttatgaaa  3000
tgaatatagt ttgaaggtgt taagtataca actaaaatat ttgttgaatt ggaatgcttc  3060
tgtttatttt taaaatgcaa tattgagaat caaaactttt ttcaagagaa tcataggttc  3120
cattttatct cgtcataaac agatatacat atttttagaa tctatcttgg caaaatgata  3180
ctaatgttct gcaggattta tttacatgtc ttccttcgtg tattttgttt ttctcacaat  3240
ttcaagtttg gtttttcaaa ttcactttta aacttgtaaa ttttgggcaa gtggttgaga  3300
atgaaagcct tattgctttt taaattatgg cacatgtata gtagagcaga ttctgtaact  3360
aaagaaagtg cgggaaaaat agttcactga taggctaagt aagatacagg aaagtcctga  3420
tggtctgatt tgaaactggg aactctgata ttaagaaaag ggttcttctc agaagttcga  3480
ccttaaagcc tttgggctaa cttaagtatt actatttgta tttaaataat tacatggtgg  3540
gttttagaaa ggctggctgt cctgcccctt tggtgttcat atgcattccc cagcctgatg  3600
ctttaaaagc cttgccactg ccctgcttgt ggacactaat catctctttt tcttgtatcc  3660
agagtgactg tgattcaggt aattgagcac catgattgga aaaaagattt taggtttatt  3720
tcccctccat ttttatgtgt acattttgtt gtttcattca gaagttggat ttactttaca  3780
aaatgactta attttcatat tgtggtcatg tttgtgtaaa cttcaaacta ttttgttaat  3840
ttttggcact tcctatatat aattctagta atgcttgaat gtacacttaa atatgaagta  3900
ggattaagtc agctgctgtg tttaaagaat gctgttaaga acaagcattc aaaactgtat  3960
aggaaggtat tagcttaaga gtaggtaaga taccgtgact gtatctgcag acaagaagag  4020
gaaagaaaag ctttgccagt ttgtggattt atcttaattc ccttcagtat attcaatctc  4080
ttttcaaata aagctctttg agaagtaccc agtattgttg ggtttaattt ttcctactat  4140
tattgattct tgatattcaa gcatttacat gacagcgtat tttttctttt tccttttttc  4200
tgtttatttt tttttgctat cattaacatt tcatttgaaa tgcatactct tcttgaaata  4260
ttttgttttt agcataaatg ttgtgcattt tatcttagtg tttggattaa aacatttgtg  4320
```

-continued

```
ttgttgagct ttcttcattt gctttgtata tttaataatg tatctttatt ttccagtatg  4380

cctatttttt gtattgtaca ataaatttat tttaagctg                         4419
```

The human KGA protein is set forth in GenBank Accession No. NP_055720.3, which is hereby incorporated by reference in its entirety, and has the amino acid sequence of SEQ ID NO:5, as follows:

```
Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

               Gln Ser Gly Gly Lys Val Ala Asp Tyr Ile Pro Gln
                               245                 250

Leu Ala Lys Phe Ser Pro Asp Leu Trp Gly Val Ser Val Cys Thr Val
        255                 260                 265

Asp Gly Gln Arg His Ser Thr Gly Asp Thr Lys Val Pro Phe Cys Leu
    270                 275                 280

Gln Ser Cys Val Lys Pro Leu Lys Tyr Ala Ile Ala Val Asn Asp Leu
285                 290                 295                 300

Gly Thr Glu Tyr Val His Arg Tyr Val Gly Lys Glu Pro Ser Gly Leu
                305                 310                 315

Arg Phe Asn Lys Leu Phe Leu Asn Glu Asp Asp Lys Pro His Asn Pro
            320                 325                 330

Met Val Asn Ala Gly Ala Ile Val Val Thr Ser Leu Ile Lys Gln Gly
        335                 340                 345

Val Asn Asn Ala Glu Lys Phe Asp Tyr Val Met Gln Phe Leu Asn Lys
    350                 355                 360
```

-continued

```
Met Ala Gly Asn Glu Tyr Val Gly Phe Ser Asn Ala Thr Phe Gln Ser
365                 370                 375                 380

Glu Arg Glu Ser Gly Asp Arg Asn Phe Ala Ile Gly Tyr Tyr Leu Lys
                385                 390                 395

Glu Lys Lys Cys Phe Pro Glu Gly Thr Asp Met Val Gly Ile Leu Asp
            400                 405                 410

Phe Tyr Phe Gln Leu Cys Ser Ile Glu Val Thr Cys Glu Ser Ala Ser
        415                 420                 425

Val Met Ala Ala Thr Leu Ala Asn Gly Gly Phe Cys Pro Ile Thr Gly
    430                 435                 440

Glu Arg Val Leu Ser Pro Glu Ala Val Arg Asn Thr Leu Ser Leu Met
445                 450                 455                 460

His Ser Cys Gly Met Tyr Asp Phe Ser Gly Gln Phe Ala Phe His Val
                465                 470                 475

Gly Leu Pro Ala Lys Ser Gly Val Ala Gly Gly Ile Leu Leu Val Val
            480                 485                 490

Pro Asn Val Met Gly Met Met Cys Trp Ser Pro Pro Leu Asp Lys Met
        495                 500                 505

Gly Asn Ser Val Lys Gly Ile His Phe Cys His Asp Leu Val Ser Leu
    510                 515                 520

Cys Asn Phe His Asn Tyr Asp Asn Leu Arg His Phe Ala Lys Lys Leu
525                 530                 535                 540

Asp Pro Arg Arg Glu Gly Gly Asp Gln Arg Val Lys Ser Val Ile Asn
                545                 550                 555

Leu Leu Phe Ala Ala Tyr Thr Gly Asp Val Ser Ala Leu Arg Arg Phe
            560                 565                 570

Ala Leu Ser Ala Met Asp Met Glu Gln Arg Asp Tyr Asp Ser Arg Thr
        575                 580                 585

Ala Leu His Val Ala Ala Ala Glu Gly His Val Glu Val Val Lys Phe
    590                 595                 600

Leu Leu Glu Ala Cys Lys Val Asn Pro Phe Pro Lys Asp Arg Trp Asn
605                 610                 615                 620

Asn Thr Pro Met Asp Glu Ala Leu His Phe Gly His His Asp Val Phe
                625                 630                 635

Lys Ile Leu Gln Glu Tyr Gln Val Gln Tyr Thr Pro Gln Gly Asp Ser
            640                 645                 650

Asp Asn Gly Lys Glu Asn Gln Thr Val His Lys Asn Leu Asp Gly Leu
        655                 660                 665

Leu
```

The cDNA sequence encoding the above human GAC protein is set forth in GenBank Accession No. NM_001256310.1, which is hereby incorporated by reference in its entirety, and has the nucleotide sequence of SEQ ID NO:6, as follows:

```
agtgcggagc cttaggcgga gcgaagagaa ccggtcgcgg caatcctagc gcgcagcagc    60

agcagcagca gcagcagcag cagcagcagc agcagcagca cccgcatccg ctgcgggagt   120

ccgagccgga accacaccca agtagctgcc ctttcctctt ctgtcatctc accgccccac   180

cacagaccgc gttccccgag gaaaccggcc gcccacgccc ggagcatcct cccctgttga   240

gcgggcgctg acggacccgg cggcatgatg cggctgcgag gctcggggat gctgcgggac   300

ctgctcctgc ggtcgcccgc cggcgtgagc gcgactctgc ggcgggcaca gcccttggtc   360

accctgtgcc ggcgtccccg aggcggggga cggccggccg cgggcccggc tgccgccgcg   420
```

-continued

```
cgactccacc cgtggtgggg cgggggcggc tggccggcgg agcccctcgc gcggggcctg   480
tccagctctc cttcggagat cttgcaggag ctgggcaagg ggagcacgca tccgcagccc   540
ggggtgtcgc cacccgctgc cccggcggcg cccggcccca aggacggccc cggggagacg   600
gacgcgtttg gcaacagcga gggcaaagag ctggtggcct caggtgaaaa taaaataaaa   660
cagggtctgt tacctagctt ggaagatttg ctgttctata caattgctga aggacaagag   720
aaaataacctg ttcataaatt tattacagca ctcaaatcta caggattgcg aacgtctgat   780
cccaggttga aagagtgtat ggatatgtta agattaactc ttcaaacaac atcagatggt   840
gtcatgctag acaaaagatct ttttaaaaaa tgtgttcaga gcaacattgt tttgttgaca   900
caagcattta gaagaaagtt tgtgattcct gactttatgt cttttacctc acacattgat   960
gagttatatg aaagtgctaa aaagcagtct ggaggaaagg ttgcagatta tattcctcaa  1020
ctggccaaat tcagtcccga tttgtggggt gtgtctgttt gtacagtaga tggacagagg  1080
cattctactg gagataccaa agttcccttc tgtcttcagt cctgtgtaaa acctttgaaa  1140
tatgccattg ctgttaatga tcttggaact gaatatgtgc atcgatatgt tggaaaagag  1200
ccgagtggac taagattcaa caaactattt ttgaatgaag atgataaacc acataatcct  1260
atggtaaatg ctggagcaat tgttgtgact tcactaataa agcaaggagt aaataatgct  1320
gaaaaatttg actatgtcat gcagtttttg aataagatgg ctggtaatga atatgttgga  1380
ttcagtaatg caacgtttca gtctgaaaga gaaagtggag atcgaaattt tgcaatagga  1440
tattacttaa aagaaaagaa gtgttttcca gaaggcacag acatggttgg tatattagac  1500
ttctacttcc agctgtgctc cattgaagtg acttgtgaat cagccagtgt gatggctgcg  1560
acactggcta atggtggttt ctgcccaatt actggtgaaa gagtactgag ccctgaagca  1620
gttcgaaata cattgagttt gatgcattcc tgtggcatgt atgacttctc agggcagttt  1680
gctttccatg ttggtcttcc tgcaaaatct ggagttgctg gggcattct tttagttgtc   1740
cccaatgtta tgggtatgat gtgctggtct cctcctctgg ataagatggg caacagtgtt  1800
aagggaattc acttttgtca cgatcttgtt tctctgtgta atttccataa ctatgataat  1860
ttgagacact ttgcaaaaaa acttgatcct cgaagagaag gtggtgatca aaggcattcc  1920
tttggaccat tggactatga aagtctccaa caagaacttg ctttaaaaga gacagtatgg  1980
aaaaaagtgt cacctgagtc aaatgaggac atctctacaa ctgtagtata tagaatggaa  2040
agtctgggag agaaaagcta aagaaatggg ttctagtttc agaatgtttc ttcatttaat  2100
ctttcaaaca tctttagctt ttttttgcaa gttataaata tttatttgag gtatttttg   2160
ttctcaatct tgggtgctgg agccataaag ctttttttc cttttaatct ttgtataaag   2220
gcagtagatt aagaagtgca tttgttggtc tttaaaaagt atttacaagt acataaattt  2280
gctttatttt taaaaataca aaaaggaaaa atttaaattt tttttgatgt aattaaaatg  2340
ttaactatgt ggtcagataa tcccatttta caatagtaac agaaaattgt aattcttagt  2400
tctaaaattc acaaattaaa ctcataagtt ttgttgcatt ttgttttttc ttttccattt  2460
ttaaaactaa tgtgatgtct ttagtggcaa tagaaggtac ttctatgcta aatacaaaac  2520
taaaaaggca aaataatgaa ccccaaatta ttttatttaa aatagcagtg gattataaaa  2580
ttagcttgtg tttacattta tgccattttt ggtgatagat tggctttaca ttttaaaaaa  2640
tttatttaaa aatttatcaa atgctttaaa atatgactcc tacttttttt attttgcaac  2700
tcctctgttc tgtcagagtt gttatataca ggagtgtctt atgttactaa aacattccag  2760
ccaaagaatt tcagatgtga gataatgatg tttcatcaat aaaaagctat aatggttagt  2820
tactcagaag gagaaacagt gagtgtcttc aagtgaattg ttcacctaaa caattttatt  2880
```

-continued

```
ttcatattat ccacataact ttttctatgt tatatttaaa tatgaatggc aaattttggt  2940

ttttagcttt tacattttat tatcttaatt ttataaatgc taatatttct tttgtgataa  3000

gttatagcat ctcataaagt ttgttctatt tgaagttttt tagagtactt gagaaatgaa  3060

tttagtctgc aggtagtaag tatgctacta aaatacgtta gatctaaatc cttttatttg  3120

gtataaaaat gcaatattga gaatcaaaac ttgtttttaa gagaactata gattctacac  3180

aacctgattt caagtaatta ttcatagtat ttatagttgt cttggcaaag tgattgtaaa  3240

attctgtagg acctattcac acttcttcct tcttccatat acttctctgg ttttccccat  3300

agttccccta taatttcaag tttgttgaaa cctgttaatt ttagtggggg attagaagaa  3360

aaacttggtg gtttcttagc atgatggtgt atgtatgtgg taatggaaag tctgtaaaag  3420

taaatatagt gtagcaaaaa agatttcact gagtatttta gatactagtg caaataaaga  3480

tagaaaatct tgatcataat gtcttaagtt tgggaactgt gatattaaga aaagaaattc  3540

ccttctagag gtgctggcca aaaagccttt tgggctaact taagtattaa atttatatat  3600

ttaaataatt atattttaag ttgtagagga ttttcccaag gattttatgc ttacttgaat  3660

gttctttgaa tgttcagatg catatcctaa ctggatgctt ctcaaggcct tactgcatat  3720

ttgtgttgca tatttatgtt agttgcacca gggccattg tagtttgggc aaccgaatgc  3780

cttaattgga aaaaaggcat tgtggtttcc cctatgatct aaattgttac attttaccat  3840

ttcattccga agttggtttt actttattaa atgaagattt agttttcata tcgtatacat  3900

agctgtatag atttcaaaat taggttgtta atttgtgtca cttactattt ttgtgttggt  3960

aatgctttaa atgcatactt aaaaatgaag tactgttatc taagctactg tgtttagaaa  4020

atgttaagaa tgagcagaaa tttttataga aaagtataaa cggaagaaga gataagatac  4080

tgcgaatagg ccctcaaact taaaaaagaa aaaactttgc cagttttaag gacatatttt  4140

gattctttca gtattcttaa caccttttta aacaaagttc ttgatagtac ccactattat  4200

tgggtttgtt ttatgccatt attgattctt gatattcaag catttacaat gtagcatatt  4260

tgattttctt ttttctttct ttttttggca tcattaacat ttcatttgaa atgcatattg  4320

ttcttgaagt actttgtttt tagcataaat gttgtgcatt ttatcttagt gtttggatga  4380

aaacatttgt gttgtttagc tttcatttgc tttgtatatt taataatgta cctttatttt  4440

ccagtatgcc tacattttgt attgcacaat aaatttattt taagctgaaa aaaaaaaaaa  4500

aaaaaaaaa                                                          4509
```

The mouse KGA protein is set forth in GenBank Accession No. NP_001074550.1, which is hereby incorporated by reference in its entirety, and has the amino acid sequence of SEQ ID NO:7, as follows:

```
Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Gly Arg Ala
    50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95
```

-continued

```
Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525
```

-continued

```
Leu Cys Asn Phe His Asn Tyr Asp Asn Leu Arg His Phe Ala Lys Lys
    530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Ala Glu Gly His Val Glu Val Val Lys
        595                 600                 605

Phe Leu Leu Glu Ala Cys Lys Val Asn Pro Phe Pro Lys Asp Arg Trp
    610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu
```

The cDNA sequence encoding the above mouse KGA protein is set forth in GenBank Accession No. NM_001081081.2, which is hereby incorporated by reference in its entirety, and has the nucleotide sequence of SEQ ID NO:8, as follows:

```
tgagcgtcag tctcagtgcg gagctcgcgg cggccagagc aacttcggct ggctgcaggc     60

tgggcggcgg cggcggcgag ggcggcggcg ttggcggcgg gagcggcgga gctggggcca    120

caccccgtcc cggacttttt ctctttccag tcctctcccc gccgtgcggg acacggttcc    180

gggagcagag cggccgccca cgccccaagc atcctcatct gacgagcggg cgccggcggt    240

atgatgcggc tgcgaggctc ggcgatgcta cgggagctgc tcttaaggcc gcccgccgcc    300

gtcggagccg tcctgcggcg cgcgcagccc ctcggcacgc tgtgccggcg cccccggggc    360

gggagccggc cgaccgctgg cctggtggcc gctgcgcgac tccacccgtg gtggggcggg    420

ggcggccgcg cgaagggccc cggcgcgggc ggcctgtcca gttcgccctc ggagatccta    480

caggagctgg ggaagggggg tacgccgcca cagcagcagc agcagcagca gcagcagcca    540

ggggcgtcgc cacccgcagc cccgggcccc aaggacagcc cgggggagac cgacgcgttc    600

ggcaacagcg agggcaagga gatggtggcc gcgggcgaca ataaaataaa acagggtctg    660

ttacctagct tggaagattt gctgttctat acaattgcag aaggacaaga aaagatacct    720

gttcacaagt ttattacagc actcaaatct acaggattgc gaacatctga tcccaggttg    780

aaagagtgta tggatatgtt aagattaact cttcagacaa cgtcagatgg tgtcatgcta    840

gacaaagatc tttttaaaaa gtgtgttcaa agcaacattg ttttgttgac acaagcattt    900

agaagaaagt ttgtcattcc tgactttatg tcttttacct cacacatcga tgagttatat    960

gaaagtgcta aaaagcagtc tggagggaag gttgctgatt atattcctca gctggccaaa   1020

ttcagtcctg atttgtgggg tgtatctgtc tgtactgtag atgggcaaag gcattctatt   1080

ggagatacca aagttccttt ttgtcttcag tcctgtgtaa aacccctgaa atatgcaatt   1140

gctgttaatg acctgggaac tgagtatgta catcgctatg ttgggaagga gccaagtgga   1200

ttaagattca acaaactctt tttgaatgaa gatgataaac cacataatcc tatggtaaat   1260

gctggagcaa ttgttgtgac ttctctaata aagcaaggag taaataatgc tgagaagttt   1320
```

-continued

```
gactacgtga tgcaattttt gaataagatg gctggtaatg aatatgttgg attcagtaat  1380
gcaacgtttc agtctgaacg agaaagtgga gatcgaaatt ttgcaatagg atattactta  1440
aaagaaaaga agtgttttcc agaaggcaca gacatggttg ggatactaga tttttacttc  1500
cagctgtgct ctattgaagt gacatgtgaa tcagcaagtg tgatggctgc caccttggct  1560
aatggtggtt tctgcccaat tactggtgaa agagtcctca gtcctgaggc agttcggaat  1620
acactgagct tgatgcattc ttgtggcatg tatgacttct cagggcagtt tgcgttccat  1680
gttggtcttc ctgcaaaatc tggagttgct gggggtattc ttttagttgt ccccaacgtc  1740
atgggcatga tgtgttggtc tcctcctctt gacaagatgg gcaacagtgt taagggaatt  1800
cacttttgtc acgatcttgt ttctctgtgt aacttccata actatgataa tttgagacac  1860
tttgcaaaaa aacttgatcc tcggagagaa ggaggtgatc aaagggtgaa gtcggtgata  1920
aaccttctgt ttgccgcata cactggagat gtgtctgccc tccgaaggtt tgctctgtca  1980
gccatggaca tggagcagcg ggattatgac tccagaacag ccctccatgt cgcagcagca  2040
gagggtcatg ttgaagttgt caagtttttg ctggaagctt gcaaagtaaa ccctttcccc  2100
aaggacaggt ggaataatac ccccatggat gaagcactac actttggaca ccatgatgtt  2160
tttaaaatcc ttcaggaata ccaagttcag tacacacctc aaggggattc tgatgatgga  2220
aagggaaacc agactgtcca caagaatctc gacgggttgc tataatggtc tgcaccccaa  2280
gacttccatt acttacctag tcattgtgga acatgactat ggagagcatt gtatatttct  2340
atctggtagt aatgtgtatt tacaacatct gtcactgcag tgttaccgga gcttccttca  2400
ttgtgcgcac acgacaaatc tgagttcttt gggaaaaaaa tagaaatgaa gcagcctccc  2460
ttcataatgt gagcaatagt tacctcgtgc attgtacaat gtggtgtaaa agagtagtta  2520
ccaatgccag ctgaactgtg tggtcttcat ggtttgcgtt ctgtacattt tcaagccctg  2580
gtgatgatac gctcatatgc acttaggagt gagctttgtt gtacagtctg tccacggggt  2640
cgatgctgtt attaggtgaa aatagtgtga tctttaagac tttaaataca gatttagttt  2700
tgagtgtttg agagaccact acacttgtat ggttgagtgt ttaaaatgtc tatcaccctc  2760
acttcagagt gtgactcttt aaatattaaa atagatacta actgttcata gaacaggccg  2820
attctgatta gattttatca gggaatctgt taagatatgt ttggtgacca aaacgtatgt  2880
gtgaatatag ttctagcact tttaaatttt tcctttccat acaacgcttg ggccagcctc  2940
tctgtgctgc gtggctgtcg gtccccctca gctgggaaag agagcactgg ctcactgtgc  3000
agttttcatg tttcctcagc aagccatcaa gcctcacatc tctaccatca gagatagagc  3060
ttggccattt atctaaggaa gatgagccaa aattatgaca tctaaaataa tcgtcagtct  3120
taagagtaaa gacagcgaaa ctgcacactt ataagttctt ttcagcttct acaataaaga  3180
aaagttcaga aatgctttca gttaccaaag ttataacgat atatttagga aaagctacaa  3240
ataacactta ctttgaatcc tgctgtcaaa tgtctgcatc aagatagcac ccctttgtgg  3300
gaggccctga gtatcttctc ttcctctact gcctaactgt tggtgggctg tatcattcaa  3360
taagatcact tcattttcaa cttagaccca ccgtttcttt tttgttgttt tgttttgttt  3420
ggtttggttt ggttgggttg ggttgttgtt tttggttttt tcgagacagg gtttctctgt  3480
gtagccctgg ctgtcctgga actcactttg tagaccaggc tggccttgaa ctcagaaatc  3540
cgcctgcctc tgcctcccga gtgctgggat taaaggtgca aactaccacg cctggcagac  3600
ccaccatttc tttgctttgg aaaggtaatt tatgattaac ttagataata ggtaaaagcg  3660
accttacaaa aaacataatt atctaggagt cccacatact ggacctaccc tattatacct  3720
ccaagagata aagggtatgt tagtgaggac ttttgcacac aagtgcatgc acacttggca  3780
```

-continued

```
tacacacaca cacacacaca cacacacaca cacacacaca cacacggact tcttggaaac  3840

tgctttatga agaaactgct ttatgaaata agcaaaattc tcaagtgcac agatactagc  3900

agttatgaca gtaatacagc gtcttctgtg accctcacta cctgcactgc ttgcatccct  3960

gctttatgcc tggtggcaca ttattcaccc ggtaacctcc agctgctttg atcctgtttc  4020

agtcaaagtc agcttcagcc acccccctcca ttccctagcc agctccaccc ttgatgaaac  4080

tgtggctaat gttccttcac taggacaggc accatgagtg tgtttctaag ttccagagtc  4140

tgtggggagg atggtgggtg ggcagccagc cctgttgcta tgttgcttct tccacacccc  4200

ctcaagacag gtgcataggt ggcactggga acatcctacg cagggacaac ctccaaaatt  4260

aatgggtgaa catggttttt ttggaatcaa ctgagataat gctatttcaa tagcggctgg  4320

ctttttgtga ttcagtaact taaatattgc cagtgactga ggatcccctc cagtcatggt  4380

tctgtatatt ctttgagaca ggtgttttca tcttctctca gctcagtgct gttttgtaca  4440

gtctctgtgg cttggttgag tatgctcttt cctgtgccag gtcttgctct ggctgttcgc  4500

tactggctga taataacaag gaccctgtgt gtgtgtgaat gagccgctaa ctgctaccat  4560

ctgtaaactc caaagatctg tttgttttgg ctttacaatc ttagctaatt tttctgtatc  4620

ctggaaccat tacatgatca tgttgctttg aagatctttt tatgccactg tttctgctgt  4680

cttggttctg acacccctgt ctggtgatat gctataccccc agtgctgcct acacgtgctt  4740

tagctgtaga gctgggtata ctgttgatcc agctgtccgt cagggacttg ataacctgat  4800

gtttgatgta gatccctgct ggggagtcca caactatgaa tgtatttact tccaacattt  4860

cccaaaatga aaactataaa ttgcaagtat tctggaattg ggaaatactt attttaaatg  4920

agatcaggta gtgttgcttt ttacagcata ataaatatgt gtattgaaaa caaa        4974
```

Other GLS proteins are also contemplated as labeled glutaminase proteins according to this aspect of the present invention. Other GLS proteins include GLS proteins from other animal sources, i.e., GAC and KGA proteins from non-mouse and non-human sources. According to one embodiment, these and other GLS proteins have an amino acid sequence that is at least about 80%, 85%, 90%, 91%, 92%, 93%, 94%, 95%, 96%, 97%, 98%, or 99% identical to SEQ ID NO:1, SEQ ID NO:3, SEQ ID NO:5, and/or SEQ ID NO:7.

Percent identity as used herein refers to the comparison of one amino acid (or nucleic acid) sequence to another, as scored by matching amino acids (or nucleic acids). Percent identity is determined by comparing a statistically significant number of the amino acids (or nucleic acids) from two sequences and scoring a match when the same two amino acids (or nucleic acids) are present at a position. The percent identity can be calculated by any of a variety of alignment algorithms known and used by persons of ordinary skill in the art.

GLS proteins according to this embodiment of the present invention may be isolated from a sample or tissue by methods commonly used by persons of ordinary skill in the art, or produced recombinantly, e.g., from a GLS encoding nucleic acid molecule. For example, cDNA sequences that encode GLS proteins are set forth above and include, without limitation, SEQ ID NO:2, SEQ ID NO:4, SEQ ID NO:6, and SEQ ID NO:8.

Expression of a GLS protein can be carried out by introducing a nucleic acid molecule encoding the GLS protein into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted GLS protein coding sequence.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the GLS protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others including, but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The GLS protein-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a GLS protein is inserted into a vector in the sense (i.e., 5'→3') direction, such that the open reading frame is properly oriented for the expression of the encoded GLS protein under the control of a promoter of choice. Single or multiple nucleic acids may be ligated into an appropriate vector in this way, under the control of a suitable promoter, to prepare a nucleic acid construct.

Once the isolated nucleic acid molecule encoding the GLS protein has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

According to one embodiment, the GLS protein of the labeled GLS protein according to this aspect of the present invention is not a wild type protein but is mutant protein. For example, the GLS protein may be a human or mouse GAC or KGA protein as set forth above in SEQ ID NO:1, SEQ ID NO:3, SEQ ID NO:5, or SEQ ID NO:7, except that the protein has, for example, one or more amino acid substitutions, or one or more deletions or insertions. According to one embodiment, such a GLS protein mutant has an amino acid sequence that is at least about 80%, 85%, 90%, 91%, 92%, 93%, 94%, 95%, 96%, 97%, 98%, or 99% identical to SEQ ID NO:1, SEQ ID NO:3, SEQ ID NO:5, and/or SEQ ID NO:7, and has, for example, one or more amino acid substitutions, or one or more deletions or insertions.

According to another embodiment, the GLS protein is a mutant protein having an amino acid sequence comprising SEQ ID NO:9, SEQ ID NO:10, SEQ ID NO:11, or SEQ ID NO:12 (set forth infra), or a protein that is at least about 80%, 85%, 90%, 91%, 92%, 93%, 94%, 95%, 96%, 97%, 98%, or 99% identical to SEQ ID NO:9, SEQ ID NO:10, SEQ ID NO:11, and/or SEQ ID NO:12.

According to yet another embodiment, the GLS protein is a mutant protein having an amino acid sequence comprising three amino acid substitutions corresponding to K316E/D391K/R459E of mouse GAC protein (i.e., SEQ ID NO:3).

In one embodiment, the mutated GLS protein is a GLS monomer that is incapable of forming a GLS dimer. In other words, the mutation(s) stabilizes the GLS protein in a monomer form and prevents the mutated GLS protein from forming a dimer.

According to another embodiment, the GLS protein is a GLS protein or GLS protein fragment comprising the glutaminase domain pfam04960 of GLS as discussed infra. For example, according to one embodiment, the GLS protein is a protein or protein fragment comprising the pfam04960 domain of SEQ ID NO:18, as follows:

```
GKVADYIPQL AKFSPDLWGV SVCTVDGQRH SXGDTKVPFC LQSCVKPLKY AIAVNDLGTE   60
YVHRYVGKEP SGLRFNKLFL NEDDKPHNPM VNAGAIVVTS LIKQGVNNAE KFDYVMQFLN  120
KMAGNEYVGF SNATFQSERE SGDRNFAIGY YLKEKKCFPE GTDMVGILDF YFQLCSIEVT  180
CESASVMAAT LANGGFCPIT GERVLSPEAV RNTLSLMHSC GMYDFSGQFA FHVGLPAKSG  240
VAGGILLVVP NVMGMMCWSP PLDKMGNSVK GIHFCHDLVS LCNFHNY                287
```

In SEQ ID NO:18, amino acid residue X at position 32 is either I or T.

The labeled GLS protein of the present invention has a fluorescent reporter group attached to the GLS protein within the glutaminase domain pfam04960 of GLS. The glutaminase domain pfam04960 of GLS includes amino acid residues 73-550 of mouse GAC (SEQ ID NO:3) and mouse KGA (SEQ ID NO:7), and amino acid residues 73-545 of human GAC (SEQ ID NO:1) and human KGA (SEQ ID NO:5). Alternatively, the glutaminase domain pfam04960 of GLS is the consensus sequence of SEQ ID NO:18, set forth supra.

Attachment of the fluorescent reporter group to the GLS protein occurs, according to one embodiment, within the pfam04960 domain. For example, the fluorescent reporter group is, according to one embodiment, attached within amino acid residues 244-530 of human GAC protein (SEQ ID NO:1) and human KGA protein (SEQ ID NO:5), or within amino acid residues 249-535 of mouse GAC protein (SEQ ID NO:3) and mouse KGA protein (SEQ ID NO:7).

Suitable fluorescent reporter groups for carrying out this and other aspects of the present invention include a wide variety of fluorescent probes commonly used and widely available on the market. These fluorescent reporter groups could be any synthetic fluorophores that are either sensitive to their local environment, such as exhibiting a change in fluorescence in response to changes in immediate polarity, or sufficient reporter groups that produce fluorescence resonance energy transfer (FRET) between a donor fluorescent probe and an acceptor absorbant probe. Fluorescent reporter groups that are environamentally-sensitive can exhibit a change in fluorescence intensity, fluorescence life-time, or changes in their excitation or emission profiles. Environmentally sensitive fluorophores suitable for use in the present invention include, but are not limited to, derivatives of 7-aminocoumarin, fluorescein, rhodamine, pyrene, naphthalenes, dansyl chloride (5-dimethylaminonaphthalene-1-sulfonyl chloride), pyridyloxazole, dapoxyl, and nitrobenzoxadiazole (NBD). Common examples of these probes include, but are not limited to, fluorescent dyes from MOLECULAR PROBES® (Thermo Fisher Scientific, Inc.), such as the ALEXA FLUOR® series, DyLight FLUOR® series, rhodamine and/or fluorescein derivatives, Coumarin, Pacific Green™, Oregon Green®, Cy® 3, Pacific Orange™, Texas Red®, and Cy® 5.

These probes are attached to a GLS protein through direct covalent interaction with a native or mutated amino acid sidechain having a terminal amino or thiol reactive group (i.e., lysine and cysteine). The modification is performed by combining the GLS protein and the reporter group containing a reactive side-group together under conditions that allow reaction of the side-group attached to the reporter group with the GLS protein. The groups used to covalently attach reporter groups to amino or thiol weilding amino acids are widely available, and typically have a reactive side-group attached to the reporter group of choice that has a known reaction with amino or thiol groups. For amino group modification, these groups can include, but are not limited to, isothiocyanates, succinimydyl esters, sulfotetrafluorophenyl (STP) esters, tetrafluorophenol (TFP) esters, sulfodichlorophenol (SDP) esters, carbonyl azides, and sulfonyl chlorides. For thiol group modification, these groups include, but are not limited to, iodoacetamides, maleimides, 6-bromoacetyl-2-dimethylaminonaphthalene (badan), and acrylodan. These reactive groups can react with either native amino acids, or amino acids that have been inserted through molecular genetic approaches at a defined position.

According to one embodiment, the fluorescent reporter group is covalently attached to the GLS protein. In one embodiment, attachment of the fluorescent reporter group to the GLS protein is carried out by covalent modification of a native amino group presented by a lysine amino acid by a succinimidyl ester derivative of ALEXA FLUOR® 488 or QSY® 9 to form a stable amide-linked adduct comprising the reporter group and amino acid side chain.

Another aspect of the present invention relates to an isolated glutaminase (GLS) protein or protein fragment comprising a mutated glutaminase domain pfam04960 of SEQ ID NO:19, as follows:

```
GKVADYIPQL AKFSPDLWGV SVCTVDGQRH SXGDTKVPFC LQSCVKPLKY AIAVNDLGTE   60
YVHRYVGEEP SGLRFNKLFL NEDDKPHNPM VNAGAIVVTS LIKQGVNNAE KFDYVMQFLN  120
KMAGNEYVGF SNATFQSERE SGKRNFAIGY YLKEKKCFPE GTDMVGILDF YFQLCSIEVT  180
CESASVMAAT LANGGFCPIT GERVLSPEAV ENTLSLMHSC GMYDFSGQFA FHVGLPAKSG  240
VAGGILLVVP NVMGMMCWSP PLDKMGNSVK GIHFCHDLVS LCNFHNY                287
```

The residues identified above at positions 68 (E), 143 (K), and 211 (E) are mutated from the wildtype pfam04960 domain.

Specific isolated GLS protein mutants comprising a mutated glutaminase domain pfam04960 of SEQ ID NO:19 include, for example and without limitation, an amino acid sequence selected from the group consisting of SEQ ID NO:9, SEQ ID NO:10, SEQ ID NO:11, and SEQ ID NO:12 or a protein or protein fragment that is at least about 80%, 85%, 90%, 91%, 92%, 93%, 94%, 95%, 96%, 97%, 98%, or 99% identical to SEQ ID NO:9, SEQ ID NO:10, SEQ ID NO:11, and/or SEQ ID NO:12.

An alignment of SEQ ID NO:9 (mutated human KGA), SEQ ID NO:10 (mutated mouse KGA), SEQ ID NO:11 (mutated human GAC), and SEQ ID NO:12 (mutated mouse GAC) is set forth in FIG. 11. These isolated glutaminase protein mutants differ from SEQ ID NO:1, SEQ ID NO:3, SEQ ID NO:5, and SEQ ID NO:7, by a three amino acid substitution. Specifically, for SEQ ID NO:10, the mutated mouse KGA differs from SEQ ID NO:7 by the three amino acid substitution K316E/D391K/R459E. For SEQ ID NO:9, the mutated human KGA differs from SEQ ID NO:5 by the three amino acid substitution K311E/D386K/R454E. For SEQ ID NO:12, the mutated mouse GAC differs from SEQ ID NO:3 by the three amino acid substitution K316E/D391K/R459E. For SEQ ID NO:11, the mutated human GAC differs from SEQ ID NO:1 by the three amino acid substitution K311E/D386K/R454E.

As will be appreciated by a person of ordinary skill in the art, more than one nucleic acid coding sequence can encode for any one of the mutated GLS proteins of SEQ ID NO:9, SEQ ID NO:10, SEQ ID NO:11, and SEQ ID NO:12. Specifically, for every codon there are usually at least three different variations of possible nucleotide sequences. Non-limiting examples of cDNA coding for the mutated GLS proteins of SEQ ID NO:9, SEQ ID NO:10, SEQ ID NO:11, and SEQ ID NO:12 are set forth as follows.

One exemplary cDNA coding for the mutated human KGA of SEQ ID NO:9 is SEQ ID NO:14, as follows:

```
agtgcggagc cttaggcgga gcgaagagaa ccggtcgcgg caatcctagc gcgcagcagc    60
agcagcagca gcagcagcag cagcagcagc agcagcagca cccgcatccg ctgcgggagt   120
ccgagccgga accacaccca agtagctgcc ctttcctctt ctgtcatctc accgccccac   180
cacagaccgc gttccccgag gaaaccggcc gcccacgccc ggagcatcct cccctgttga   240
gcgggcgctg acggacccgg cggcatgatg cggctgcgag gctcggggat gctgcgggac   300
ctgctcctgc ggtcgcccgc cggcgtgagc gcgactctgc ggcgggcaca gcccttggtc   360
accctgtgcc ggcgtccccg aggcgggga cggccggccg cgggcccggc tgccgccgcg    420
cgactccacc cgtggtgggg cgggggcggc tggccggcgg agcccctcgc gcggggcctg   480
tccagctctc cttcggagat cttgcaggag ctgggcaagg ggagcacgca tccgcagccc   540
ggggtgtcgc cacccgctgc cccggcggcg cccggcccca aggacggccc cggggagacg   600
gacgcgtttg gcaacagcga gggcaaagag ctggtggcct caggtgaaaa taaaataaaa   660
cagggtctgt tacctagctt ggaagatttg ctgttctata caattgctga aggacaagag   720
aaaatacctg ttcataaatt tattacagca ctcaaatcta caggattgcg aacgtctgat   780
cccaggttga aagagtgtat ggatatgtta agattaactc ttcaaacaac atcagatggt   840
gtcatgctag acaaagatct tttaaaaaa tgtgttcaga gcaacattgt tttgttgaca    900
caagcattta gaagaaagtt tgtgattcct gactttatgt cttttacctc acacattgat   960
gagttatatg aaagtgctaa aaagcagtct ggaggaaagg ttgcagatta tattcctcaa  1020
ctggccaaat tcagtcccga tttgtggggt gtgtctgttt gtacagtaga tggacagagg  1080
cattctactg gagataccaa agttcccttc tgtcttcagt cctgtgtaaa acctttgaaa  1140
tatgccattg ctgttaatga tcttggaact gaatatgtgc atcgatatgt tggagaggag  1200
ccgagtggac taagattcaa caaactattt ttgaatgaag atgataaacc acataatcct  1260
atggtaaatg ctggagcaat tgttgtgact tcactaataa agcaaggagt aaataatgct  1320
```

-continued

```
gaaaaatttg actatgtcat gcagtttttg aataagatgg ctggtaatga atatgttgga  1380
ttcagtaatg caacgtttca gtctgaaaga gaaagtggaa agcgaaattt tgcaatagga  1440
tattacttaa aagaaaagaa gtgttttcca gaaggcacag acatggttgg tatattagac  1500
ttctacttcc agctgtgctc cattgaagtg acttgtgaat cagccagtgt gatggctgcg  1560
acactggcta atggtggttt ctgcccaatt actggtgaaa gagtactgag ccctgaagca  1620
gttgaaaata cattgagttt gatgcattcc tgtggcatgt atgacttctc agggcagttt  1680
gctttccatg ttggtcttcc tgcaaaatct ggagttgctg gggcattct  tttagttgtc  1740
cccaatgtta tgggtatgat gtgctggtct cctcctctgg ataagatggg caacagtgtt  1800
aagggaattc acttttgtca cgatcttgtt tctctgtgta atttccataa ctatgataat  1860
ttgagacact ttgcaaaaaa acttgatcct cgaagagaag gtggtgatca aagggtaaag  1920
tcagtgataa atcttttgtt tgctgcatat actggagatg tgtctgcact tcgaagattt  1980
gctttgtcag ctatggacat ggaacagcgg gactatgatt ctagaacagc actccatgta  2040
gctgctgcag agggtcatgt tgaagttgtt aaatttttgc tggaagcctg caaagtaaac  2100
cctttcccca aggacaggtg gaataacact cccatggatg aagcactgca ctttggacac  2160
catgatgtat ttaaaattct ccaagaatac caagtccagt acacacctca aggagattct  2220
gacaacggga aggaaaatca aaccgtccat aagaatcttg atggattgtt gtaatggtct  2280
caaatcccaa gatttaaatc acttacctat ttaattgtgg aaaatgatta tgaagaacat  2340
gtgtatttct atctggtagt gatgtatatt ttacatttgt catttcagtg ttactggagt  2400
tttcttcatt gtgcacacag gacaaatctg atctctttgg gaaaaaatag aaataaaaca  2460
atctccctcc ataatgtgag caatattacc tcgtgcattg tataatttga tgtaaaagaa  2520
atagttacca atgctagctt gtgtggtctt ccatgattta tttgtgtttt gtgaattttc  2580
aatttatggt gatgatctgc tgatatgcat ttataaagta agctctgttg tacagtctgt  2640
ccaaatgggt caaggttgcc tttagaagca aatagtgtga ttttcaagac ttcaaataca  2700
aatttagttt aagtgtttga acaactatat gcacttacgg ttgtgtgttt aaaatgtctc  2760
tctcaccccc tagcttcatg atgtgactct taaaaaacta taatagttaa caactgttag  2820
```

One exemplary cDNA coding for the mutated human GAC of SEQ ID NO:11 is SEQ ID NO:15, as follows:

```
agtgcggagc cttaggcgga gcgaagagaa ccggtcgcgg caatcctagc gcgcagcagc    60
agcagcagca gcagcagcag cagcagcagc agcagcagca cccgcatccg ctgcgggagt   120
ccgagccgga accacaccca agtagctgcc ctttcctctt ctgtcatctc accgccccac   180
cacagaccgc gttccccgag gaaaccggcc gcccacgccc ggagcatcct cccctgttga   240
gcgggcgctg acggacccgg cggcatgatg cggctgcgag gctcggggat gctgcgggac   300
ctgctcctgc ggtcgcccgc cggcgtgagc gcgactctgc ggcgggcaca gcccttggtc   360
accctgtgcc ggcgtccccg aggcggggga cggccggccg cgggcccggc tgccgccgcg   420
cgactccacc cgtggtgggg cgggggcggc tggccggcgg agcccctcgc gcggggcctg   480
tccagctctc cttcggagat cttgcaggag ctgggcaagg ggagcacgca tccgcagccc   540
ggggtgtcgc cacccgctgc cccggcggcg cccggcccca aggacggccc cggggagacg   600
gacgcgtttg gcaacagcga gggcaaagag ctggtggcct caggtgaaaa taaaataaaa   660
cagggtctgt tacctagctt ggaagatttg ctgttctata caattgctga aggacaagag   720
aaaataccctg ttcataaatt tattacagca ctcaaatcta caggattgcg aacgtctgat   780
```

-continued

```
cccaggttga aagagtgtat ggatatgtta agattaactc ttcaaacaac atcagatggt   840
gtcatgctag acaaagatct ttttaaaaaa tgtgttcaga gcaacattgt tttgttgaca   900
caagcattta gaagaaagtt tgtgattcct gactttatgt cttttacctc acacattgat   960
gagttatatg aaagtgctaa aaagcagtct ggaggaaagg ttgcagatta tattcctcaa  1020
ctggccaaat tcagtcccga tttgtggggt gtgtctgttt gtacagtaga tggacagagg  1080
cattctactg gagataccaa agttcccttc tgtcttcagt cctgtgtaaa acctttgaaa  1140
tatgccattg ctgttaatga tcttggaact gaatatgtgc atcgatatgt tggaaaagag  1200
ccgagtggac taagattcaa caaactattt ttgaatgaag atgataaacc acataatcct  1260
atggtaaatg ctggagcaat tgttgtgact tcactaataa agcaaggagt aaataatgct  1320
gaaaaatttg actatgtcat gcagtttttg aataagatgg ctggtaatga atatgttgga  1380
ttcagtaatg caacgtttca gtctgaaaga gaaagtggaa agcgaaattt tgcaatagga  1440
tattacttaa aagaaaagaa gtgttttcca gaaggcacag acatggttgg tatattagac  1500
ttctacttcc agctgtgctc cattgaagtg acttgtgaat cagccagtgt gatggctgcg  1560
acactggcta atggtggttt ctgcccaatt actggtgaaa gagtactgag ccctgaagca  1620
gttgaaaata cattgagttt gatgcattcc tgtggcatgt atgacttctc agggcagttt  1680
gctttccatg ttggtcttcc tgcaaaatct ggagttgctg gggcattct tttagttgtc  1740
cccaatgtta tgggtatgat gtgctggtct cctcctctgg ataagatggg caacagtgtt  1800
aagggaattc acttttgtca cgatcttgtt tctctgtgta atttccataa ctatgataat  1860
ttgagacact ttgcaaaaaa acttgatcct cgaagagaag gtggtgatca aaggcattcc  1920
tttggaccat tggactatga aagtctccaa caagaacttg ctttaaaaga gacagtatgg  1980
aaaaaagtgt cacctgagtc aaatgaggac atctctacaa ctgtagtata tagaatggaa  2040
agtctgggag agaaaagcta aagaaatggg ttctagtttc agaatgtttc ttcatttaat  2100
ctttcaaaca tctttagctt ttttttgcaa gttataaata tttatttgag gtattttttg  2160
ttctcaatct tgggtgctgg agccataaag cttttttttc cttttaatct ttgtataaag  2220
gcagtagatt aagaagtgca tttgttggtc tttaaaaagt atttacaagt acataaattt  2280
gctttatttt taaaaataca aaaaggaaaa atttaaattt tttttgatgt aattaaaatg  2340
ttaactatgt ggtcagataa tcccatttta caatagtaac agaaaattgt aattcttagt  2400
tctaaaattc acaaattaaa ctcataagtt ttgttgcatt ttgtttttttc ttttccattt  2460
ttaaaactaa tgtgatgtct ttagtggcaa tagaaggtac ttctatgcta aatacaaaac  2520
taaaaaggca aaataatgaa ccccaaatta ttttatttaa aatagcagtg gattataaaa  2580
ttagcttgtg tttacattta tgccattttt ggtgatagat tggctttaca ttttaaaaaa  2640
tttatttaaa aatttatcaa atgctttaaa atatgactcc tactttttttt attttgcaac  2700
tcctctgttc tgtcagagtt gttatataca ggagtgtctt atgttactaa aacattccag  2760
ccaaagaatt tcagatgtga gataatgatg tttcatcaat aaaaagctat aatggttagt  2820
tactcagaag gagaaacagt gagtgtcttc aagtgaattg ttcacctaaa caattttatt  2880
ttcatattat ccacataact ttttctatgt tatatttaaa tatgaatggc aaattttggt  2940
ttttagcttt tacattttat tatcttaatt tttataaatgc taatatttct tttgtgataa  3000
gttatagcat ctcataaagt ttgttctatt tgaagttttt tagagtactt gagaaatgaa  3060
tttagtctgc aggtagtaag tatgctacta aaatacgtta gatctaaatc cttttatttg  3120
gtataaaaat gcaatattga gaatcaaaac ttgtttttaa gagaactata gattctacac  3180
aacctgattt caagtaatta ttcatagtat ttatagttgt cttggcaaag tgattgtaaa  3240
```

-continued

```
attctgtagg acctattcac acttcttcct tcttccatat acttctctgg ttttccccat  3300
agttccccta taatttcaag tttgttgaaa cctgttaatt ttagtggggg attagaagaa  3360
aaacttggtg gtttcttagc atgatggtgt atgtatgtgg taatggaaag tctgtaaaag  3420
taaatatagt gtagcaaaaa agatttcact gagtatttta gatactagtg caaataaaga  3480
tagaaaatct tgatcataat gtcttaagtt tgggaactgt gatattaaga aaagaaattc  3540
ccttctagag gtgctggcca aaaagccttt tgggctaact taagtattaa atttatatat  3600
ttaaataatt atattttaag ttgtagagga ttttcccaag gattttatgc ttacttgaat  3660
gttctttgaa tgttcagatg catatcctaa ctggatgctt ctcaaggcct tactgcatat  3720
ttgtgttgca tatttatgtt agttgcacca gggccatttg tagtttgggc aaccgaatgc  3780
cttaattgga aaaaaggcat tgtggtttcc cctatgatct aaattgttac attttaccat  3840
ttcattccga agttggtttt actttattaa atgaagattt agttttcata tcgtatacat  3900
agctgtatag atttcaaaat taggttgtta atttgtgtca cttactattt ttgtgttggt  3960
aatgctttaa atgcatactt aaaaatgaag tactgttatc taagctactg tgtttagaaa  4020
atgttaagaa tgagcagaaa tttttataga aaagtataaa cggaagaaga gataagatac  4080
tgcgaatagg ccctcaaact taaaaaagaa aaaactttgc cagttttaag gacatatttt  4140
gattctttca gtattcttaa caccttttta aacaaagttc ttgatagtac ccactattat  4200
tgggtttgtt ttatgccatt attgattctt gatattcaag catttacaat gtagcatatt  4260
tgattttctt ttttctttct ttttttggca tcattaacat ttcatttgaa atgcatattg  4320
ttcttgaagt actttgtttt tagcataaat gttgtgcatt ttatcttagt gtttggatga  4380
aaacatttgt gttgtttagc tttcatttgc tttgtatatt taataatgta cctttatttt  4440
ccagtatgcc tacattttgt attgcacaat aaatttattt taagctgaaa aaaaaaaaaa  4500
aaaaaaaaa                                                          4509
```

One exemplary cDNA coding for the mutated mouse KGA of SEQ ID NO:10 is SEQ ID NO:16, as follows:

```
tgagcgtcag tctcagtgcg gagctcgcgg cggccagagc aacttcggct ggctgcaggc    60
tgggcggcgg cggcggcgag ggcggcggcg ttggcggcgg gagcggcgga gctggggcca   120
caccccgtcc cggacttttt ctctttccag tcctctcccc gccgtgcggg acacggttcc   180
gggagcagag cggccgccca cgccccaagc atcctcatct gacgagcggg cgccggcggt   240
atgatgcggc tgcgaggctc ggcgatgcta cgggagctgc tcttaaggcc gcccgccgcc   300
gtcggagccg tcctgcggcg cgcgcagccc ctcggcacgc tgtgccggcg cccccggggc   360
gggagccggc cgaccgctgg cctggtggcc gctgcgcgac tccacccgtg gtggggcggg   420
ggcggccgcg cgaagggccc cggcgcgggc ggcctgtcca gttcgccctc ggagatccta   480
caggagctgg ggaagggggg tacgccgcca cagcagcagc agcagcagca gcagcagcca   540
ggggcgtcgc cacccgcagc cccgggcccc aaggacagcc cgggggagac cgacgcgttc   600
ggcaacagcg agggcaagga gatggtggcc gcgggcgaca ataaaataaa acagggtctg   660
ttacctagct tggaagattt gctgttctat acaattgcag aaggacaaga aaagatacct   720
gttcacaagt ttattacagc actcaaatct acaggattgc gaacatctga tcccaggttg   780
aaagagtgta tggatatgtt aagattaact cttcagacaa cgtcagatgg tgtcatgcta   840
gacaaagatc tttttaaaaa gtgtgttcaa agcaacattg ttttgttgac acaagcattt   900
agaagaaagt ttgtcattcc tgactttatg tcttttacct cacacatcga tgagttatat   960
```

-continued

```
gaaagtgcta aaaagcagtc tggagggaag gttgctgatt atattcctca gctggccaaa  1020
ttcagtcctg atttgtgggg tgtatctgtc tgtactgtag atgggcaaag gcattctatt  1080
ggagatacca aagttccttt ttgtcttcag tcctgtgtaa aacccctgaa atatgcaatt  1140
gctgttaatg acctgggaac tgagtatgta catcgctatg ttggggagga gccaagtgga  1200
ttaagattca acaaactctt tttgaatgaa gatgataaac cacataatcc tatggtaaat  1260
gctggagcaa ttgttgtgac ttctctaata aagcaaggag taaataatgc tgagaagttt  1320
gactacgtga tgcaattttt gaataagatg gctggtaatg aatatgttgg attcagtaat  1380
gcaacgtttc agtctgaacg agaaagtgga aagcgaaatt ttgcaatagg atattactta  1440
aaagaaaaga agtgttttcc agaaggcaca gacatggttg ggatactaga tttttacttc  1500
cagctgtgct ctattgaagt gacatgtgaa tcagcaagtg tgatggctgc caccttggct  1560
aatggtggtt tctgcccaat tactggtgaa agagtcctca gtcctgaggc agttgaaaat  1620
acactgagct tgatgcattc ttgtggcatg tatgacttct cagggcagtt tgcgttccat  1680
gttggtcttc ctgcaaaatc tggagttgct gggggtattc ttttagttgt ccccaacgtc  1740
atgggcatga tgtgttggtc tcctcctctt gacaagatgg gcaacagtgt taagggaatt  1800
cacttttgtc acgatcttgt ttctctgtgt aacttccata actatgataa tttgagacac  1860
tttgcaaaaa aacttgatcc tcggagagaa ggaggtgatc aaagggtgaa gtcggtgata  1920
aaccttctgt ttgccgcata cactggagat gtgtctgccc tccgaaggtt tgctctgtca  1980
gccatggaca tggagcagcg ggattatgac tccagaacag ccctccatgt cgcagcagca  2040
gagggtcatg ttgaagttgt caagtttttg ctggaagctt gcaaagtaaa ccctttcccc  2100
aaggacaggt ggaataatac ccccatggat gaagcactac actttggaca ccatgatgtt  2160
tttaaaatcc ttcaggaata ccaagttcag tacacacctc aaggggattc tgatgatgga  2220
aagggaaacc agactgtcca caagaatctc gacgggttgc tataatggtc tgcaccccaa  2280
gacttccatt acttacctag tcattgtgga acatgactat ggagagcatt gtatatttct  2340
atctggtagt aatgtgtatt tacaacatct gtcactgcag tgttaccgga gcttccttca  2400
ttgtgcgcac acgacaaatc tgagttcttt gggaaaaaaa tagaaatgaa gcagcctccc  2460
ttcataatgt gagcaatagt tacctcgtgc attgtacaat gtggtgtaaa agagtagtta  2520
ccaatgccag ctgaactgtg tggtcttcat ggtttgcgtt ctgtacattt tcaagccctg  2580
gtgatgatac gctcatatgc acttaggagt gagctttgtt gtacagtctg tccacggggt  2640
cgatgctgtt attaggtgaa aatagtgtga tctttaagac tttaaataca gatttagttt  2700
tgagtgtttg agagaccact acacttgtat ggttgagtgt ttaaaatgtc tatcaccctc  2760
acttcagagt gtgactcttt aaatattaaa atagatacta actgttcata gaacaggccg  2820
attctgatta gattttatca gggaatctgt taagatatgt ttggtgacca aaacgtatgt  2880
gtgaatatag ttctagcact tttaaatttt tcctttccat acaacgcttg ggccagcctc  2940
tctgtgctgc gtggctgtcg gtccccctca gctgggaaag agagcactgg ctcactgtgc  3000
agttttcatg tttcctcagc aagccatcaa gcctcacatc tctaccatca gagatagagc  3060
ttggccattt atctaaggaa gatgagccaa aattatgaca tctaaaataa tcgtcagtct  3120
taagagtaaa gacagcgaaa ctgcacactt ataagttctt ttcagcttct acaataaaga  3180
aaagttcaga aatgctttca gttaccaaag ttataacgat atatttagga aaagctacaa  3240
ataacactta ctttgaatcc tgctgtcaaa tgtctgcatc aagatagcac ccctttgtgg  3300
gaggccctga gtatcttctc ttcctctact gcctaactgt tggtgggctg tatcattcaa  3360
taagatcact tcattttcaa cttagaccca ccgtttcttt tttgttgttt tgttttgttt  3420
```

-continued

```
ggtttggttt ggttgggttg ggttgttgtt tttggttttt tcgagacagg gtttctctgt  3480
gtagccctgg ctgtcctgga actcactttg tagaccaggc tggccttgaa ctcagaaatc  3540
cgcctgcctc tgcctcccga gtgctgggat taaaggtgca aactaccacg cctggcagac  3600
ccaccatttc tttgctttgg aaaggtaatt tatgattaac ttagataata ggtaaaagcg  3660
accttacaaa aaacataatt atctaggagt cccacatact ggacctaccc tattatacct  3720
ccaagagata aagggtatgt tagtgaggac ttttgcacac aagtgcatgc acacttggca  3780
tacacacaca cacacacaca cacacacaca cacacacaca cacacggact tcttggaaac  3840
tgctttatga agaaactgct ttatgaaata agcaaaattc tcaagtgcac agatactagc  3900
agttatgaca gtaatacagc gtcttctgtg accctcacta cctgcactgc ttgcatccct  3960
gctttatgcc tggtggcaca ttattcaccc ggtaacctcc agctgctttg atcctgtttc  4020
agtcaaagtc agcttcagcc accccctcca ttccctagcc agctccaccc ttgatgaaac  4080
tgtggctaat gttccttcac taggacaggc accatgagtg tgtttctaag ttccagagtc  4140
tgtggggagg atggtgggtg ggcagccagc cctgttgcta tgttgcttct tccacacccc  4200
ctcaagacag gtgcataggt ggcactggga acatcctacg cagggacaac ctccaaaatt  4260
aatgggtgaa catggttttt ttggaatcaa ctgagataat gctatttcaa tagcggctgg  4320
ctttttgtga ttcagtaact taaatattgc cagtgactga ggatcccctc cagtcatggt  4380
tctgtatatt ctttgagaca ggtgttttca tcttctctca gctcagtgct gttttgtaca  4440
gtctctgtgg cttggttgag tatgctcttt cctgtgccag gtcttgctct ggctgttcgc  4500
tactggctga taataacaag gaccctgtgt gtgtgtgaat gagccgctaa ctgctaccat  4560
ctgtaaactc caaagatctg tttgttttgg ctttacaatc ttagctaatt tttctgtatc  4620
ctggaaccat tacatgatca tgttgctttg aagatctttt tatgccactg tttctgctgt  4680
cttggttctg acacccctgt ctggtgatat gctataccoc agtgctgcct acacgtgctt  4740
tagctgtaga gctgggtata ctgttgatcc agctgtccgt cagggacttg ataacctgat  4800
gtttgatgta gatccctgct ggggagtcca caactatgaa tgtatttact tccaacattt  4860
cccaaaatga aaactataaa ttgcaagtat tctggaattg ggaaatactt attttaaatg  4920
agatcaggta gtgttgcttt ttacagcata ataaatatgt gtattgaaaa caaa        4974
```

One exemplary cDNA coding for the mutated mouse GAC of SEQ ID NO:12 is SEQ ID NO:17, as follows:

```
tgagcgtcag tctcagtgcg gagctcgcgg cggccagagc aacttcggct ggctgcaggc    60
tgggcggcgg cggcggcgag ggcggcggcg ttggcggcgg gagcggcgga gctggggcca   120
caccccgtcc cggacttttt ctctttccag tcctctcccc gccgtgcggg acacggttcc   180
gggagcagag cggccgccca cgccccaagc atcctcatct gacgagcggg cgccggcggt   240
atgatgcggc tgcgaggctc ggcgatgcta cgggagctgc tcttaaggcc gcccgccgcc   300
gtcggagccg tcctgcggcg cgcgcagccc ctcggcacgc tgtgccggcg cccccggggc   360
gggagccggc cgaccgctgg cctggtggcc gctgcgcgac tccacccgtg gtggggcggg   420
ggcggccgcg cgaagggccc cggcgcgggc ggcctgtcca gttcgccctc ggagatccta   480
caggagctgg ggaagggggg tacgccgcca cagcagcagc agcagcagca gcagcagcca   540
ggggcgtcgc cacccgcagc cccgggcccc aaggacagcc cgggggagac cgacgcgttc   600
ggcaacagcg agggcaagga gatggtggcc gcgggcgaca ataaaataaa acagggtctg   660
ttacctagct tggaagattt gctgttctat acaattgcag aaggacaaga aaagatacct   720
```

-continued

```
gttcacaagt ttattacagc actcaaatct acaggattgc gaacatctga tcccaggttg   780
aaagagtgta tggatatgtt aagattaact cttcagacaa cgtcagatgg tgtcatgcta   840
gacaaagatc tttttaaaaa gtgtgttcaa agcaacattg ttttgttgac acaagcattt   900
agaagaaagt ttgtcattcc tgactttatg tcttttacct cacacatcga tgagttatat   960
gaaagtgcta aaaagcagtc tggagggaag gttgctgatt atattcctca gctggccaaa  1020
ttcagtcctg atttgtgggg tgtatctgtc tgtactgtag atgggcaaag gcattctatt  1080
ggagatacca aagttccttt ttgtcttcag tcctgtgtaa aacccctgaa atatgcaatt  1140
gctgttaatg acctgggaac tgagtatgta catcgctatg ttggggagga gccaagtgga  1200
ttaagattca acaaactctt tttgaatgaa gatgataaac cacataatcc tatggtaaat  1260
gctggagcaa ttgttgtgac ttctctaata aagcaaggag taaataatgc tgagaagttt  1320
gactacgtga tgcaattttt gaataagatg gctggtaatg aatatgttgg attcagtaat  1380
gcaacgtttc agtctgaacg agaaagtgga aagcgaaatt ttgcaatagg atattactta  1440
aaagaaaaga agtgttttcc agaaggcaca gacatggttg ggatactaga tttttacttc  1500
cagctgtgct ctattgaagt gacatgtgaa tcagcaagtg tgatggctgc caccttggct  1560
aatggtggtt tctgcccaat tactggtgaa agagtcctca gtcctgaggc agttgaaaat  1620
acactgagct tgatgcattc ttgtggcatg tatgacttct cagggcagtt tgcgttccat  1680
gttggtcttc ctgcaaaatc tggagttgct gggggtattc ttttagttgt ccccaacgtc  1740
atgggcatga tgtgttggtc tcctcctctt gacaagatgg gcaacagtgt taagggaatt  1800
cacttttgtc acgatcttgt ttctctgtgt aacttccata actatgataa tttgagacac  1860
tttgcaaaaa aacttgatcc tcggagagaa ggaggtgatc aaaggcattc ctttggacca  1920
ttggactatg agagtctcca gcaagaactt gctttaaaag acacagtatg gaaaaaagtg  1980
tcacctgagt caagtgacga cacctctaca actgtagtat atagaatgga gagtctgggg  2040
gagaggagct agagatgggc tctagctaca gaacagaacg attctccttt taacatcgga  2100
aacatcttta ggcttttgtt tcttgtttat ctttccaaac taagtattta ttcaagtatt  2160
ctattgttat cagttttggg tactggagcc ataaatttaa aaaaaggttc tgtttttggtt  2220
tggttttttt tcgcttgtaa tctttgtata aaaaacattt gttatttttt aaaagagcat  2280
ttacaaataa agcaaatttg ctttattttt taaaactttt ttaaaaaatg caatttcctt  2340
aattacatta aaaatttaac tataaaattt ggtaaccaca ttgtttttct tagttctgaa  2400
gcctgcatat taaactgagg cgtattgttg gatttgtctt ttcctttcca gttttataat  2460
tgataggcta tattggtagt gacagaaagt acttccatgc taaatataaa actaaaaagg  2520
caaagtaatc aaaattattt aaaagagtac tagattataa aattagcttt agtttacaca  2580
tatgccagtt atagcggtag attggctttg aatatttaaa atgcaaatac ttttaaatat  2640
gtcttttttt ttgtttgaaa agttctgtcc tgtcagaatc acaatgtatt aggaatgttt  2700
cacatcactg aaacactcca gccaaagaat tgcagatgtg tgagaatggc atgccctgtt  2760
atttaaaagc tacaatggtt agttgctcag aaaaagagtc aataactatc ttcaaaatgg  2820
attgtatttt catattcttc atgtaatttt tttgttgtat ttaagtatga acggtaaatt  2880
ttgctttttt agcttttagt aattttatta tgtttcataa gtgctaatga atattttgtg  2940
ataattataa catctcataa attttgttct ttttgaactt ttattagcat acttatgaaa  3000
tgaatatagt ttgaaggtgt taagtataca actaaaatat ttgttgaatt ggaatgcttc  3060
tgtttatttt taaaatgcaa tattgagaat caaaactttt ttcaagagaa tcataggttc  3120
cattttatct cgtcataaac agatatacat atttttagaa tctatcttgg caaaatgata  3180
```

-continued

```
ctaatgttct gcaggattta tttacatgtc ttccttcgtg tattttgttt ttctcacaat  3240

ttcaagtttg gtttttcaaa ttcactttta aacttgtaaa ttttgggcaa gtggttgaga  3300

atgaaagcct tattgctttt taaattatgg cacatgtata gtagagcaga ttctgtaact  3360

aaagaaagtg cgggaaaaat agttcactga taggctaagt aagatacagg aaagtcctga  3420

tggtctgatt tgaaactggg aactctgata ttaagaaaag ggttcttctc agaagttcga  3480

ccttaaagcc tttgggctaa cttaagtatt actatttgta tttaaataat tacatggtgg  3540

gttttagaaa ggctggctgt cctgcccctt tggtgttcat atgcattccc cagcctgatg  3600

ctttaaaagc cttgccactg ccctgcttgt ggacactaat catctctttt tcttgtatcc  3660

agagtgactg tgattcaggt aattgagcac catgattgga aaaaagattt taggtttatt  3720

tcccctccat ttttatgtgt acattttgtt gtttcattca gaagttggat ttactttaca  3780

aaatgactta attttcatat tgtggtcatg tttgtgtaaa cttcaaacta ttttgttaat  3840

ttttggcact tcctatatat aattctagta atgcttgaat gtacacttaa atatgaagta  3900

ggattaagtc agctgctgtg tttaaagaat gctgttaaga acaagcattc aaaactgtat  3960

aggaaggtat tagcttaaga gtaggtaaga taccgtgact gtatctgcag acaagaagag  4020

gaaagaaaag ctttgccagt ttgtggattt atcttaattc ccttcagtat attcaatctc  4080

ttttcaaata aagctctttg agaagtaccc agtattgttg ggtttaattt ttcctactat  4140

tattgattct tgatattcaa gcatttacat gacagcgtat ttttttcttt tcctttttttc  4200

tgtttatttt tttttgctat cattaacatt tcatttgaaa tgcatactct tcttgaaata  4260

ttttgttttt agcataaatg ttgtgcattt tatcttagtg tttggattaa aacatttgtg  4320

ttgttgagct ttcttcattt gctttgtata tttaataatg tatctttatt ttccagtatg  4380

cctatttttt gtattgtaca ataaatttat tttaagctg                          4419
```

A further aspect of the present invention relates to a method of screening for compounds that allosterically bind to a glutaminase (GLS) protein. This method involves providing the labeled GLS protein of the present invention under conditions effective for the fluorescent reporter group attached to the GLS protein to produce fluorescence at a first level. The labeled GLS protein is contacted with a candidate compound. Candidate compounds where said contacting causes the fluorescent reporter group to emit fluorescence at a level above or below the first level are identified as being compounds capable of allosteric binding to the GLS protein.

In carrying out this and other aspects of the present invention, providing the labeled GLS protein can be accomplished as described supra. In addition, the GLS protein used in this and other aspects of the present invention is as described supra.

This method of the present invention may be carried out in a cell, but is not necessarily carried out in a cell. When carried out in a cell, the GLS protein may be recombinantly expressed, as described supra, and the fluorescent reporter is attached to the GLS protein as described supra to provide the labeled GLS protein.

The labeled GLS protein, by its fluorescent label, emits fluorescence at first level (e.g., a particular wavelength or intensity associated with the fluorescent reporter group). A candidate compound is a compound that causes the fluorescent reporter group to emit a fluorescence at a level above or below the first level, or causes a detectable change in fluorescence (e.g., a shift in the fluorescence wavelength or intensity, or a change in fluorescence lifetime) of the fluorescent reporter group. Detecting a change in fluorescence in this and other aspects of the present invention may be carried out by visual observation. Alternatively, detecting a change in fluorescence may be carried out with a spectrophotometer, or a microscope or macroscope system coupled to a camera or photomultiplier tube. Coupled with proper instrumentation, the optical readout can be followed in real time to obtain spatio-temporal information (functional intracellular imaging).

According to this aspect of the present invention, the GLS protein is, according to one embodiment, a monomer. According to an alternative embodiment, the GLS protein is a dimer.

Figure 6A:
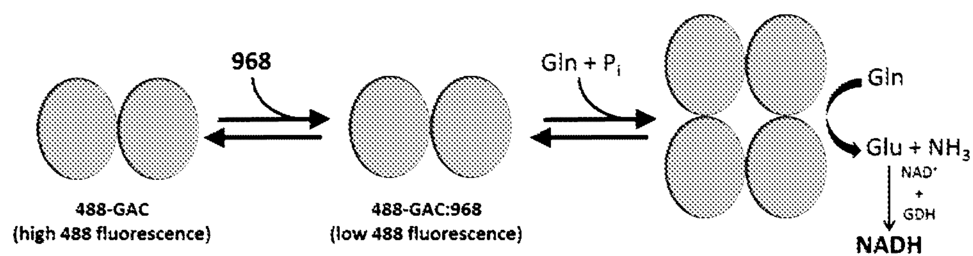
FIGS. 6A-F illustrate coupling real time drug binding with enzymatic activity.

One embodiment of this method of the present invention is illustrated in FIG. 6A. On the left side of the schematic illustration of FIG. 6A, a GLS protein dimer is shown to be labeled with ALEXA FLUOR® 488 succinimidyl ester ("488-GAC"). This GLS protein dimer emits a high fluorescence. When contacted with candidate compound 968, 488-GAC emits a low fluorescence. In other words, candidate compound 968 binds the GLS protein and causes the fluorescent reporter group ALEXA FLUOR® 488 attached to the GLS protein to emit a fluorescence at a level below the first level (i.e., the level of fluorescence emitted by 488-GAC in the absence of contact with candidate compound 968).

The method according to this aspect of the present invention may further involve contacting the GLS protein, after identifying candidate compounds, with glutamine under conditions effective to activate the GLS protein. NADH is detected following the contacting with the GLS protein, after said identifying with glutamine. Candidate compounds (1) where NADH is detected are identified as being compounds that do not inhibit GLS protein activity and (2) where NADH is not detected are identified as being compounds that do inhibit GLS protein activity. This embodiment is also illustrated in FIG. 6A, where 488-GAC:968, i.e., the labeled GLS protein bound by a candidate compound is contacted with glutamine (Gln+$P_i$) under conditions to activate the GLS protein to form a GLS protein tetramer (illustrated in the right side of the schematic in FIG. 6A). The tetramer form of the GLS protein catalyzes the reaction of glutamine to NADH, as illustrated in FIG. 6A. Thus, the detection of NADH in carrying out this method of the present invention is indicative of the candidate compound not inhibiting GLS protein activity (despite binding GLS protein). Where NADH is not detected, the candidate compound is identified as a GLS protein activity inhibitor.

Yet another aspect of the present invention relates to a method of identifying compounds that inhibit or stabilize tetramer formation of glutaminase (GLS) protein. This method involves providing a first labeled GLS dimer protein comprising a GLS protein and a fluorescent donor attached to the GLS dimer protein. A second labeled GLS dimer protein comprising a GLS protein and a fluorescent acceptor attached to the GLS protein is also provided, where binding of the first labeled GLS protein and the second labeled GLS protein forms a GLS protein tetramer and results in an interaction between the fluorescent donor and the fluorescent acceptor which produces a fluorescence resonance energy transfer at a first level. The first labeled GLS dimer protein and the second labeled GLS dimer protein are contacted under conditions effective for the first labeled GLS dimer protein and the second labeled GLS dimer protein to bind and form a GLS protein tetramer. The GLS protein tetramer is contacted with a candidate compound. The method further involves detecting whether said contacting with the candidate compound alters the fluorescence resonance energy transfer at the first level. Detection of the fluorescence resonance energy transfer at the first level indicates that the candidate compound neither inhibits nor stabilizes GLS protein tetramer formation and detection of the fluorescence resonance energy transfer at a level above or below the first level indicates that the candidate compound inhibits or stabilizes tetramer formation of GLS protein.

According to the method of this aspect of the present invention, the first and second GLS proteins are wild type proteins. According to one embodiment, the first and second proteins are GLS isoforms selected from GAC and KGA. Preferably, the first and second proteins are a single GLS isoform, e.g., the first and second proteins are both GAC or the first and second proteins are both KGA.

In carrying out this method of the present invention, the GLS dimer proteins may be labeled with labels discussed supra. However, in carrying out this method, the labels are capable of forming FRET pairs, where fluorescence energy from a fluorescent donor probe can be transferred to an absorbant but not necessarily fluorescent accepter probe (e.g., non-fluorescent QSY dyes available from MOLECULAR PROBES® (Thermo Fisher Scientific, Inc.)). Any FRET pair is suitable for this method of the present invention involving the readout of inhibition or stabilization of GLS protein tetramer formation. In one specific embodiment, the fluorescent donor is ALEXA FLUOR® 488 succinimidyl ester and the fluorescent acceptor is QSY® 9 succinimidyl ester, both of which are MOLECULAR PROBES® obtainable from Thermo Fisher Scientific, Inc. Other donors and acceptors are well known and can also be used.

One embodiment of this method of the present invention is illustrated in the schematic diagram of FIG. 1A. As illustrated on the left side of the schematic in FIG. 1A, a first labeled GLS dimer protein is provided comprising a GLS protein and a fluorescent donor attached to the GLS dimer protein. Specifically, the GLS dimer protein is isoform GAC labeled with ALEXA FLUOR® 488 succinimidyl ester ("488-GAC"). This first labeled GLS dimer protein is a high fluorescence donor protein. A second labeled GLS dimer protein comprising a GLS protein and a fluorescent acceptor attached to the GLS protein is also provided, as illustrated in FIG. 1A by the dimer labeled "QSY9-GAC." Specifically, this dimer protein is the GLS isoform GAC labeled with the fluorescence acceptor QSY® 9 succinimidyl ester. As illustrated on the right side of the schematic of FIG. 1A, binding of the first labeled GLS protein (i.e., 488-GAC) and the second labeled GLS protein (i.e., QSY9-GAC) forms a GLS protein tetramer and results in an interaction between the fluorescent donor (ALEXA FLUOR® 488 succinimidyl ester) and the fluorescence acceptor (QSY® 9 succinimidyl ester) to produce a fluorescence resonance energy transfer at a first level ("FRET" in FIG. 1A). This FRET scenario is then used to identify compounds that inhibit or stabilize tetramer formation of glutaminase (GLS) protein according to the method of this aspect of the present invention.

Specifically, the first labeled GLS dimer protein (i.e., 488-GAC) and the second labeled GLS dimer protein (i.e., QSY9-GAC) are contacted (e.g., brought into contact with each other) under conditions effective for the first labeled GLS dimer protein and the second labeled GLS dimer protein to bind and form a GLS protein tetramer, as illustrated in FIG. 1A. The GLS protein tetramer may then be contacted with a candidate compound. The method further involves detecting whether said contacting with the candidate compound alters the fluorescence resonance energy transfer at the first level. In other words, in the absence of a candidate compound, the FRET pair experiences a fluorescence resonance energy transfer at a particular level determined by the donor and acceptor. If, after coming into contact with a candidate compound, the fluorescence resonance energy transfer is unaltered, the candidate compound is determined to neither inhibit nor stabilize GLS protein tetramer formation. If, on the other hand, the fluorescence resonance energy transfer is altered (e.g., is above or below the fluorescence resonance energy transfer of the tetramer in the absence of the candidate compound), then the candidate compound is determined to inhibit or stabilize tetramer formation of GLS protein.

In one embodiment, this method of the present invention is carried out with a population of dimer proteins comprising donors and a population of dimer proteins comprising acceptors. Under certain conditions, about one-half of the dimers will form tetramers to produce a fluorescence resonance energy transfer (e.g., will establish an equilibrium of dimers:tetramers). In carrying out the method according to this aspect of the present invention, the population of dimers:tetramers is contacted with a candidate compound. A candidate compound capable of stabilizing tetramer formation of GLS protein will cause a shift in the equilibrium of dimers:tetramers to increase the number of tetramers formed and, thereby, alter the detectable level of fluorescence energy transfer. Alternatively, a candidate compound capable of inhibiting tetramer formation of GLS protein will cause a shift in the equilibrium of dimers:tetramers in the opposite direction to decrease the number of tetramers formed and, thereby, alter the detectable level of fluorescence energy transfer.

Figure 5A:
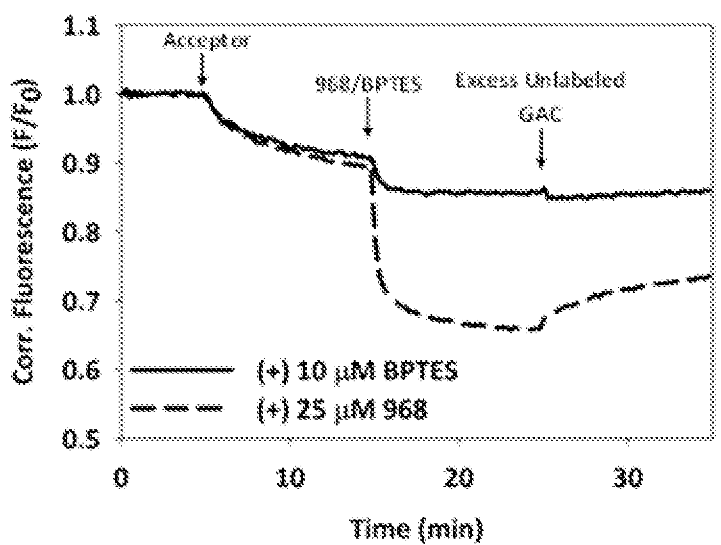
FIGS. 5A-C illustrate that the effects of allosteric inhibitors BPTES and 968 on tetramer formation leads to direct binding read out of 968 and 488-GAC.

This phenomenon is illustrated in FIG. 5A, in the line representing (+) 10 μM BPTES. Specifically, beginning at the left of the graph, a GLS dimer protein labeled with a donor group emits a fluorescence that is quenched upon coming into contact with a GLS dimer protein labeled with an acceptor group ("Acceptor"). This quenching in fluorescence upon contact between the donor and acceptor occurs as the fluorescence of the donor is absorbed by the acceptor. Upon contact with a candidate compound ("968/BPTES"), further quenching is detected, because 968 and BPTES are compounds that stabilize tetramer formation. In other words, contact of the FRET pair of GLS dimers by a compound that stabilizes tetramer formation caused additional formation of FRET pairs and, as a result, further absorbance by the acceptor from the donor.

Yet a further aspect of the present invention relates to a screening kit for compounds that inhibit or stabilize tetramer formation. The kit includes a first labeled GLS dimer protein comprising a GLS protein and a fluorescent donor attached to the GLS dimer protein. Also included in the kit is a second labeled GLS dimer protein comprising a GLS protein and a fluorescent acceptor attached to the GLS protein. Binding of the first labeled GLS protein and the second labeled GLS protein forms a GLS protein tetramer and results in an interaction between the fluorescent donor and the fluorescent acceptor which produces a fluorescence resonance energy transfer.

EXAMPLES

The following examples are provided to illustrate embodiments of the present invention but are by no means intended to limit its scope.

Example 1—Development of Fluorescently Labeled Recombinant GAC, Small Molecule Probes for Use in FRET Assays, and Direct Binding Readouts for Allosteric Inhibitors of GAC Materials and Methods Recombinant Glutaminase Preparation and Labeling with Small Molecule Probes A mouse kidney type glutaminase isoform 1 (KGA, NP_001074550.1, which is hereby incorporated by reference in its entirety (SEQ ID NO:7)) and isoform 2 (GAC, NP_001106854.1, which is hereby incorporated by reference in its entirety (SEQ ID NO:3)) plasmid (residues 72-603 for GAC, 72-674 for KGA) was cloned into a pET23a vector containing an N-terminal histidine (His)-tag and thrombin cleavage site. The expressed protein was initially purified using $Co^{2+}$ affinity beads (Clontech), after which the His-tag was cleaved with human thrombin (Haemetologic Technologies) overnight at 4° C. and subsequently purified by anion exchange (GE healthcare) and gel filtration chromatography. Purified GAC or KGA was stored in a high salt containing buffer (20 mM Tris-HCl pH 8.5, 500 mM NaCl, 1 mM $NaN_3$) and stored at −80° C. following snap freezing in liquid $N_2$ for long term use. For labeling recombinant GAC or KGA with small molecule probes, 1.5 mg of enzyme was exchanged to 50 mM HEPES pH 7.2, 100 mM NaCl using a PD10 desalting column (GE healthcare) and incubated with 50 μM (5-fold excess of enzyme) of either ALEXA FLUOR® 488 succinimidyl ester or QSY® 9 succinimidyl ester (Molecular Probes) for 1 hr at 4° C. After 1 hr, the labeling reaction was quenched with 150 mM Tris-HCl pH 8.5 and unreacted probe was separated from labeled-enzyme using a PD10 desalting column eluting labeled-GAC back into the high salt containing buffer.

Analytical Gel Filtration and Multi-Angle Light Scattering (MALS)

Purified GAC and GAC mutants were subjected to analytical size exclusion chromatography on a Superdex 200 10/300 GL column (GE Healthcare) equilibrated with 20 mM Tris-HCl pH 8.5, 200 mM NaCl for experiments in the absence of inorganic phosphate and 20 mM Tris-HCl pH 8.5, 200 mM NaCl, 50 mM $K_2HPO_4$ for experiments in the presence of inorganic phosphate at a temperature of 4° C. and flow rate of 0.4 ml/min. Protein concentrations were prepared to be either 5 mg/mL or 0.5 mg/mL and centrifuged at 10,000×g for 10 minutes prior to injecting 200 μL of each sample. The same protocol was followed for MALS analysis. Briefly, 50 μL samples of 0.5, 5, or 10 mg/mL GAC was injected onto a WTC-030S5 size exclusion column (Wyatt technology) coupled to a static 18-angle light scattering detector (DAWN HELEOS-II) and a refractive index detector (OptiLab T-rEX, Wyatt Technology) kept at 23° C. The flow rate was kept at 1 mL/min. RMS radius and mass distribution (polydispersity) was analyzed using the ASTRA software using monomeric BSA (Sigma) to normalize the light scattering signal.

FRET Assays with 488 and QSY® 9-Labeled GAC

Fluorescence experiments were performed using a Varian Carry Eclipse Fluorometer in the counting mode. Excitation and emission wavelengths were 490 and 520 nm, respectively. Experiments were all prepared as one-mL samples and stirred continuously at 20° C. in 50 mM Tris-Acetate pH 8.5, 0.1 mM ethylenediaminetetraacetic acid (EDTA). For WT GAC titrations in the absence of inorganic phosphate, 10 nM 488-GAC was equilibrated followed by injection of 25 μL of the appropriate concentration of QSY® 9-GAC and was allowed to equilibrate for 10 minutes at which point 75 μL of the appropriate concentration of unlabeled WT GAC was added to give a concentration that was ten-times that of labeled-GAC (i.e., 10-fold excess). For FRET experiments prepared for inorganic phosphate titrations, a similar protocol was followed whereby 10 nM of 488-GAC was equilibrated with 400 nM QSY® 9-GAC followed by injection of 100 μL of the appropriate concentration of $K_2HPO_4$ prepared in 50 mM Tris-Acetate (pH=8.5) 0.1 mM EDTA buffer. To test whether purified mutants can form oligomers with WT GAC, 200 nM QSY® 9-D391K-GAC or 200 nM QSY® 9-K316E-D391K-R459E was added to an equilibrated sample of 20 nM 488-WT GAC. Likewise, when assaying the effects of BPTES and 968 on oligomer formation, BPTES or 968 (10 μM or 25 μM, respectively) was added following equilibration of a sample of 200 nM of QSY® 9-WT GAC and 20 nM 488-WT GAC. Both BPTES and 968 were prepared in DMSO, and appropriate dilutions were made so that less than 2% (v/v) DMSO was added to an experimental sample.

Real-Time 968 Binding and Glutaminase Activity Assays

Figure 7A:
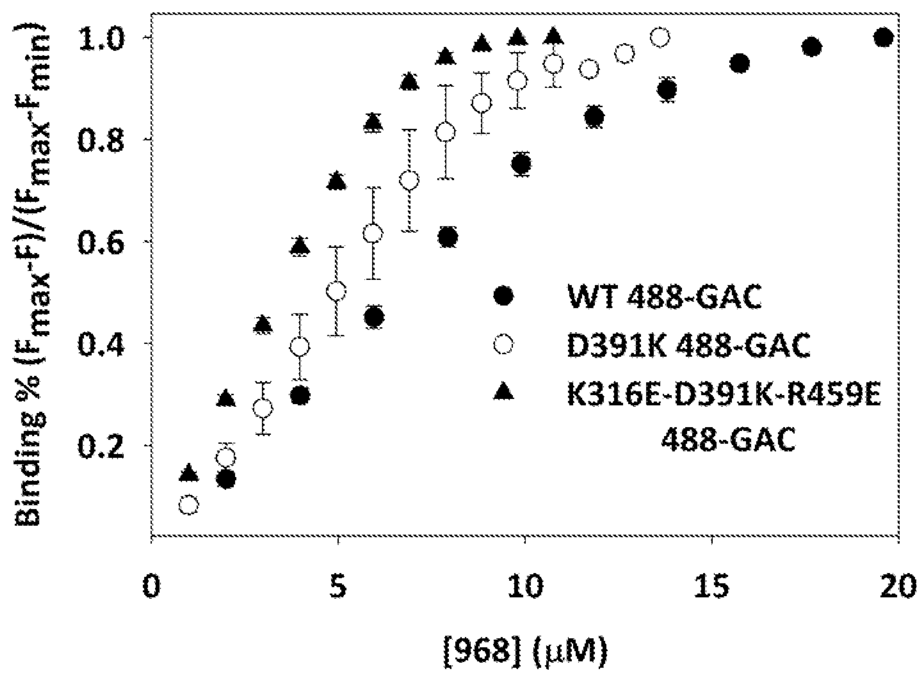
FIGS. 7A-B illustrate that the small molecule 968 preferentially binds to GAC monomer.

Real-time fluorescence monitoring of 488-GAC fluorescence and NADH fluorescence was performed on a Varian Carry Eclipse Fluorometer, whereas small molecule inhibition and binding titrations were performed in a 96-well format using Grenier non-binding 96-well plates in a Tecan Saphire absorbance and fluorescence plate reader. Samples for monitoring real time binding of 968 to 488-GAC were prepared by adding 10 μL of appropriate concentrations of 968 prepared in DMSO to an equilibrated 1 mL sample of 10 nM 488-GAC while observing 488 fluorescence (490 nm excitation/520 nm emission). Similarly, this method was replicated for monitoring real time binding of 968 to KGA and mutant forms of GAC, namely 488-D391K-GAC and 488-K316E-D391K-R459E-GAC. Titrations of 968 with mutant forms of GAC were done in triplicate and quantified by the following equation $$\% \text{ Bound} = \frac{1-F}{1-F_{sat}}, \quad \text{(Eq. 1)}$$

where F is the normalized fluorescence at given drug concentration (i.e., $F/F_0$), and $F_{sat}$ is the normalized fluorescence at saturating concentrations of drug, as shown in FIG. 7A. Real-time activity assays were prepared in 1 mL samples, where 10 units of glutamate dehydrogenase (Sigma) and 2 mM $NAD^+$ (Sigma) was prepared in 50 mM Tris-Acetate pH=8.5, 0.1 mM EDTA and equilibrated at 20° C. 10 nM WT GAC was added and allowed to equilibrate 2 minutes before beginning to monitor fluorescence of 488-GAC (490 nm excitation, 520 nm emission) and NADH fluorescence (340 nm excitation, 490 nm emission). Appropriate dilutions of 968 or BPTES prepared in DMSO were injected after 30 seconds and allowed to equilibrate for 2 minutes before 180 μL of a solution of 333 mM $K_2HPO_4$, 133 mM glutamine, 50 mM Tris-Acetate pH 8.5, 0.1 mM EDTA was added to initiate GAC activation. The activity of GAC was indirectly measured by the NADH produced by the added glutamate dehydrogenase, which converts the product of glutaminase activity, glutamate, to α-ketoglutarate and ammonia through reducing $NAD^+$ to NADH. Because solutions containing glutamine undergo non-enzymatic degradation to glutamate, samples were further analyzed by subtracting the evolved NADH produced by glutaminase in the presence of 968, BPTES, or the equivalent volume of DMSO as a control, by the evolved NADH produced in the absence of glutaminase under identical experimental conditions. Evolved NADH was quantified using a standard curve of freshly prepared NADH (Sigma) in 50 mM Tris-Acetate pH=8.5, 0.1 mM EDTA.

Procedures for the described real-time binding and inhibition assays were adapted for 96-well microtiter format with minor alterations. Briefly, 2 μL of inhibitor or DMSO was distributed across the 96-well plate followed by addition of 200 μL 10 nM 488-GAC, unlabeled WT-GAC, or no added GAC as a negative control in 50 mM Tris-Acetate pH 8.5, 0.1 mM EDTA and immediate monitoring of 488 fluorescence (490 nm/520 nm excitation/emission, 5 nm/20 nm excitation/emission slits). 488-fluorescence was measured every two minutes with 90 seconds of orbital shaking followed by 30 second resting between each cycle for a total of four cycles (i.e., 6 minutes). Immediately following, 20 μL of a mixture of GDH and $NAD^+$ were added to give 10 Units GDH and 2 mM $NAD^+$. To activate GAC, 30 μL of a mixture of glutamine and $K_2HPO_4$ prepared in the Tris-acetate assay buffer was added to give 50 mM $K_2HPO_4$, and 20 mM glutamine in each well. NADH fluorescence was measured (340 nm/460 nm excitation/emission, 10 nm/10 nm excitation/emission slits) every minute with 30 second orbital shaking and 30 second rest between each reading for 10 cycles (i.e., 9 minutes). Three wells were prepared for each experimental condition (i.e., each concentration of compound) alongside one well where 2 μL of DMSO was added in place of inhibitor and one well that contained the small molecule inhibitor but no GAC was added. To analyze 488-quenching by the added compound, 488-fluorescence (F) was normalized to the DMSO control ($F_0$) immediately adjacent to the experimental condition. Quenching was quantified by subtracting the normalized fluorescence by one (i.e., $1\text{-}F/F_0$). For compounds that emitted fluorescence within the observed range, fluorescence measured in the well that contained the compound but lacked GAC was used to subtract added fluorescence due to the compound. Similarly, samples were analyzed for NADH fluorescence by subtracting the evolved fluorescence in the experimental condition by the NADH fluorescence evolved in the well that contained the added compound but no GAC. Percent inhibition at each drug concentration was calculated using the adjacent DMSO control.

End Point Glutaminase Activity Assays

Activity assays used to compare FRET values and evaluate activity of GAC mutants followed a two-step protocol adapted from Robinson et al., "Novel Mechanism of Inhibition of Rat Kidney-type Glutaminase by bis-2-(5-phenylacetamido-1,2,4-thiadiazol-2-yl)Ethyl Sulfide (BPTES)," *Biochem. J.* 406:407-414 (2007), which is hereby incorporated by reference in its entirety. Briefly, 20 μL of 20 mM glutamine, 50 mM Tris-acetate pH 8.5, 0.1 mM EDTA, in either the presence or absence of a $K_2HPO_4$ dilution was distributed in a UV-transparent Costar 96-well plate (Corning). 5 μL of the appropriate concentration of GAC prepared in 20 mM Tris-HCl pH 8.5, 100 mM NaCl, 1 mM $NaN_3$ was added to the glutamine solution and allowed to incubate at 23° C. for two minutes before the reaction was quenched using 2.5 μL 3 M HCl. For reactions that contained more than 250 nM of GAC, the first reaction was quenched at 30 seconds instead of two minutes. The second step was initiated by the addition of 200 μL of 12 Units/μL GDH, 2 mM $NAD^+$, 100 mM hydrazine (Sigma), and 100 mM Tris-HCl pH 9.2 was on top of the first quenched reaction and incubated 45 minutes at 23° C. before reading NADH absorbance. Glutamate produced by the first reaction was equated to NADH measured from reaction two using the extinction coefficient of NADH (6,220 $M^{-1}$ $cm^{-1}$) and a standard curve of a glutamate titration prepared as 25 μL in step one.

Results

Reading Out the Dimer-to-Tetramer Transition of GAC and its Relationship to Enzyme Activity The transition of GAC from a dimer to a tetrameric species has been suggested to be the obligatory step for the activation of enzyme activity (Godfrey et al., "Correlation Between Activation and Dimer Formation of Rat Renal Phosphate-Dependent Glutaminase," *J. Biol. Chem.* 252(6): 1927-1931 (1977), which is hereby incorporated by reference in its entirety). Because BPTES, a well characterized inhibitor of GAC, has been shown to block GAC activity by stabilizing an inactive, tetrameric state of the enzyme, it was of interest to see whether 968 acted in a similar manner, and/or exerted some other type of influence on the dimer-to-tetramer transition of GAC. As a first step, a real-time read-out for the dimer-tetramer transition of GAC was developed, specifically, by using a FRET assay using two populations of purified recombinant GAC molecules labeled with either the highly fluorescent ALEXA FLUOR® 488 (donor) probe, or with the non-fluorescent QSY® 9 (acceptor) probe (FIG. 1A).

The advantage of using FRET as a direct read-out for GAC tetramer formation comes from the high sensitivity of the fluorescence donor group, which makes it possible to keep the concentration of 488-GAC in the low nanomolar regime, where 488-GAC predominantly exists in an inactive dimeric or monomeric state.

Figure 1B:
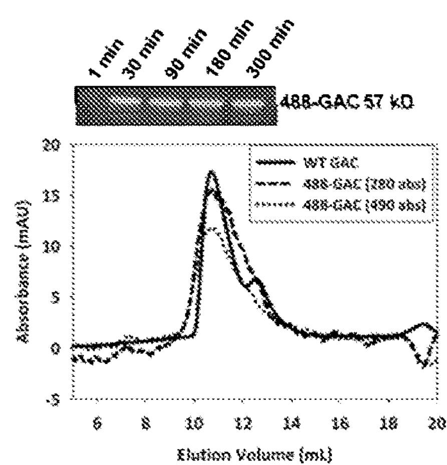
Figure 1C:
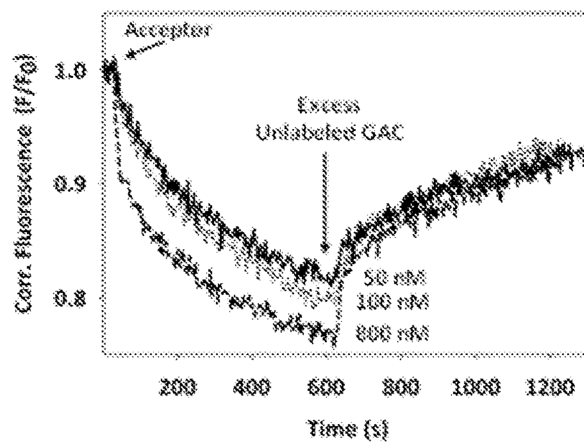
Figure 1D:
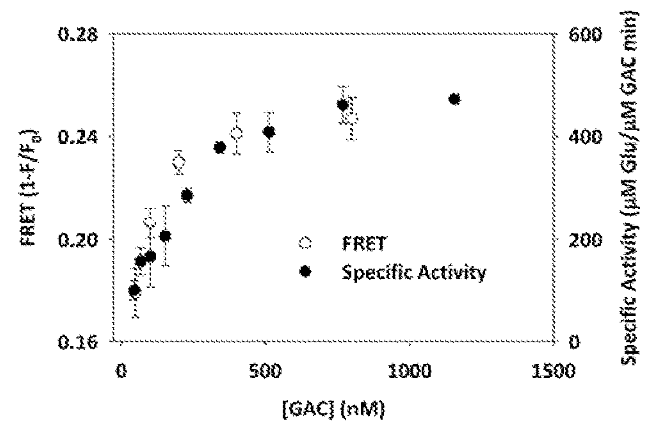
Figure 1E:
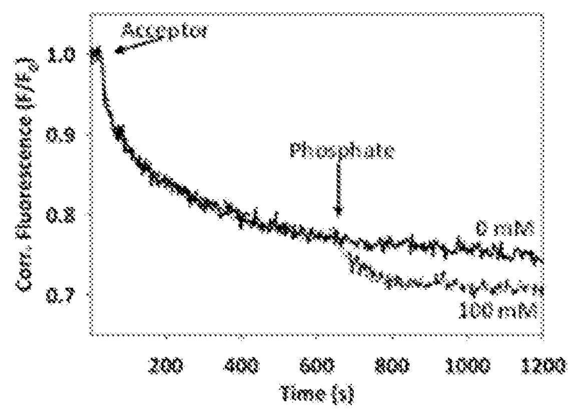
Figure 1F:
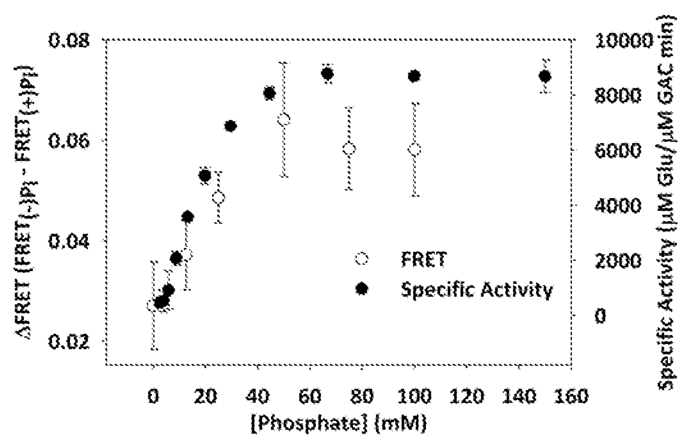
Figure 8A:
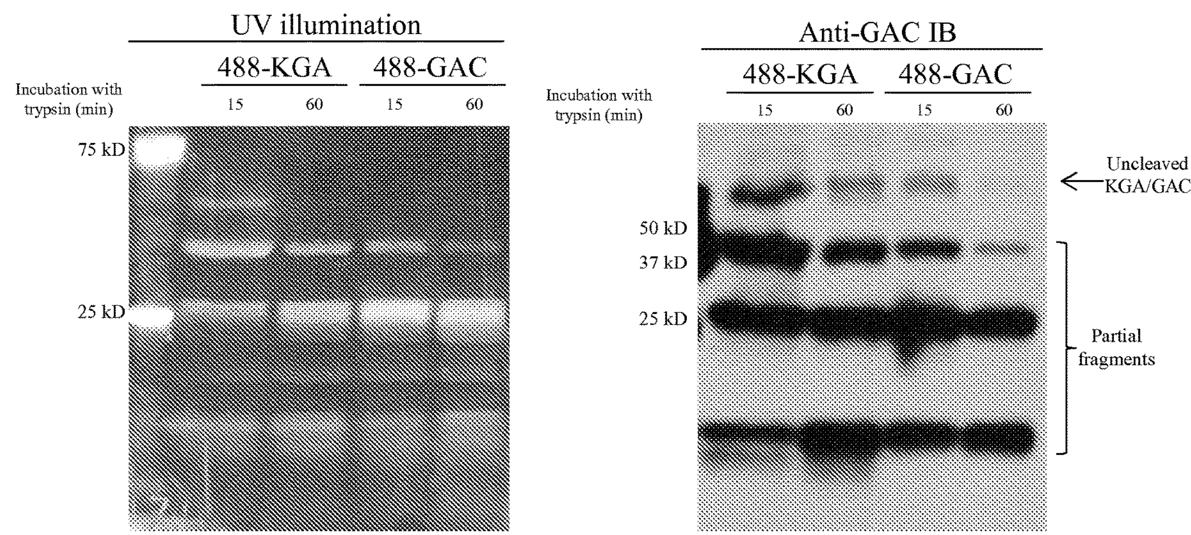
Figure 8B:
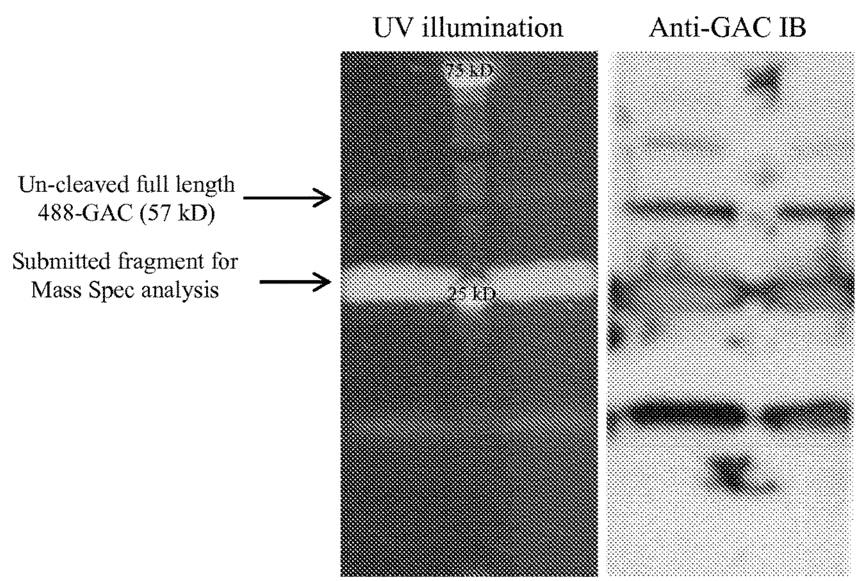

The labeling of recombinant GAC was shown to be both rapid and stoichiometric, and did not influence the oligomeric state of the 488-labeled GAC when compared to unlabeled GAC using analytical gel filtration (FIG. 1B). The site of covalent modification was shown to be within the conserved glutaminase domain, by means of mass spectrometry identification of peptide fragments produced by partial trypsin digestion and separation by SDS-PAGE (FIGS. 8A-C). Indeed, efficient fluorescence quenching was observed when the fluorescence of the 488 labeled GAC was monitored upon addition of the acceptor labeled QSY® 9-GAC (FIG. 1C). The quenching was shown to be concentration dependent with the resultant FRET titration curve strongly correlating with the concentration dependent activation of WT-GAC (FIG. 1D). It has previously been shown that inorganic phosphate stimulates the activity of GAC (Godfrey et al., "Correlation Between Activation and Dimer Formation of Rat Renal Phosphate-Dependent Glutaminase," *J. Biol. Chem.* 252(6):1927-1931 (1977); Svenneby et al., "Glutaminase from Pig Renal Cortex: II. Activation by Inorganic and Organic Anions," *J. Biol. Chem.* 245:1878-1882 (1970); Scota Ferreira et al., "Active Glutaminase C Self-Assembles into a Supratetrameric Oligomer that can be Disrupted by an Allosteric Inhibitor," *J. Biol. Chem.* 288:28009-28020 (2013), which are hereby incorporated by reference in their entirety), and was proposed to do so by inducing tetramer formation. Addition of phosphate to the described FRET assay did induce further quenching characteristic of tetramer formation, and when quantified correlated well with the phosphate stimulation profile of WT-GAC (FIGS. 1E and 1F). For the first time, a real-time readout of phosphate binding to GAC is reported. This FRET assay was also shown to read-out KGA, the alternate splice variant of Gls, tetramer formation in identical experiments (FIGS. 9A-B), underscoring the utility of using the developed FRET assay to investigate glutaminase enzyme oligomerization.

Figure 2A:
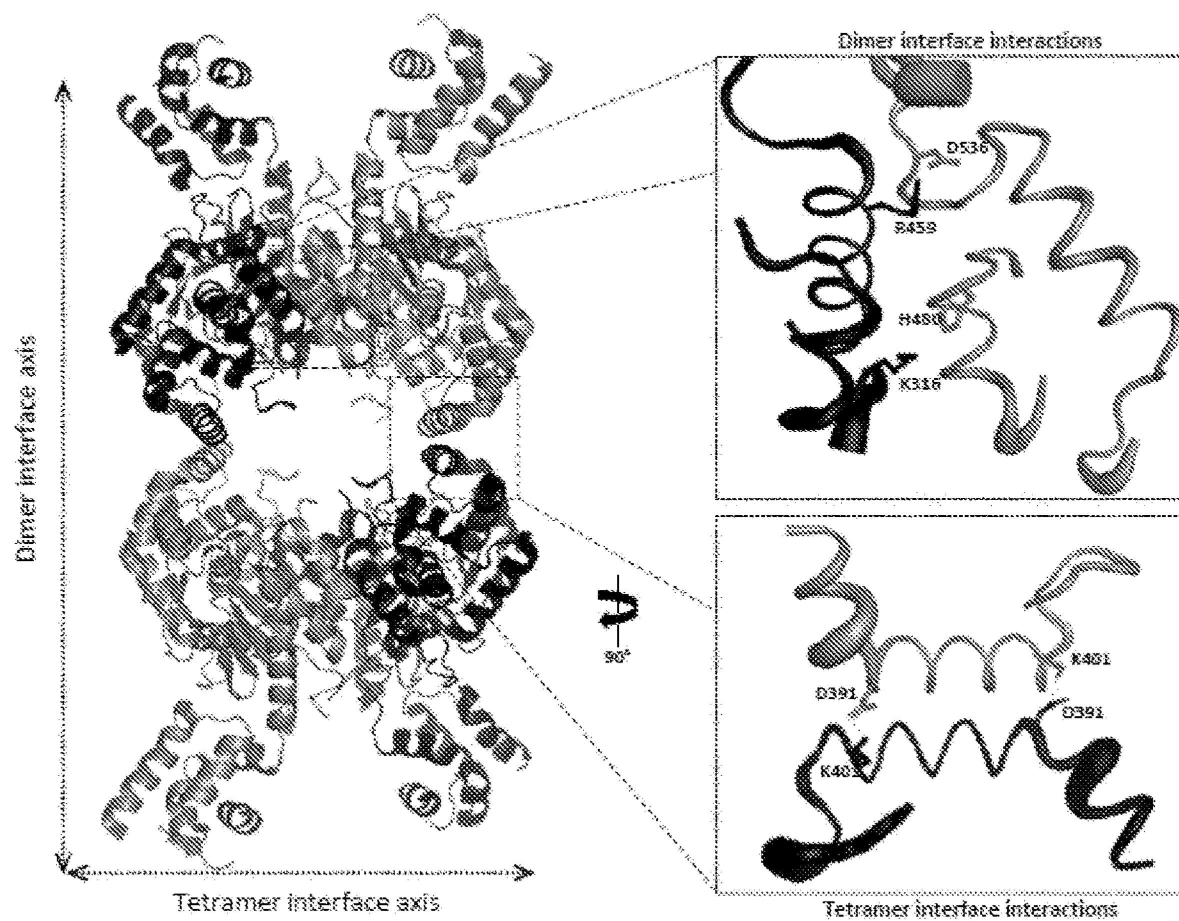
FIGS. 2A-B illustrate that mutating specific residues at the GAC monomer and dimer interface traps mutants in a defined oligomeric state.
Figure 2B:
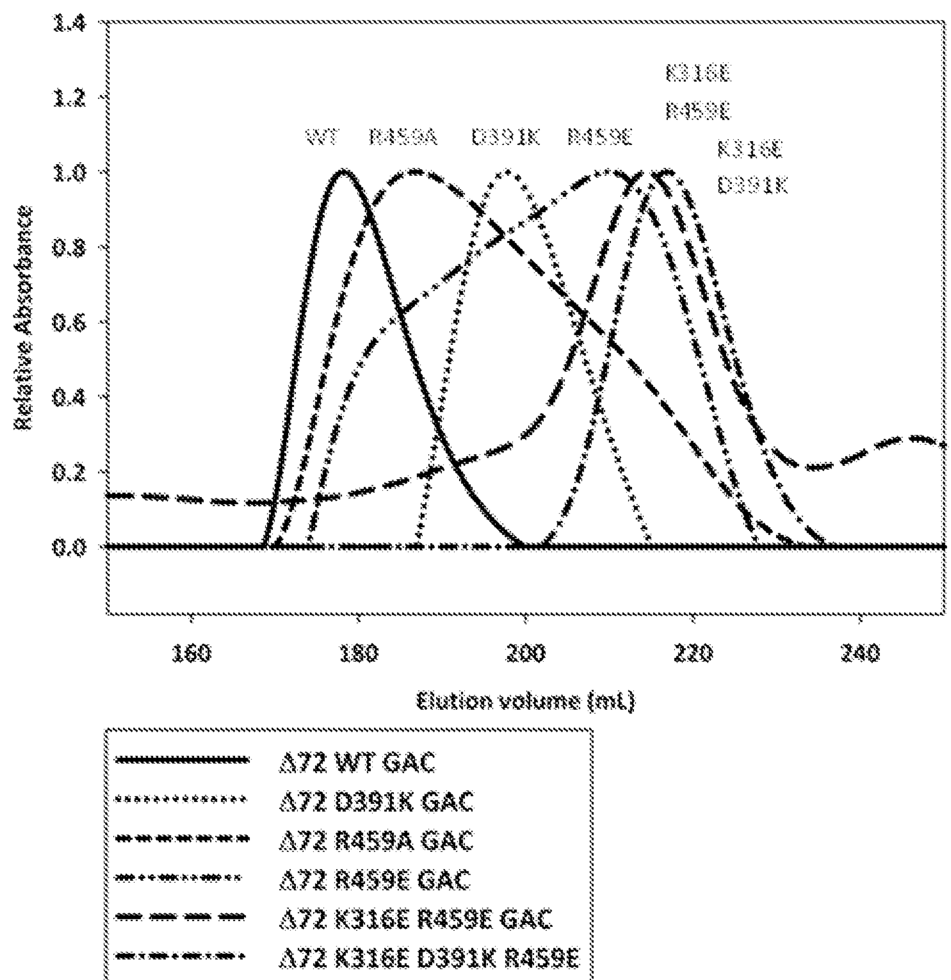
Figure 3A:
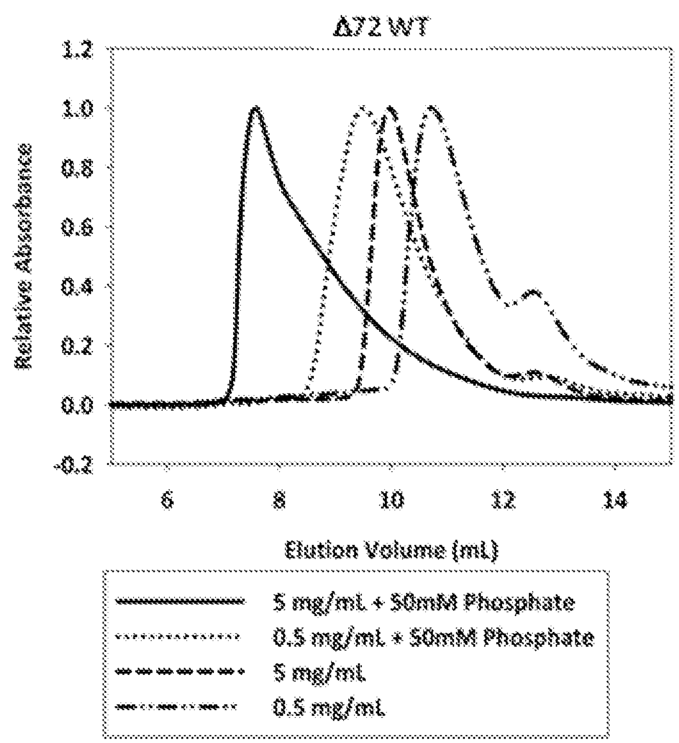
FIGS. 3A-C illustrate that WT GAC accesses monomer, dimer, and larger oligomeric species in a concentration and phosphate dependent manner.
Figure 3B:
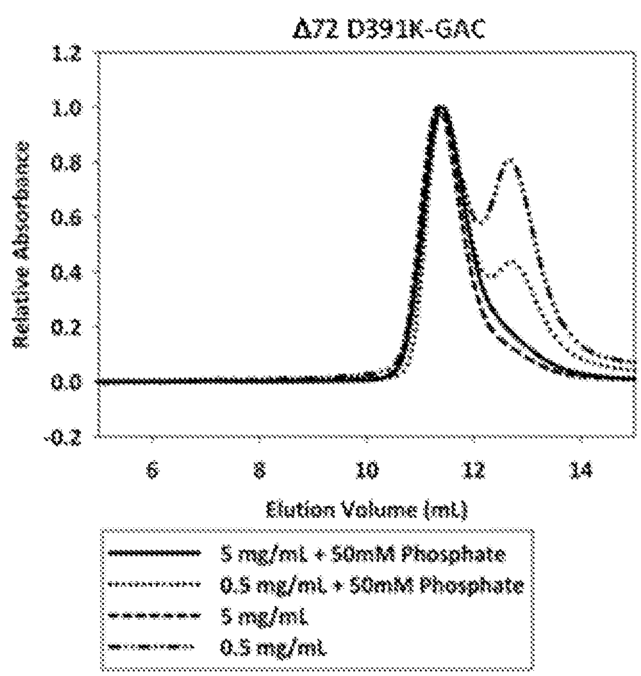
Figure 3C:
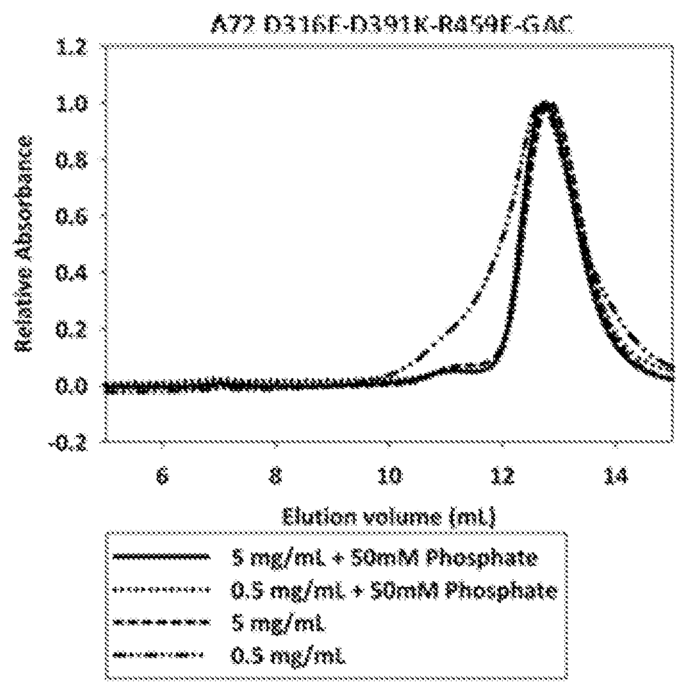

To further aid in the analysis, recently solved x-ray crystal structures of GAC (Cassago et al., "Mitochondrial Localization and Structure-Based Phosphate Activation Mechanism of Glutaminase C with Implications for Cancer Metabolism," *Proc. Natl. Acad. Sci.* 109(4):1092-1097 (2012), which is hereby incorporated by reference in its entirety) were used to design oligomeric-defective mutants to use for investigating the dependence of GAC enzymatic activity on its oligomeric state. FIG. 2A highlights critical contacts identified at the GAC tetramer interface (FIG. 2A, bottom inset), as well as the GAC dimer interface (FIG. 2A, top inset). Initial screens were performed by purifying GAC constructs with point mutations at select residues at both the dimer and tetramer interfaces. Gel filtration profiles of these mutants suggested that one mutation was sufficient to trap GAC in a dimeric state (D391K), whereas a specific combination of mutations was needed to disrupt the dimer interface interactions enough to trap GAC in a monomeric state (K316E/D391K/R459E) (FIG. 2B). These studies were extended to analytical gel filtration to show that the oligomeric state of WT GAC is dependent on the concentration of the enzyme, whereas the two mutants could not access higher molecular weight species and were thus trapped in either the dimeric or monomeric state (FIGS. 3A-C). Additionally, multi-angle light scattering (MALS) downstream of size exclusion chromatography (SEC) was used to calculate the molecular weight of these constitutive dimer and monomer mutants in both the presence and absence of inorganic phosphate (FIGS. 4A-D).

Figure 4A:
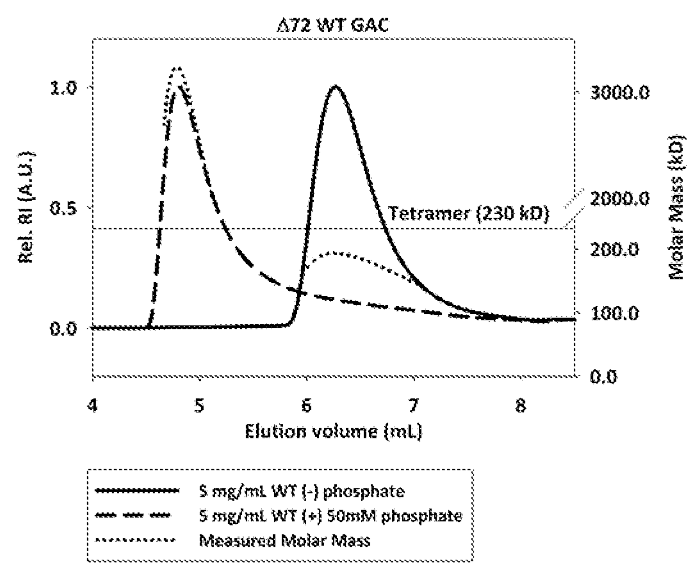
FIGS. 4A-F define the oligomeric species of GAC mutants. In particular, multi-angle light scattering profiles of WT-GAC (FIG. 4A), D391K-GAC (FIG. 4B), K316E-D391K-R459E-GAC (FIG. 4C), and K316E-GAC (FIG. 4D) were obtained following SEC and subsequent MALS analysis, where elution of each species was monitored using refractive index (left axis). Upon elution, light scattering data was collected and then used to calculate the molecular weight and polydispersity for the species eluted (right axis). Reference lines for the molecular weights of the monomer, dimer, and tetramer forms of GAC are included at 58 kD, 116 kD, and 230 kD respectively.
Figure 4B:
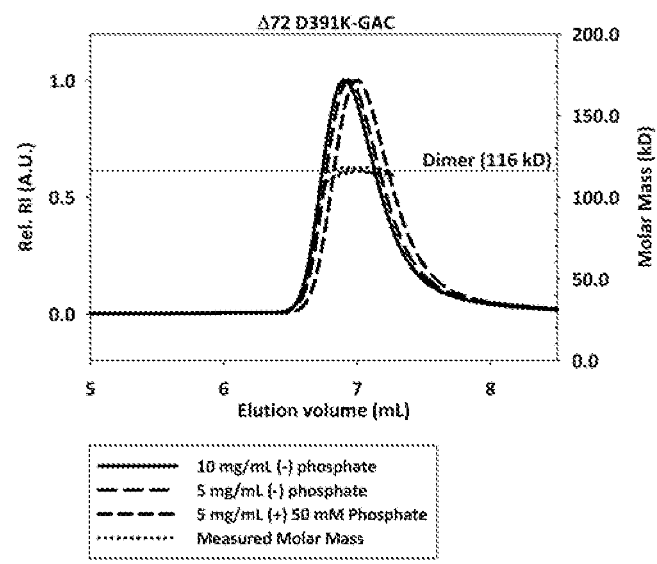
Figure 4C:
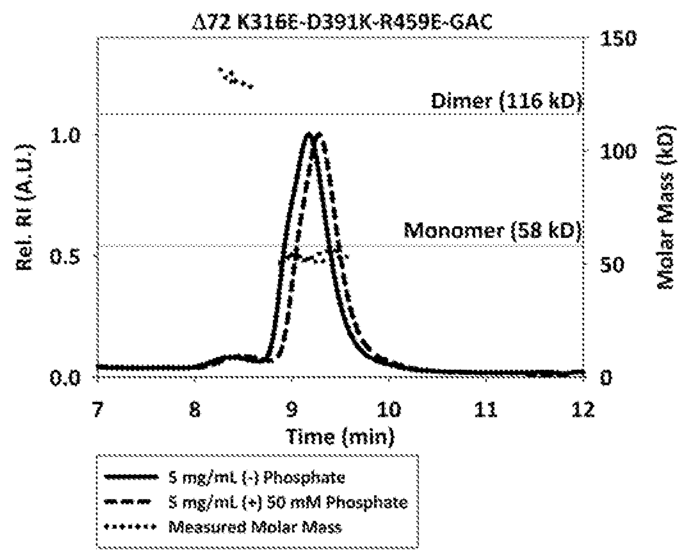
Figure 4D:
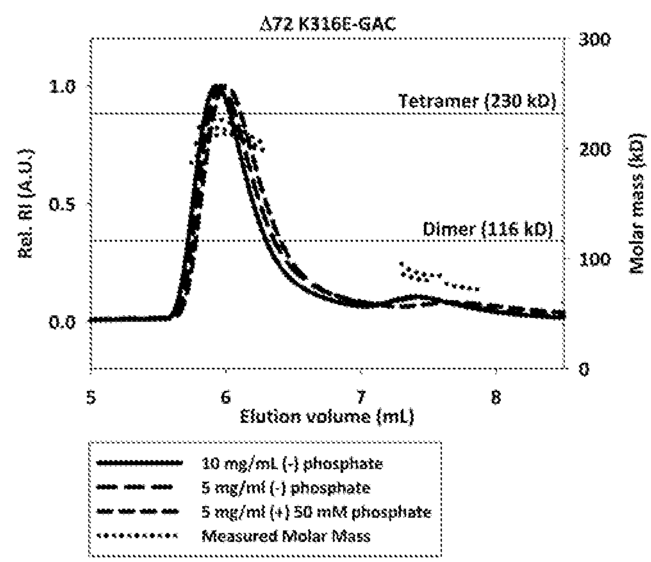
Figure 4E:
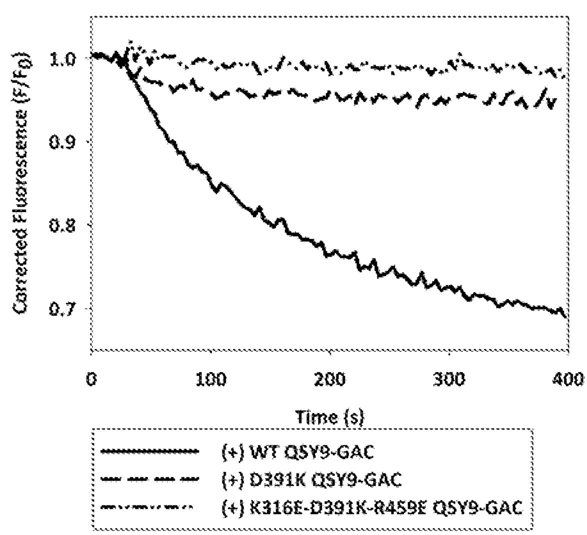
Figure 4F:
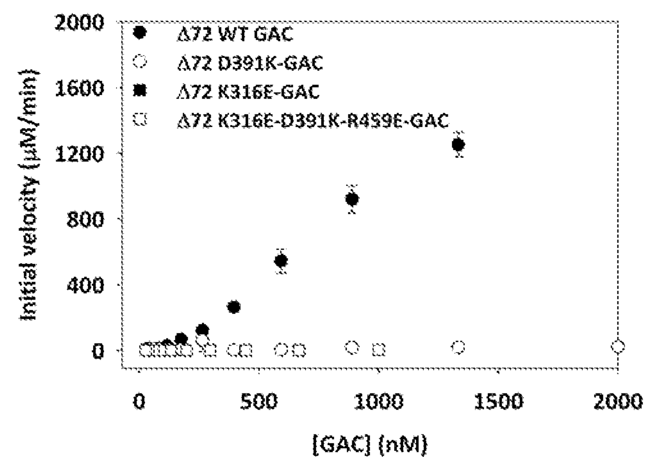

Using these novel GAC mutants, GAC tetramer formation was monitored in the developed FRET assay. Based on the design of the FRET assay described herein, the fluorescence emission of 488-GAC (donor) should be quenched upon addition of the non-fluorescent QSY® 9-GAC (acceptor) and thereby serve as a direct read-out of GAC tetramer formation. Indeed, this FRET assay is specific for GAC tetramer formation as indicated in experiments where the QSY® 9-labeled, constitutive GAC dimer (D391K) mutant and monomer GAC (K316E/D391K/R459E) mutant, described above (FIG. 4E) were used. The addition of QSY® 9-GAC (WT) resulted in an efficient energy transfer, with an observed $E_{FRET}$ max value of approximately 0.3, whereas only a minor extent of FRET was observed upon the addition of the QSY® 9-GAC (D391K) dimer mutant, and with no observable energy transfer being detected upon the addition of QSY® 9-GAC (K316E, D391K, R459E) monomer mutant. The restriction of these mutants to a defined oligomeric state confers the inactivation of enzymatic activity, suggesting the transition from the monomer-to-dimer-to-tetramer is necessary to activate the enzyme (FIG. 4F). These results are consistent with the biophysical characterization of the oligomeric-deficient GAC mutants, as well as further emphasize that GAC tetramer formation is an obligatory step for enzyme activation.

Figure 5B:
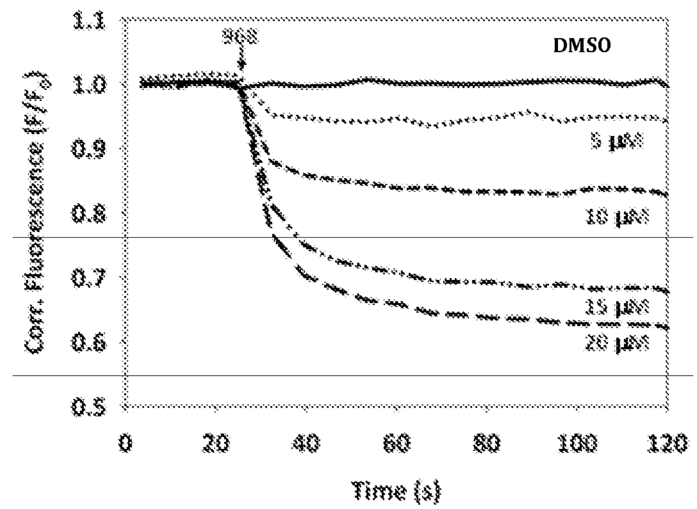
Figure 5C:
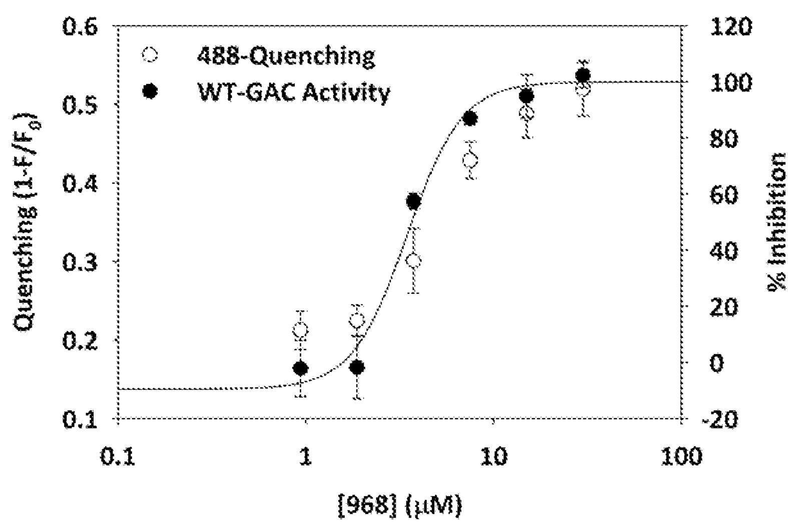

Effects of the Small Molecule Inhibitor 968 on the Dimer-to-Tetramer Transition of GAC Having established the relationship between the GAC dimer-to-tetramer transition and enzyme activation, the effects of 968, versus BPTES, on these processes were examined. The addition of the allosteric inhibitor BPTES has been shown to stabilize GAC as an inactive tetramer (DeLaBarre et al., "Full-Length Human Glutaminase in Complex with an Allosteric Inhibitor," *Biochemistry* 50:10764-10770 (2011); Thangavelu et al., "Structural Basis for the Allosteric Inhibitory Mechanism of Human Kidney-Type Glutaminase (KGA) and its Regulation by Raf-Mek-Erk Signaling in Cancer Cell Metabolism," *Proc. Natl. Acad. Sci.* 109(20):7705-7710 (2012); Cassago et al., "Mitochondrial Localization and Structure-Based Phosphate Activation Mechanism of Glutaminase C with Implications for Cancer Metabolism," *Proc. Natl. Acad. Sci.* 109(4):1092-1097 (2012), which are hereby incorporated by reference in their entirety), and thus causes an immediate quenching of 488-GAC fluorescence emission when added to an equilibrated mixture of 488-GAC and QSY® 9-GAC (FIG. 5A). The observed quenching is due to the BPTES-induced formation of 488-GAC:QSY® 9-GAC (donor:acceptor) tetramers, which are stable and not disrupted by the addition of excess unlabeled GAC. In contrast, the addition of 968 elicited a markedly different response. 968 addition caused a significant change in the fluorescence emission of 488-GAC, followed by a modest fluorescence recovery upon the addition of excess unlabeled GAC (FIG. 5A). However, importantly, the fraction of fluorescence quenching due to 968 addition was not reversed upon addition of excess unlabeled GAC and therefore independent of GAC tetramer formation, as the addition of 968 to 488-GAC, alone, resulted in the same degree of quenching (compare FIGS. 5A and 5B). Indeed, the fluorescence quenching of 488-GAC that accompanies 968 addition was found to reflect the direct binding of 968 to GAC, which perfectly matched the 968-mediated inhibition of GAC activity (FIG. 5C). These findings demonstrate that the FRET changes caused by GAC tetramer formation, and the fluorescence quenching resulting from the addition of 968, are two distinct events. In contrast to what was observed for BPTES, the addition of unlabeled GAC to a 968-bound 488-GAC-QSY® 9-GAC tetrameric complex resulted in the recovery of 488-GAC fluorescence, indicating that 968 does not mimic the actions of BPTES which traps GAC in a tetrameric state, thus definitively demonstrating that 968 inhibits GAC activity through an allosteric mechanism distinct from that of BPTES.

Figure 6B:
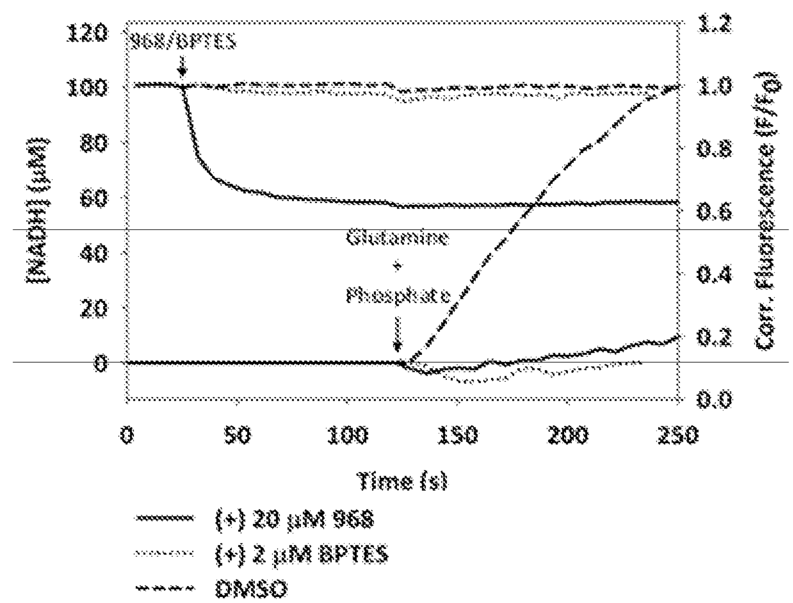
Figure 6C:
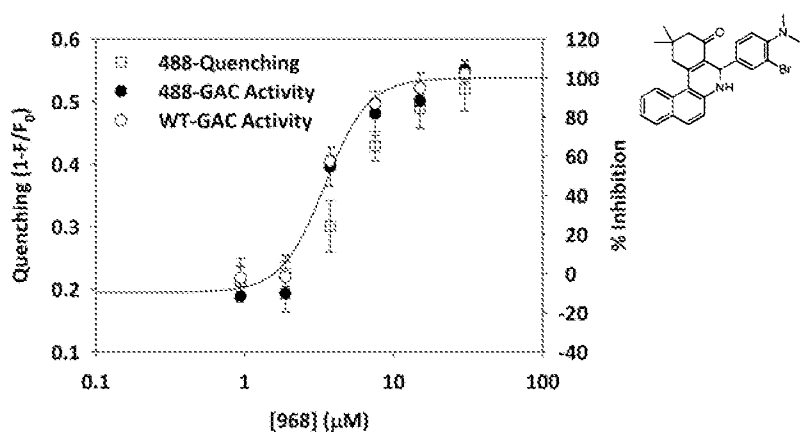
Figure 6D:
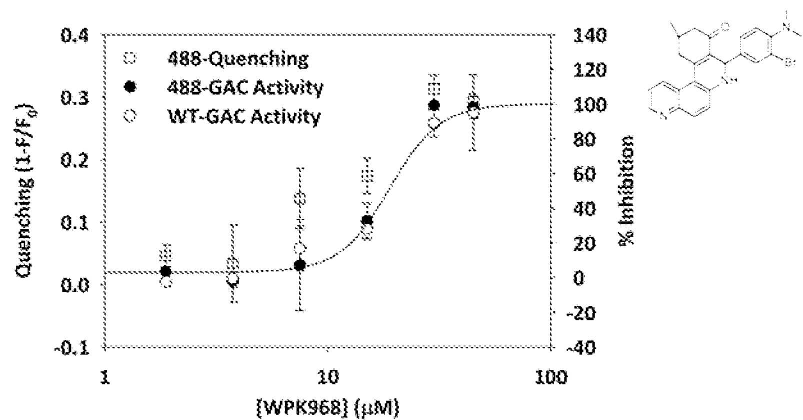
Figure 6E:
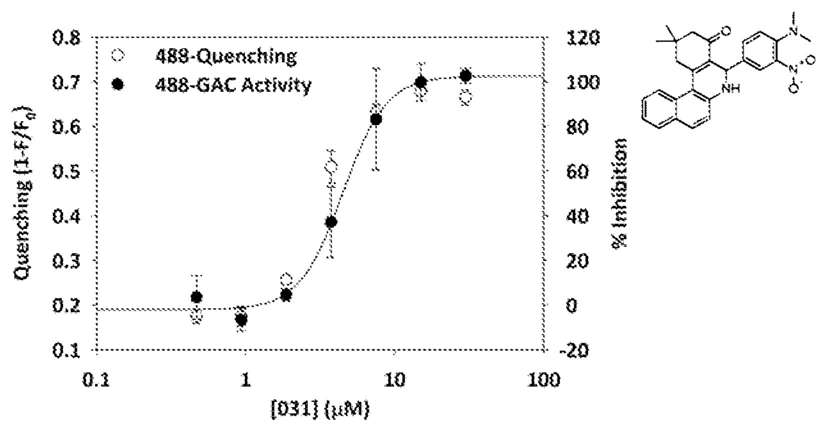
Figure 6F:
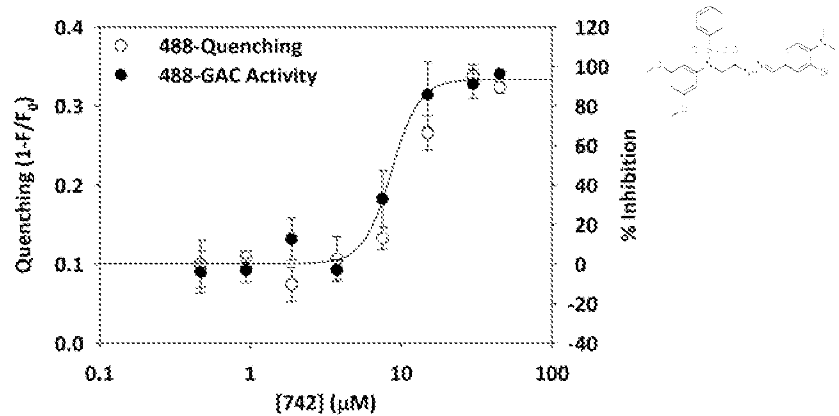

Given the ability to read-out the direct binding of 968 to GAC, it was sought to develop a real-time enzyme activity assay that would make it possible to simultaneously examine 968-GAC complex formation and the effects of 968 on enzyme activity. FIG. 6A depicts a model of the enzyme activity assay coupled with the 968-binding assay, where the activity of 488-GAC can be monitored following the interaction of 968 by detecting the NADH fluorescence that results from the coupled glutamate dehydrogenase (GDH) reaction. GDH catalyzes the conversion of glutamate (i.e., the product of GAC activity), to α-ketoglutarate through the reduction of $NAD^+$ (which is non-fluorescent), to NADH (which is highly fluorescent). By monitoring both 488-GAC and NADH fluorescence (520 nm and 460 nm emission, respectively), the inhibition of 488-GAC by 968 could be directly correlated with the observed quenching of 488-GAC fluorescence (FIG. 6B). Adapting these fluorescence assays to a 96-well microtiter format, it was found that 968 exhibits a similar dose-dependent inhibition of both 488-GAC and unlabeled GAC (WT) by 968 (FIG. 6C), and that there is a direct correlation between the effects of 968 on GAC activity and its ability to directly bind to GAC. When using BPTES in place of 968, it was found that BPTES caused a potent inhibition of GAC activity without affecting the fluorescence emission of 488-GAC, further illustrating the specificity of this real-time assay to differentiate 968-like and BPTES-like inhibitors. This real-time coupled fluorescence assay was extended to compare binding and inhibition of previously identified 968-like compounds, further illustrating the utility of this assay to read out binding of 968-like molecules to the 968-allosteric site and at the same time enzyme activity (FIGS. 6D-F) (Katt et al., "Dibenzophenanthridinones as Inhibitors of Glutaminase C and Cancer Cell Proliferation," *Mol. Cancer Ther.* 11:1269-1278 (2012), which is hereby incorporated by reference in its entirety). The assay presented here is a novel tool to monitor both the binding of 968-like molecules, but not BPTES-like molecules, to GAC and the activity of the enzyme in a real-time fluorescent readout using 488 fluorescence (520 nm emission) and NADH fluorescence (460 nm emission) making it highly adaptable to high-throughput screening.

968 Preferentially Binds to the Monomeric State of GAC

Previous studies highlighted differences in the dose-response profiles when monitoring the inhibition of oncogenic transformation by 968 in cells, versus its ability to inhibit the inorganic phosphate-stimulated activity of recombinant GAC in vitro (Wang et al., "Targeting Mitochondrial Glutaminase Activity Inhibits Oncogenic Transformation," *Cancer Cell* 18:207-219 (2010); Katt et al., "Dibenzophenanthridinones as Inhibitors of Glutaminase C and Cancer Cell Proliferation," *Mol. Cancer Ther.* 11:1269-1278 (2012), which are hereby incorporated by reference in their entirety). In addition, the in vitro assays of 968-mediated inhibition of GAC activity showed that 968 was much more effective when it was added prior to glutamine and inorganic phosphate, compared to when 968 was added after the addition of inorganic phosphate (Katt et al., "Dibenzophenanthridinones as Inhibitors of Glutaminase C and Cancer Cell Proliferation," *Mol. Cancer Ther.* 11:1269-1278 (2012), which is hereby incorporated by reference in its entirety). These findings suggested that 968 preferentially interacts with an inactive GAC species (i.e., a dimer rather than a tetramer).

Figure 10A:
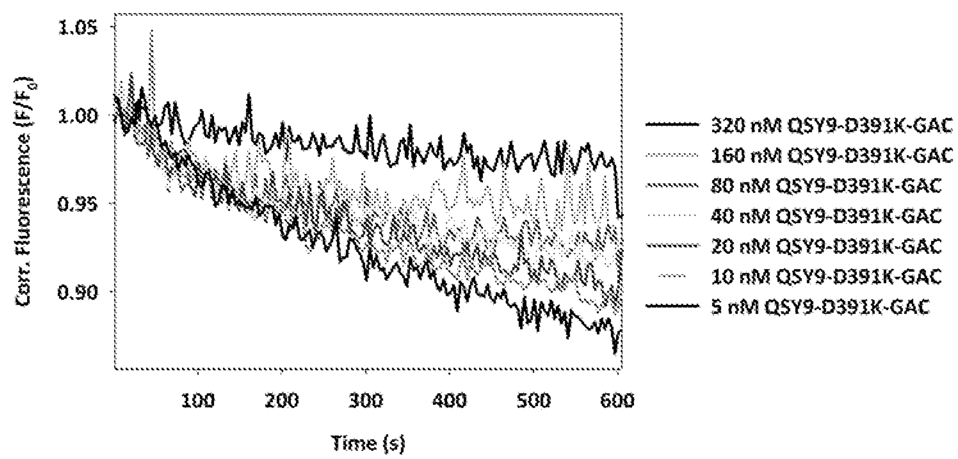
FIGS. 10A-B illustrate measuring of the monomer-monomer binding affinity.
Figure 10B:
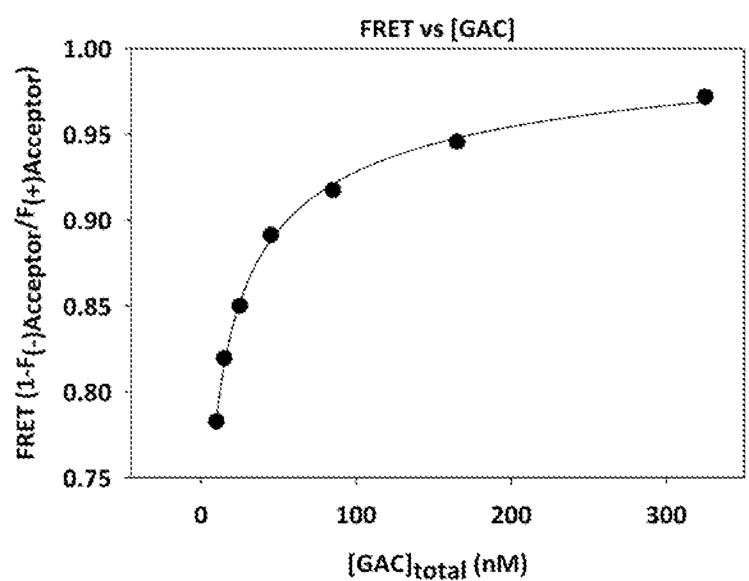

Having the constitutive dimeric and monomeric mutants of GAC in hand, the binding affinities of 968 for these oligomeric-deficient GAC mutants was then examined. It was found that 968 was capable of binding to 488-labeled GAC (WT), as well as to the dimeric GAC (D391K) and the monomeric GAC (K316E-D391K-R459E) mutants, with the monomeric form of GAC having the highest affinity for 968 (FIG. 7A). These results suggested that the binding of 968 to GAC should have the highest affinity at concentrations below the $K_D$ of the formation of GAC dimers, which could be calculated by labeling the dimeric GAC (D391K) mutant with donor and acceptor probes and monitoring FRET. Using this approach, it was determined that the affinity for the interaction between two GAC monomers to form a dimeric GAC species was relatively high with a $K_D$ value of 2.5 nM (FIGS. 10A-B). Additionally, once the GAC dimer was formed, it was very stable and not able to be rescued by the addition of unlabeled GAC subunits. Instead, increasing the concentration of the QSY® 9-labeled GAC (D391K) dimer mutant resulted in an observed decrease in FRET (FIG. 10A), where the donor and acceptor FRET pairs were only formed at low GAC concentrations. The loss of FRET with respect to increasing concentrations of the QSY® 9-labeled GAC (D391K) mutant was highly quantifiable (FIG. 10B) and further explains the minor amount of FRET detected when QSY® 9-labeled GAC (D391K) was added to 488-labeled GAC (WT) (FIG. 4E).

Figure 7B:
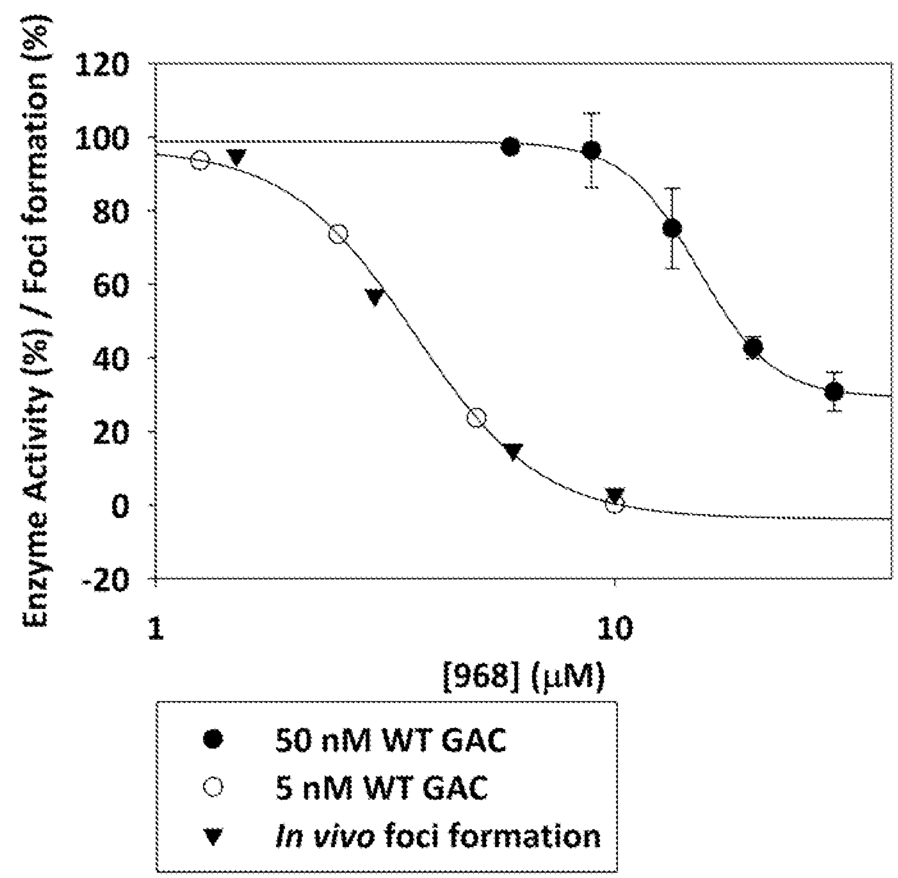

The finding that 968 preferentially binds to the monomeric form of GAC suggested that it should best inhibit GAC activity at lower enzyme concentrations where the monomer is the prevalent GAC species. FIG. 7B illustrates that by simply decreasing the concentration of GAC from 50 nM to 5 nM, 968 was able to inhibit GAC activity with higher efficacy and potency. However, what was potentially even more important is that under these conditions, it was found that the 968-mediated inhibition of GAC activity correlates extremely well with its inhibition of oncogenic transformation as read out by inhibition of oncogene-induced foci formation. Taking these observations into consideration, the 488-labeled monomer mutant would provide an efficient means for screening a compound's ability to bind to the 968 allosteric site.

CONCLUSION

Glutamine metabolism is a central metabolic pathway that has been shown to play a vital role in a variety of physiological conditions, ranging from DNA repair in response to ultra-violet radiation (Jeong et al., "SIRT4 has Tumor-Suppressive Activity and Regulates the Cellular Metabolic Response to DNA Damage by Inhibiting Mitochondrial Glutamine Metabolism," *Cancer Cell* 23(4):450-463 (2013), which is hereby incorporated by reference in its entirety), glutamate toxicity that often accompanies strokes or HIV infection (Ye et al., "Il-1β and TNF-a Induce Neurotoxicity Through Glutamate Production: A Potential Role for Neuronal Glutaminase," *J.* Neurochemistry 125(6):897-908 (2013); Huang et al., "Glutaminase Dysregulation in HIV-1-Infected Human Microglia Mediates Neurotoxicity: Relevant to HIV-1-Associated Neurocognitive Disorders," *J. Neuroscience* 31(42):15195-15204 (2011), which are hereby incorporated by reference in their entirety), to recently being identified as a new therapeutic target for the treatment of many human cancers (Pieter et al., "Analysis of Glutamine Dependency In Non-Small Cell Lung Cancer," *Cancer Biology & Therapy* 13 (12):1185-1194 (2012); Turowski et al., "Glutamine Modulates Phenotype and Stimulates Proliferation in Human Colon Cancer Cell Lines," *Cancer Res.* 54:5974-5980 (1994); Son et al., "Glutamine Supports Pancreatic Cancer Growth Through a KRAS-Regulated Metabolic Pathway," *Nature* 496:101-105 (2013); Gross et al., Antitumor Activity of the Glutaminase Inhibitor CB-839 in Triple-Negative Breast Cancer," *Mol. Cancer Ther*. (Epub ahead of print) (2014), which are hereby incorporated by reference in their entirety). The studies presented here provide insight on the structural requirements for activating the enzyme that catalyzes the first step in glutamine metabolism, mitochondrial glutaminase, as well as methods for monitoring the binding and inhibition of glutaminase by a novel class of inhibitors.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A labeled glutaminase (GLS) protein comprising: a mutated GLS protein, and a fluorescent reporter group attached to the mutated GLS protein, wherein the mutated GLS protein is a GLS monomer incapable of forming a GLS dimer, and the GLS protein is selected from the group consisting of SEQ ID NO: 11, 12, or 19, wherein the fluorescent reporter group is a synthetic fluorophore compound, and wherein the fluorescent reporter group is attached to the mutated GLS protein within (i) a region of the amino acid sequence consisting of amino acid residues 73-545 of SEQ ID NO: 11, (ii) a region of the amino acid sequence consisting of amino acid residues 73-550 of SEQ ID NO: 12, or (iii) the amino acid sequence consisting of SEQ ID NO:19.

* * * * *

SEQUENCE LISTING

```
<160> NUMBER OF SEQ ID NOS: 19

<210> SEQ ID NO 1
<211> LENGTH: 598
<212> TYPE: PRT
<213> ORGANISM: Homo sapiens

<400> SEQUENCE: 1

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300
```

```
Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575

Pro Glu Ser Asn Glu Asp Ile Ser Thr Thr Val Val Tyr Arg Met Glu
            580                 585                 590

Ser Leu Gly Glu Lys Ser
        595
```

<210> SEQ ID NO 2
<211> LENGTH: 4850
<212> TYPE: DNA
<213> ORGANISM: Homo sapiens

<400> SEQUENCE: 2

```
agtgcggagc cttaggcgga gcgaagagaa ccggtcgcgg caatcctagc gcgcagcagc      60

agcagcagca gcagcagcag cagcagcagc agcagcagca cccgcatccg ctgcgggagt     120

ccgagccgga accacaccca agtagctgcc ctttcctctt ctgtcatctc accgccccac     180

cacagaccgc gttccccgag gaaaccggcc gcccacgccc ggagcatcct cccctgttga     240

gcgggcgctg acggacccgg cggcatgatg cggctgcgag gctcggggat gctgcgggac     300

ctgctcctgc ggtcgcccgc cggcgtgagc gcgactctgc ggcgggcaca gcccttggtc     360

accctgtgcc ggcgtccccg aggcgggga cggccggccg cgggcccggc tgccgccgcg     420
```

```
cgactccacc cgtggtgggg cgggggcggc tggccggcgg agcccctcgc gcggggcctg    480

tccagctctc cttcggagat cttgcaggag ctgggcaagg ggagcacgca tccgcagccc    540

ggggtgtcgc cacccgctgc cccggcggcg cccggcccca aggacggccc cggggagacg    600

gacgcgtttg gcaacagcga gggcaaagag ctggtggcct caggtgaaaa taaaataaaa    660

cagggtctgt tacctagctt ggaagatttg ctgttctata caattgctga aggacaagag    720

aaaatacctg ttcataaatt tattacagca ctcaaatcta caggattgcg aacgtctgat    780

cccaggttga aagagtgtat ggatatgtta agattaactc ttcaaacaac atcagatggt    840

gtcatgctag acaaagatct ttttaaaaaa tgtgttcaga gcaacattgt tttgttgaca    900

caagcattta gaagaaagtt tgtgattcct gactttatgt cttttacctc acacattgat    960

gagttatatg aaagtgctaa aaagcagtct ggaggaaagg ttgcagatta tattcctcaa   1020

ctggccaaat tcagtcccga tttgtggggt gtgtctgttt gtacagtaga tggacagagg   1080

cattctactg gagataccaa agttcccttc tgtcttcagt cctgtgtaaa acctttgaaa   1140

tatgccattg ctgttaatga tcttggaact gaatatgtgc atcgatatgt tggaaaagag   1200

ccgagtggac taagattcaa caaactattt ttgaatgaag atgataaacc acataatcct   1260

atggtaaatg ctggagcaat tgttgtgact tcactaataa agcaaggagt aaataatgct   1320

gaaaaatttg actatgtcat gcagtttttg aataagatgg ctggtaatga atatgttgga   1380

ttcagtaatg caacgtttca gtctgaaaga gaaagtggag atcgaaattt tgcaatagga   1440

tattacttaa aagaaaagaa gtgttttcca gaaggcacag acatggttgg tatattagac   1500

ttctacttcc agctgtgctc cattgaagtg acttgtgaat cagccagtgt gatggctgcg   1560

acactggcta atggtggttt ctgcccaatt actggtgaaa gagtactgag ccctgaagca   1620

gttcgaaata cattgagttt gatgcattcc tgtggcatgt atgacttctc agggcagttt   1680

gctttccatg ttggtcttcc tgcaaaatct ggagttgctg gggcattct tttagttgtc    1740

cccaatgtta tgggtatgat gtgctggtct cctcctctgg ataagatggg caacagtgtt   1800

aagggaattc acttttgtca cgatcttgtt tctctgtgta atttccataa ctatgataat   1860

ttgagacact ttgcaaaaaa acttgatcct cgaagagaag gtggtgatca aagggtaaag   1920

tcagtgataa atcttttgtt tgctgcatat actggagatg tgtctgcact tcgaagattt   1980

gctttgtcag ctatggacat ggaacagcgg gactatgatt ctagaacagc actccatgta   2040

gctgctgcag agggtcatgt tgaagttgtt aaatttttgc tggaagcctg caaagtaaac   2100

cctttcccca aggacaggtg gaataacact cccatggatg aagcactgca ctttggacac   2160

catgatgtat ttaaaattct ccaagaatac caagtccagt acacacctca aggagattct   2220

gacaacggga aggaaaatca aaccgtccat aagaatcttg atggattgtt gtaatggtct   2280

caaatcccaa gatttaaatc acttacctat ttaattgtgg aaaatgatta tgaagaacat   2340

gtgtatttct atctggtagt gatgtatatt ttacatttgt catttcagtg ttactggagt   2400

tttcttcatt gtgcacacag gacaaatctg atctctttgg gaaaaaatag aaataaaaca   2460

atctccctcc ataatgtgag caatattacc tcgtgcattg tataatttga tgtaaaagaa   2520

atagttacca atgctagctt gtgtggtctt ccatgattta tttgtgtttt gtgaattttc   2580

aatttatggt gatgatctgc tgatatgcat ttataaagta agctctgttg tacagtctgt   2640

ccaaatgggt caaggttgcc tttagaagca aatagtgtga ttttcaagac ttcaaataca   2700

aatttagttt aagtgtttga acaactatat gcacttacgg ttgtgtgttt aaaatgtctc   2760
```

```
tctcaccccc tagcttcatg atgtgactct taaaaaacta taatagttaa caactgttag   2820
taagatagac caattctgat tagactttat cagggaatct gtttaagata tgtttggtga   2880
ccaaaacgta tgtgtgaatg tagttataat gcttttgaaa aattttcctt tttctatatc   2940
cccttagtcc agcctctctt ctcagacatt tagctatctg cctctttcct ttagctggga   3000
aagtgagagc tggcatacta tgcagttttt atgttttcca tagtaagtca gaaaatgcct   3060
cctatttctg gcatcagaac tttgccattt gtctacagaa gacgaaccag agacaaaatt   3120
actaagtata aattagtcaa gtttatcagt ctaaaaaacg aagggatgtg caactgcagc   3180
tctttaagaa gttttttttt tttagcttct agggtaaaga taaattcaga aatgctctaa   3240
gctaccaaag ttattctgaa agtatgggaa ctgctacaac taacaaacat ttgtttccaa   3300
gcctgtcatt aagagtctgc atcaagagat ttgtcctcct tgggggacca ctggatcatt   3360
ccagatttct tgtgattttt ctattgtgta attcttggtg ggctctgtag tttaataata   3420
agaaaaaggc catttcattt taaattgtga cctataattc tttgtcttgg gttggtaatt   3480
caggattcat ttggaaagtg ggtaaaaggg gcttcaaaaa acggatagaa caggattttc   3540
taggagttac acatacattt tatcctgtca tacctcgaga taaagtggca tgttagtgag   3600
gagttctgat attaagcaca cacacacatg cacacaaatg gacttctctg aagctgtgtt   3660
tagtgaaatg agctcaagta catgaatgtt agttgttatc acatacagca aattcctttt   3720
tttttctttt tctatgagca cactctgctg cttctaaact ttacatgcct gatggcacct   3780
tactccagca gcctccaggt gctttcattt tcacttccag tctaagccag tggctcctgc   3840
cactgccctc ccattaccta gatggcacct cctttggtga aaccacggcc aatgttcctt   3900
agctgcacca ggcccgaagc tgttcccatg cttgagcttc catggggagg atgctgagtg   3960
agcagtttcc taccccgtgg atctagcaag ccatggagac aggtagcatt tgtaagatgc   4020
tgcacaggag cagcattatc cccaaagata ttacagggta gacacgtttt aactgaaatc   4080
aatcaagata actttattca aagagcagcc cgctttgtgt gactaaaatg aaacaagaca   4140
gttgaattgt gtgacttgaa gattaccaat gattttgagg cttttctata ataaaaagag   4200
gttctaacca ttatttggga acaaagagag ttttcatctt ttttcagatc aaaaccattc   4260
tgtaaaatct ttgttgttta attaaatgtg ccgttattta cccctgatgt tatttatgac   4320
tatgtgccga ttcctgctcg ggctgtttgc tgttggctgg taataatata tttgatttaa   4380
atgctgttga ctgtgctatt aactgctgcc gtcagtaaac tccaaagatc tttttgtttt   4440
ggctttagta tcatatgtgc tttttctgta tcctgagcgc tctatatgat catgttaatt   4500
taaagcttta tacacattgt tgtttttgct ggtctcatct ttggtaatat gctatacccc   4560
actgctgccc gacactgccc tttagctgca gagctggatt agctgttgac catttgatgc   4620
tgttgtctgt ctggcaggga ctgaatgacc tgatgtcaga tttagattct tcctggggat   4680
tacacagcta tgaatgtatt tgcttctaaa acctcccaaa gtgaatctaa tcttaaaact   4740
acaagttgta agtattctga aattgggaaa catttatttt aaatgcaatc aggtagtgtt   4800
gctttttaca gcataataaa tatatgtatc aaaaaaaaaa aaaaaaaaaa              4850
```

<210> SEQ ID NO 3
<211> LENGTH: 603
<212> TYPE: PRT
<213> ORGANISM: Mus musculus

<400> SEQUENCE: 3

```
Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Gly Arg Ala
    50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415
```

```
Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
            580                 585                 590

Val Tyr Arg Met Glu Ser Leu Gly Glu Arg Ser
        595                 600


<210> SEQ ID NO 4
<211> LENGTH: 4419
<212> TYPE: DNA
<213> ORGANISM: Mus musculus

<400> SEQUENCE: 4

tgagcgtcag tctcagtgcg gagctcgcgg cggccagagc aacttcggct ggctgcaggc     60

tgggcggcgg cggcggcgag ggcggcggcg ttggcggcgg gagcggcgga gctggggcca    120

caccccgtcc cggacttttt ctctttccag tcctctcccc gccgtgcggg acacggttcc    180

gggagcagag cggccgccca cgccccaagc atcctcatct gacgagcggg cgccggcggt    240

atgatgcggc tgcgaggctc ggcgatgcta cgggagctgc tcttaaggcc gcccgccgcc    300

gtcggagccg tcctgcggcg cgcgcagccc ctcggcacgc tgtgccggcg cccccggggc    360

gggagccggc cgaccgctgg cctggtggcc gctgcgcgac tccacccgtg gtggggcggg    420

ggcggccgcg cgaagggccc cggcgcgggc ggcctgtcca gttcgccctc ggagatccta    480

caggagctgg ggaagggggg tacgccgcca cagcagcagc agcagcagca gcagcagcca    540

ggggcgtcgc cacccgcagc cccgggcccc aaggacagcc cgggggagac cgacgcgttc    600

ggcaacagcg agggcaagga gatggtggcc gcgggcgaca ataaaataaa acagggtctg    660

ttacctagct tggaagattt gctgttctat acaattgcag aaggacaaga aaagatacct    720

gttcacaagt ttattacagc actcaaatct acaggattgc gaacatctga tcccaggttg    780

aaagagtgta tggatatgtt aagattaact cttcagacaa cgtcagatgg tgtcatgcta    840

gacaaagatc tttttaaaaa gtgtgttcaa agcaacattg ttttgttgac acaagcattt    900

agaagaaagt ttgtcattcc tgactttatg tcttttacct cacacatcga tgagttatat    960

gaaagtgcta aaaagcagtc tggagggaag gttgctgatt atattcctca gctggccaaa   1020

ttcagtcctg atttgtgggg tgtatctgtc tgtactgtag atgggcaaag gcattctatt   1080
```

```
ggagatacca aagttccttt ttgtcttcag tcctgtgtaa aacccctgaa atatgcaatt   1140
gctgttaatg acctgggaac tgagtatgta catcgctatg ttgggaagga gccaagtgga   1200
ttaagattca acaaactctt tttgaatgaa gatgataaac cacataatcc tatggtaaat   1260
gctggagcaa ttgttgtgac ttctctaata aagcaaggag taaataatgc tgagaagttt   1320
gactacgtga tgcaattttt gaataagatg gctggtaatg aatatgttgg attcagtaat   1380
gcaacgtttc agtctgaacg agaaagtgga gatcgaaatt ttgcaatagg atattactta   1440
aaagaaaaga agtgttttcc agaaggcaca gacatggttg ggatactaga tttttacttc   1500
cagctgtgct ctattgaagt gacatgtgaa tcagcaagtg tgatggctgc caccttggct   1560
aatggtggtt tctgcccaat tactggtgaa agagtcctca gtcctgaggc agttcggaat   1620
acactgagct tgatgcattc ttgtggcatg tatgacttct cagggcagtt tgcgttccat   1680
gttggtcttc ctgcaaaatc tggagttgct gggggtattc ttttagttgt ccccaacgtc   1740
atgggcatga tgtgttggtc tcctcctctt gacaagatgg gcaacagtgt taagggaatt   1800
cacttttgtc acgatcttgt ttctctgtgt aacttccata actatgataa tttgagacac   1860
tttgcaaaaa aacttgatcc tcggagagaa ggaggtgatc aaaggcattc ctttggacca   1920
ttggactatg agagtctcca gcaagaactt gctttaaaag acacagtatg gaaaaaagtg   1980
tcacctgagt caagtgacga cacctctaca actgtagtat atagaatgga gagtctgggg   2040
gagaggagct agagatgggc tctagctaca gaacagaacg attctccttt taacatcgga   2100
aacatcttta ggcttttgtt tcttgtttat ctttccaaac taagtattta ttcaagtatt   2160
ctattgttat cagttttggg tactggagcc ataaatttaa aaaaaggttc tgttttggtt   2220
tggttttttt tcgcttgtaa tctttgtata aaaaacattt gttatttttt aaaagagcat   2280
ttacaaataa agcaaatttg ctttattttt taaaactttt ttaaaaaatg caatttcctt   2340
aattacatta aaaatttaac tataaaattt ggtaaccaca ttgtttttct tagttctgaa   2400
gcctgcatat taaactgagg cgtattgttg gatttgtctt ttcctttcca gttttataat   2460
tgataggcta tattggtagt gacagaaagt acttccatgc taaatataaa actaaaaagg   2520
caaagtaatc aaaattattt aaaagagtac tagattataa aattagcttt agtttacaca   2580
tatgccagtt atagcggtag attggctttg aatatttaaa atgcaaatac ttttaaatat   2640
gtcttttttt ttgtttgaaa agttctgtcc tgtcagaatc acaatgtatt aggaatgttt   2700
cacatcactg aaacactcca gccaaagaat tgcagatgtg tgagaatggc atgccctgtt   2760
atttaaaagc tacaatggtt agttgctcag aaaaagagtc aataactatc ttcaaaatgg   2820
attgtatttt catattcttc atgtaatttt tttgttgtat ttaagtatga acggtaaatt   2880
ttgctttttt agcttttagt aattttatta tgtttcataa gtgctaatga atattttgtg   2940
ataattataa catctcataa attttgttct ttttgaactt ttattagcat acttatgaaa   3000
tgaatatagt ttgaaggtgt taagtataca actaaaatat ttgttgaatt ggaatgcttc   3060
tgtttatttt taaaatgcaa tattgagaat caaaactttt ttcaagagaa tcataggttc   3120
cattttatct cgtcataaac agatatacat atttttagaa tctatcttgg caaaatgata   3180
ctaatgttct gcaggattta tttacatgtc ttccttcgtg tattttgttt ttctcacaat   3240
ttcaagtttg gtttttcaaa ttcactttta aacttgtaaa ttttgggcaa gtggttgaga   3300
atgaaagcct tattgctttt taaattatgg cacatgtata gtagagcaga ttctgtaact   3360
aaagaaagtg cgggaaaaat agttcactga taggctaagt aagatacagg aaagtcctga   3420
tggtctgatt tgaaactggg aactctgata ttaagaaaag ggttcttctc agaagttcga   3480
```

```
ccttaaagcc tttgggctaa cttaagtatt actatttgta tttaaataat tacatggtgg   3540
gttttagaaa ggctggctgt cctgcccctt tggtgttcat atgcattccc cagcctgatg   3600
ctttaaaagc cttgccactg ccctgcttgt ggacactaat catctctttt tcttgtatcc   3660
agagtgactg tgattcaggt aattgagcac catgattgga aaaaagattt taggtttatt   3720
tcccctccat ttttatgtgt acattttgtt gtttcattca gaagttggat ttactttaca   3780
aaatgactta attttcatat tgtggtcatg tttgtgtaaa cttcaaacta ttttgttaat   3840
ttttggcact tcctatatat aattctagta atgcttgaat gtacacttaa atatgaagta   3900
ggattaagtc agctgctgtg tttaaagaat gctgttaaga acaagcattc aaaactgtat   3960
aggaaggtat tagcttaaga gtaggtaaga taccgtgact gtatctgcag acaagaagag   4020
gaaagaaaag ctttgccagt ttgtggattt atcttaattc ccttcagtat attcaatctc   4080
ttttcaaata aagctctttg agaagtaccc agtattgttg ggtttaattt ttcctactat   4140
tattgattct tgatattcaa gcatttacat gacagcgtat ttttttcttt tcctttttc    4200
tgtttatttt tttttgctat cattaacatt tcatttgaaa tgcatactct tcttgaaata   4260
ttttgttttt agcataaatg ttgtgcattt tatcttagtg tttggattaa aacatttgtg   4320
ttgttgagct ttcttcattt gctttgtata tttaataatg tatctttatt ttccagtatg   4380
cctatttttt gtattgtaca ataaatttat tttaagctg                          4419
```

<210> SEQ ID NO 5
<211> LENGTH: 669
<212> TYPE: PRT
<213> ORGANISM: Homo sapiens

<400> SEQUENCE: 5

```
Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205
```

```
Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
                565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
        595                 600                 605

Cys Lys Val Asn Pro Phe Pro Lys Asp Arg Trp Asn Asn Thr Pro Met
    610                 615                 620
```

```
Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
                645                 650                 655

Glu Asn Gln Thr Val His Lys Asn Leu Asp Gly Leu Leu
            660                 665


<210> SEQ ID NO 6
<211> LENGTH: 4509
<212> TYPE: DNA
<213> ORGANISM: Homo sapiens

<400> SEQUENCE: 6

agtgcggagc cttaggcgga gcgaagagaa ccggtcgcgg caatcctagc gcgcagcagc      60

agcagcagca gcagcagcag cagcagcagc agcagcagca cccgcatccg ctgcgggagt     120

ccgagccgga accacaccca agtagctgcc ctttcctctt ctgtcatctc accgccccac     180

cacagaccgc gttccccgag gaaaccggcc gcccacgccc ggagcatcct cccctgttga     240

gcgggcgctg acggacccgg cggcatgatg cggctgcgag gctcggggat gctgcgggac     300

ctgctcctgc ggtcgcccgc cggcgtgagc gcgactctgc ggcgggcaca gcccttggtc     360

accctgtgcc ggcgtccccg aggcggggga cggccggccg cgggcccggc tgccgccgcg     420

cgactccacc cgtggtgggg cgggggcggc tggccggcgg agcccctcgc gcggggcctg     480

tccagctctc cttcggagat cttgcaggag ctgggcaagg ggagcacgca tccgcagccc     540

ggggtgtcgc cacccgctgc cccggcggcg cccggcccca aggacggccc cggggagacg     600

gacgcgtttg gcaacagcga gggcaaagag ctggtggcct caggtgaaaa taaaataaaa     660

cagggtctgt tacctagctt ggaagatttg ctgttctata caattgctga aggacaagag     720

aaaatacctg ttcataaatt tattacagca ctcaaatcta caggattgcg aacgtctgat     780

cccaggttga aagagtgtat ggatatgtta agattaactc ttcaaacaac atcagatggt     840

gtcatgctag acaaagatct tttaaaaaaa tgtgttcaga gcaacattgt tttgttgaca     900

caagcattta gaagaaagtt tgtgattcct gactttatgt cttttacctc acacattgat     960

gagttatatg aaagtgctaa aaagcagtct ggaggaaagg ttgcagatta tattcctcaa    1020

ctggccaaat tcagtcccga tttgtggggt gtgtctgttt gtacagtaga tggacagagg    1080

cattctactg gagataccaa agttcccttc tgtcttcagt cctgtgtaaa acctttgaaa    1140

tatgccattg ctgttaatga tcttggaact gaatatgtgc atcgatatgt tggaaaagag    1200

ccgagtggac taagattcaa caaactattt ttgaatgaag atgataaacc acataatcct    1260

atggtaaatg ctggagcaat tgttgtgact tcactaataa agcaaggagt aaataatgct    1320

gaaaaatttg actatgtcat gcagtttttg aataagatgg ctggtaatga atatgttgga    1380

ttcagtaatg caacgtttca gtctgaaaga gaaagtggag atcgaaattt tgcaatagga    1440

tattacttaa aagaaaagaa gtgttttcca gaaggcacag acatggttgg tatattagac    1500

ttctacttcc agctgtgctc cattgaagtg acttgtgaat cagccagtgt gatggctgcg    1560

acactggcta atggtggttt ctgcccaatt actggtgaaa gagtactgag ccctgaagca    1620

gttcgaaata cattgagttt gatgcattcc tgtggcatgt atgacttctc agggcagttt    1680

gctttccatg ttggtcttcc tgcaaaatct ggagttgctg gggcattct tttagttgtc     1740

cccaatgtta tgggtatgat gtgctggtct cctcctctgg ataagatggg caacagtgtt    1800

aagggaattc acttttgtca cgatcttgtt tctctgtgta atttccataa ctatgataat    1860
```

```
ttgagacact ttgcaaaaaa acttgatcct cgaagagaag gtggtgatca aaggcattcc   1920
tttggaccat tggactatga aagtctccaa caagaacttg ctttaaaaga gacagtatgg   1980
aaaaaagtgt cacctgagtc aaatgaggac atctctacaa ctgtagtata tagaatggaa   2040
agtctgggag agaaaagcta aagaaatggg ttctagtttc agaatgtttc ttcatttaat   2100
ctttcaaaca tctttagctt tttttgcaa gttataaata tttatttgag gtattttttg   2160
ttctcaatct tgggtgctgg agccataaag cttttttttc cttttaatct ttgtataaag   2220
gcagtagatt aagaagtgca tttgttggtc tttaaaaagt atttacaagt acataaattt   2280
gctttatttt taaaaataca aaaaggaaaa atttaaattt tttttgatgt aattaaaatg   2340
ttaactatgt ggtcagataa tcccatttta caatagtaac agaaaattgt aattcttagt   2400
tctaaaattc acaaattaaa ctcataagtt ttgttgcatt ttgtttttc ttttccattt   2460
ttaaaactaa tgtgatgtct ttagtggcaa tagaaggtac ttctatgcta aatacaaaac   2520
taaaaaggca aaataatgaa ccccaaatta ttttatttaa aatagcagtg gattataaaa   2580
ttagcttgtg tttacattta tgccattttt ggtgatagat tggctttaca ttttaaaaaa   2640
tttatttaaa aatttatcaa atgctttaaa atatgactcc tacttttttt attttgcaac   2700
tcctctgttc tgtcagagtt gttatataca ggagtgtctt atgttactaa aacattccag   2760
ccaaagaatt tcagatgtga gataatgatg tttcatcaat aaaaagctat aatggttagt   2820
tactcagaag gagaaacagt gagtgtcttc aagtgaattg ttcacctaaa caattttatt   2880
ttcatattat ccacataact ttttctatgt tatatttaaa tatgaatggc aaattttggt   2940
ttttagcttt tacattttat tatcttaatt ttataaatgc taatatttct tttgtgataa   3000
gttatagcat ctcataaagt ttgttctatt tgaagttttt tagagtactt gagaaatgaa   3060
tttagtctgc aggtagtaag tatgctacta aaatacgtta gatctaaatc cttttatttg   3120
gtataaaaat gcaatattga gaatcaaaac ttgtttttaa gagaactata gattctacac   3180
aacctgattt caagtaatta ttcatagtat ttatagttgt cttggcaaag tgattgtaaa   3240
attctgtagg acctattcac acttcttcct tcttccatat acttctctgg ttttccccat   3300
agttccccta taatttcaag tttgttgaaa cctgttaatt ttagtggggg attagaagaa   3360
aaacttggtg gtttcttagc atgatggtgt atgtatgtgg taatggaaag tctgtaaaag   3420
taaatatagt gtagcaaaaa agatttcact gagtatttta gatactagtg caaataaaga   3480
tagaaaatct tgatcataat gtcttaagtt tgggaactgt gatattaaga aaagaaattc   3540
ccttctagag gtgctggcca aaaagccttt tgggctaact taagtattaa atttatatat   3600
ttaaataatt atattttaag ttgtagagga ttttcccaag gattttatgc ttacttgaat   3660
gttctttgaa tgttcagatg catatcctaa ctggatgctt ctcaaggcct tactgcatat   3720
ttgtgttgca tatttatgtt agttgcacca gggccatttg tagtttgggc aaccgaatgc   3780
cttaattgga aaaaaggcat tgtggtttcc cctatgatct aaattgttac attttaccat   3840
ttcattccga agttggtttt actttattaa atgaagattt agttttcata tcgtatacat   3900
agctgtatag atttcaaaat taggttgtta atttgtgtca cttactattt ttgtgttggt   3960
aatgctttaa atgcatactt aaaaatgaag tactgttatc taagctactg tgtttagaaa   4020
atgttaagaa tgagcagaaa tttttataga aaagtataaa cggaagaaga gataagatac   4080
tgcgaatagg ccctcaaact taaaaaagaa aaaactttgc cagttttaag gacatatttt   4140
gattctttca gtattcttaa caccttttta aacaaagttc ttgatagtac ccactattat   4200
tgggtttgtt ttatgccatt attgattctt gatattcaag catttacaat gtagcatatt   4260
```

```
tgattttctt ttttctttct ttttttggca tcattaacat ttcatttgaa atgcatattg   4320

ttcttgaagt actttgtttt tagcataaat gttgtgcatt ttatcttagt gtttggatga   4380

aaacatttgt gttgtttagc tttcatttgc tttgtatatt taataatgta cctttatttt   4440

ccagtatgcc tacattttgt attgcacaat aaatttattt taagctgaaa aaaaaaaaaa   4500

aaaaaaaaa                                                           4509


<210> SEQ ID NO 7
<211> LENGTH: 674
<212> TYPE: PRT
<213> ORGANISM: Mus musculus

<400> SEQUENCE: 7

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Gly Arg Ala
    50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320
```

```
Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Ala Glu Gly His Val Glu Val Val Lys
        595                 600                 605

Phe Leu Leu Glu Ala Cys Lys Val Asn Pro Phe Pro Lys Asp Arg Trp
    610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu
```

<210> SEQ ID NO 8
<211> LENGTH: 4974
<212> TYPE: DNA
<213> ORGANISM: Mus musculus

<400> SEQUENCE: 8

```
tgagcgtcag tctcagtgcg gagctcgcgg cggccagagc aacttcggct ggctgcaggc      60

tgggcggcgg cggcggcgag ggcggcggcg ttggcggcgg gagcggcgga gctggggcca     120
```

```
caccccgtcc cggacttttt ctctttccag tcctctcccc gccgtgcggg acacggttcc    180
gggagcagag cggccgccca cgccccaagc atcctcatct gacgagcggg cgccggcggt    240
atgatgcggc tgcgaggctc ggcgatgcta cgggagctgc tcttaaggcc gcccgccgcc    300
gtcggagccg tcctgcggcg cgcgcagccc ctcggcacgc tgtgccggcg cccccggggc    360
gggagccggc cgaccgctgg cctggtggcc gctgcgcgac tccacccgtg gtggggcggg    420
ggcggccgcg cgaagggccc cggcgcgggc ggcctgtcca gttcgccctc ggagatccta    480
caggagctgg ggaagggggg tacgccgcca cagcagcagc agcagcagca gcagcagcca    540
ggggcgtcgc cacccgcagc cccgggcccc aaggacagcc cgggggagac cgacgcgttc    600
ggcaacagcg agggcaagga gatggtggcc gcgggcgaca ataaaataaa acagggtctg    660
ttacctagct tggaagattt gctgttctat acaattgcag aaggacaaga aaagatacct    720
gttcacaagt ttattacagc actcaaatct acaggattgc gaacatctga tcccaggttg    780
aaagagtgta tggatatgtt aagattaact cttcagacaa cgtcagatgg tgtcatgcta    840
gacaaagatc tttttaaaaa gtgtgttcaa agcaacattg ttttgttgac acaagcattt    900
agaagaaagt ttgtcattcc tgactttatg tcttttacct cacacatcga tgagttatat    960
gaaagtgcta aaaagcagtc tggagggaag gttgctgatt atattcctca gctggccaaa   1020
ttcagtcctg atttgtgggg tgtatctgtc tgtactgtag atgggcaaag gcattctatt   1080
ggagatacca aagttccttt ttgtcttcag tcctgtgtaa aacccctgaa atatgcaatt   1140
gctgttaatg acctgggaac tgagtatgta catcgctatg ttgggaagga gccaagtgga   1200
ttaagattca acaaactctt tttgaatgaa gatgataaac cacataatcc tatggtaaat   1260
gctggagcaa ttgttgtgac ttctctaata aagcaaggag taaataatgc tgagaagttt   1320
gactacgtga tgcaattttt gaataagatg gctggtaatg aatatgttgg attcagtaat   1380
gcaacgtttc agtctgaacg agaaagtgga gatcgaaatt ttgcaatagg atattactta   1440
aaagaaaaga agtgttttcc agaaggcaca gacatggttg ggatactaga tttttacttc   1500
cagctgtgct ctattgaagt gacatgtgaa tcagcaagtg tgatggctgc caccttggct   1560
aatggtggtt tctgcccaat tactggtgaa agagtcctca gtcctgaggc agttcggaat   1620
acactgagct tgatgcattc ttgtggcatg tatgacttct cagggcagtt tgcgttccat   1680
gttggtcttc ctgcaaaatc tggagttgct gggggtattc ttttagttgt ccccaacgtc   1740
atgggcatga tgtgttggtc tcctcctctt gacaagatgg gcaacagtgt taagggaatt   1800
cacttttgtc acgatcttgt ttctctgtgt aacttccata actatgataa tttgagacac   1860
tttgcaaaaa aacttgatcc tcggagagaa ggaggtgatc aaagggtgaa gtcggtgata   1920
aaccttctgt ttgccgcata cactggagat gtgtctgccc tccgaaggtt tgctctgtca   1980
gccatggaca tggagcagcg ggattatgac tccagaacag ccctccatgt cgcagcagca   2040
gagggtcatg ttgaagttgt caagtttttg ctggaagctt gcaaagtaaa ccctttcccc   2100
aaggacaggt ggaataatac ccccatggat gaagcactac actttggaca ccatgatgtt   2160
tttaaaatcc ttcaggaata ccaagttcag tacacacctc aaggggattc tgatgatgga   2220
aagggaaacc agactgtcca caagaatctc gacgggttgc tataatggtc tgcaccccaa   2280
gacttccatt acttacctag tcattgtgga acatgactat ggagagcatt gtatatttct   2340
atctggtagt aatgtgtatt tacaacatct gtcactgcag tgttaccgga gcttccttca   2400
ttgtgcgcac acgacaaatc tgagttcttt gggaaaaaaa tagaaatgaa gcagcctccc   2460
ttcataatgt gagcaatagt tacctcgtgc attgtacaat gtggtgtaaa agagtagtta   2520
```

```
ccaatgccag ctgaactgtg tggtcttcat ggtttgcgtt ctgtacattt tcaagccctg   2580
gtgatgatac gctcatatgc acttaggagt gagctttgtt gtacagtctg tccacggggt   2640
cgatgctgtt attaggtgaa aatagtgtga tctttaagac tttaaataca gatttagttt   2700
tgagtgtttg agagaccact acacttgtat ggttgagtgt ttaaaatgtc tatcaccctc   2760
acttcagagt gtgactcttt aaatattaaa atagatacta actgttcata gaacaggccg   2820
attctgatta gattttatca gggaatctgt taagatatgt ttggtgacca aaacgtatgt   2880
gtgaatatag ttctagcact tttaaatttt tcctttccat acaacgcttg ggccagcctc   2940
tctgtgctgc gtggctgtcg gtccccctca gctgggaaag agagcactgg ctcactgtgc   3000
agttttcatg tttcctcagc aagccatcaa gcctcacatc tctaccatca gagatagagc   3060
ttggccattt atctaaggaa gatgagccaa aattatgaca tctaaaataa tcgtcagtct   3120
taagagtaaa gacagcgaaa ctgcacactt ataagttctt ttcagcttct acaataaaga   3180
aaagttcaga aatgctttca gttaccaaag ttataacgat atatttagga aaagctacaa   3240
ataacactta ctttgaatcc tgctgtcaaa tgtctgcatc aagatagcac ccctttgtgg   3300
gaggccctga gtatcttctc ttcctctact gcctaactgt tggtgggctg tatcattcaa   3360
taagatcact tcattttcaa cttagaccca ccgtttcttt tttgttgttt tgttttgttt   3420
ggtttggttt ggttgggttg ggttgttgtt tttggttttt tcgagacagg gtttctctgt   3480
gtagccctgg ctgtcctgga actcactttg tagaccaggc tggccttgaa ctcagaaatc   3540
cgcctgcctc tgcctcccga gtgctgggat taaaggtgca aactaccacg cctggcagac   3600
ccaccatttc tttgctttgg aaaggtaatt tatgattaac ttagataata ggtaaaagcg   3660
accttacaaa aaacataatt atctaggagt cccacatact ggacctaccc tattatacct   3720
ccaagagata aagggtatgt tagtgaggac ttttgcacac aagtgcatgc acacttggca   3780
tacacacaca cacacacaca cacacacaca cacacacaca cacacggact tcttggaaac   3840
tgctttatga agaaactgct ttatgaaata agcaaaattc tcaagtgcac agatactagc   3900
agttatgaca gtaatacagc gtcttctgtg accctcacta cctgcactgc ttgcatccct   3960
gctttatgcc tggtggcaca ttattcaccc ggtaacctcc agctgctttg atcctgtttc   4020
agtcaaagtc agcttcagcc accccctcca ttccctagcc agctccaccc ttgatgaaac   4080
tgtggctaat gttccttcac taggacaggc accatgagtg tgtttctaag ttccagagtc   4140
tgtggggagg atggtgggtg ggcagccagc cctgttgcta tgttgcttct tccacacccc   4200
ctcaagacag gtgcataggt ggcactggga acatcctacg cagggacaac ctccaaaatt   4260
aatgggtgaa catggttttt ttggaatcaa ctgagataat gctatttcaa tagcggctgg   4320
ctttttgtga ttcagtaact taaatattgc cagtgactga ggatcccctc cagtcatggt   4380
tctgtatatt ctttgagaca ggtgttttca tcttctctca gctcagtgct gttttgtaca   4440
gtctctgtgg cttggttgag tatgctcttt cctgtgccag gtcttgctct ggctgttcgc   4500
tactggctga taataacaag gaccctgtgt gtgtgtgaat gagccgctaa ctgctaccat   4560
ctgtaaactc caaagatctg tttgttttgg ctttacaatc ttagctaatt tttctgtatc   4620
ctggaaccat tacatgatca tgttgctttg aagatctttt tatgccactg tttctgctgt   4680
cttggttctg acacccctgt ctggtgatat gctatacccc agtgctgcct acacgtgctt   4740
tagctgtaga gctgggtata ctgttgatcc agctgtccgt cagggacttg ataacctgat   4800
gtttgatgta gatccctgct ggggagtcca caactatgaa tgtatttact tccaacattt   4860
```

```
cccaaaatga aaactataaa ttgcaagtat tctggaattg ggaaatactt attttaaatg   4920

agatcaggta gtgttgcttt ttacagcata ataaatatgt gtattgaaaa caaa         4974


<210> SEQ ID NO 9
<211> LENGTH: 669
<212> TYPE: PRT
<213> ORGANISM: Mus musculus

<400> SEQUENCE: 9

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Glu Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350
```

```
Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Lys Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Glu Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
                565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
        595                 600                 605

Cys Lys Val Asn Pro Phe Pro Lys Asp Arg Trp Asn Asn Thr Pro Met
    610                 615                 620

Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
                645                 650                 655

Glu Asn Gln Thr Val His Lys Asn Leu Asp Gly Leu Leu
            660                 665
```

<210> SEQ ID NO 10
<211> LENGTH: 674
<212> TYPE: PRT
<213> ORGANISM: Homo sapiens

<400> SEQUENCE: 10

```
Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Gly Arg Ala
    50                  55                  60
```

```
Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Glu Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Lys Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Glu Asn Thr Leu Ser Leu
    450                 455                 460

Met His Ser Cys Gly Met Tyr Asp Phe Ser Gly Gln Phe Ala Phe His
465                 470                 475                 480
```

```
Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Ala Glu Gly His Val Glu Val Val Lys
        595                 600                 605

Phe Leu Leu Glu Ala Cys Lys Val Asn Pro Phe Pro Lys Asp Arg Trp
    610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu


<210> SEQ ID NO 11
<211> LENGTH: 598
<212> TYPE: PRT
<213> ORGANISM: Mus musculus

<400> SEQUENCE: 11

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175
```

```
Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Glu Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Lys Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Glu Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575
```

```
Pro Glu Ser Asn Glu Asp Ile Ser Thr Thr Val Val Tyr Arg Met Glu
            580                 585                 590

Ser Leu Gly Glu Lys Ser
        595


<210> SEQ ID NO 12
<211> LENGTH: 603
<212> TYPE: PRT
<213> ORGANISM: Homo sapiens

<400> SEQUENCE: 12

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Gly Arg Ala
    50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Glu Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350
```

```
Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Lys Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Glu Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
            580                 585                 590

Val Tyr Arg Met Glu Ser Leu Gly Glu Arg Ser
        595                 600


<210> SEQ ID NO 13
<211> LENGTH: 20
<212> TYPE: PRT
<213> ORGANISM: Artificial
<220> FEATURE:
<223> OTHER INFORMATION: Anti-GAC antibody recognition sequence

<400> SEQUENCE: 13

Asn Phe His Asn Tyr Asp Asn Leu Arg His Phe Ala Lys Lys Leu Asp
1               5                   10                  15

Pro Arg Arg Glu
            20


<210> SEQ ID NO 14
<211> LENGTH: 2820
<212> TYPE: DNA
<213> ORGANISM: Artificial
<220> FEATURE:
<223> OTHER INFORMATION: cDNA coding sequence for mutated human KGA

<400> SEQUENCE: 14

agtgcggagc cttaggcgga gcgaagagaa ccggtcgcgg caatcctagc gcgcagcagc      60

agcagcagca gcagcagcag cagcagcagc agcagcagca cccgcatccg ctgcgggagt     120

ccgagccgga accacaccca agtagctgcc ctttcctctt ctgtcatctc accgccccac     180
```

```
cacagaccgc gttccccgag gaaaccggcc gcccacgccc ggagcatcct cccctgttga    240
gcgggcgctg acggacccgg cggcatgatg cggctgcgag gctcggggat gctgcgggac    300
ctgctcctgc ggtcgcccgc cggcgtgagc gcgactctgc ggcgggcaca gcccttggtc    360
accctgtgcc ggcgtccccg aggcggggga cggccggccg cgggcccggc tgccgccgcg    420
cgactccacc cgtggtgggg cgggggcggc tggccggcgg agcccctcgc gcggggcctg    480
tccagctctc cttcggagat cttgcaggag ctgggcaagg ggagcacgca tccgcagccc    540
ggggtgtcgc cacccgctgc cccggcggcg cccggcccca aggacggccc cggggagacg    600
gacgcgtttg gcaacagcga gggcaaagag ctggtggcct caggtgaaaa taaaataaaa    660
cagggtctgt tacctagctt ggaagatttg ctgttctata caattgctga aggacaagag    720
aaaatacctg ttcataaatt tattacagca ctcaaatcta caggattgcg aacgtctgat    780
cccaggttga aagagtgtat ggatatgtta agattaactc ttcaaacaac atcagatggt    840
gtcatgctag acaaagatct tttaaaaaaa tgtgttcaga gcaacattgt tttgttgaca    900
caagcattta gaagaaagtt tgtgattcct gactttatgt cttttacctc acacattgat    960
gagttatatg aaagtgctaa aaagcagtct ggaggaaagg ttgcagatta tattcctcaa   1020
ctggccaaat tcagtcccga tttgtggggt gtgtctgttt gtacagtaga tggacagagg   1080
cattctactg gagataccaa agttcccttc tgtcttcagt cctgtgtaaa acctttgaaa   1140
tatgccattg ctgttaatga tcttggaact gaatatgtgc atcgatatgt tggagaggag   1200
ccgagtggac taagattcaa caaactattt ttgaatgaag atgataaacc acataatcct   1260
atggtaaatg ctggagcaat tgttgtgact tcactaataa agcaaggagt aaataatgct   1320
gaaaaatttg actatgtcat gcagtttttg aataagatgg ctggtaatga atatgttgga   1380
ttcagtaatg caacgtttca gtctgaaaga gaaagtggaa agcgaaattt tgcaatagga   1440
tattacttaa aagaaaagaa gtgttttcca gaaggcacag acatggttgg tatattagac   1500
ttctacttcc agctgtgctc cattgaagtg acttgtgaat cagccagtgt gatggctgcg   1560
acactggcta atggtggttt ctgcccaatt actggtgaaa gagtactgag ccctgaagca   1620
gttgaaaata cattgagttt gatgcattcc tgtggcatgt atgacttctc agggcagttt   1680
gctttccatg ttggtcttcc tgcaaaatct ggagttgctg gggcattctt tttagttgtc   1740
cccaatgtta tgggtatgat gtgctggtct cctcctctgg ataagatggg caacagtgtt   1800
aagggaattc acttttgtca cgatcttgtt tctctgtgta atttccataa ctatgataat   1860
ttgagacact ttgcaaaaaa acttgatcct cgaagagaag gtggtgatca aagggtaaag   1920
tcagtgataa atcttttgtt tgctgcatat actggagatg tgtctgcact tcgaagattt   1980
gctttgtcag ctatggacat ggaacagcgg gactatgatt ctagaacagc actccatgta   2040
gctgctgcag agggtcatgt tgaagttgtt aaatttttgc tggaagcctg caaagtaaac   2100
cctttcccca aggacaggtg gaataacact cccatggatg aagcactgca ctttggacac   2160
catgatgtat ttaaaattct ccaagaatac caagtccagt acacacctca aggagattct   2220
gacaacggga aggaaaatca aaccgtccat aagaatcttg atggattgtt gtaatggtct   2280
caaatcccaa gatttaaatc acttacctat ttaattgtgg aaaatgatta tgaagaacat   2340
gtgtatttct atctggtagt gatgtatatt ttacatttgt catttcagtg ttactggagt   2400
tttcttcatt gtgcacacag gacaaatctg atctctttgg gaaaaaatag aaataaaaca   2460
atctccctcc ataatgtgag caatattacc tcgtgcattg tataatttga tgtaaaagaa   2520
atagttacca atgctagctt gtgtggtctt ccatgattta tttgtgtttt gtgaattttc   2580
```

```
aatttatggt gatgatctgc tgatatgcat ttataaagta agctctgttg tacagtctgt   2640

ccaaatgggt caaggttgcc tttagaagca aatagtgtga ttttcaagac ttcaaataca   2700

aatttagttt aagtgtttga acaactatat gcacttacgg ttgtgtgttt aaaatgtctc   2760

tctcaccccc tagcttcatg atgtgactct taaaaaacta taatagttaa caactgttag   2820


<210> SEQ ID NO 15
<211> LENGTH: 4509
<212> TYPE: DNA
<213> ORGANISM: Artificial
<220> FEATURE:
<223> OTHER INFORMATION: cDNA coding sequence for mutated human GAC

<400> SEQUENCE: 15

agtgcggagc cttaggcgga gcgaagagaa ccggtcgcgg caatcctagc gcgcagcagc     60

agcagcagca gcagcagcag cagcagcagc agcagcagca cccgcatccg ctgcgggagt    120

ccgagccgga accacaccca agtagctgcc ctttcctctt ctgtcatctc accgccccac    180

cacagaccgc gttccccgag gaaaccggcc gcccacgccc ggagcatcct cccctgttga    240

gcgggcgctg acggacccgg cggcatgatg cggctgcgag gctcggggat gctgcgggac    300

ctgctcctgc ggtcgcccgc cggcgtgagc gcgactctgc ggcgggcaca gcccttggtc    360

accctgtgcc ggcgtccccg aggcggggga cggccggccg cgggcccggc tgccgccgcg    420

cgactccacc cgtggtgggg cgggggcggc tggccggcgg agcccctcgc gcggggcctg    480

tccagctctc cttcggagat cttgcaggag ctgggcaagg ggagcacgca tccgcagccc    540

ggggtgtcgc cacccgctgc cccggcggcg cccggcccca aggacggccc cggggagacg    600

gacgcgtttg gcaacagcga gggcaaagag ctggtggcct caggtgaaaa taaaataaaa    660

cagggtctgt tacctagctt ggaagatttg ctgttctata caattgctga aggacaagag    720

aaaatacctg ttcataaatt tattacagca ctcaaatcta caggattgcg aacgtctgat    780

cccaggttga aagagtgtat ggatatgtta agattaactc ttcaaacaac atcagatggt    840

gtcatgctag acaaagatct tttaaaaaaa tgtgttcaga gcaacattgt tttgttgaca    900

caagcattta gaagaaagtt tgtgattcct gactttatgt cttttacctc acacattgat    960

gagttatatg aaagtgctaa aaagcagtct ggaggaaagg ttgcagatta tattcctcaa   1020

ctggccaaat tcagtcccga tttgtggggt gtgtctgttt gtacagtaga tggacagagg   1080

cattctactg gagataccaa agttcccttc tgtcttcagt cctgtgtaaa acctttgaaa   1140

tatgccattg ctgttaatga tcttggaact gaatatgtgc atcgatatgt tggaaaagag   1200

ccgagtggac taagattcaa caaactattt ttgaatgaag atgataaacc acataatcct   1260

atggtaaatg ctggagcaat tgttgtgact tcactaataa agcaaggagt aaataatgct   1320

gaaaaatttg actatgtcat gcagtttttg aataagatgg ctggtaatga atatgttgga   1380

ttcagtaatg caacgtttca gtctgaaaga gaaagtggaa agcgaaattt tgcaatagga   1440

tattacttaa aagaaaagaa gtgttttcca gaaggcacag acatggttgg tatattagac   1500

ttctacttcc agctgtgctc cattgaagtg acttgtgaat cagccagtgt gatggctgcg   1560

acactggcta atggtggttt ctgcccaatt actggtgaaa gagtactgag ccctgaagca   1620

gttgaaaata cattgagttt gatgcattcc tgtggcatgt atgacttctc agggcagttt   1680

gctttccatg ttggtcttcc tgcaaaatct ggagttgctg gggcattct tttagttgtc    1740

cccaatgtta tgggtatgat gtgctggtct cctcctctgg ataagatggg caacagtgtt   1800

aagggaattc acttttgtca cgatcttgtt tctctgtgta atttccataa ctatgataat   1860
```

```
ttgagacact ttgcaaaaaa acttgatcct cgaagagaag gtggtgatca aaggcattcc   1920
tttggaccat tggactatga aagtctccaa caagaacttg ctttaaaaga gacagtatgg   1980
aaaaaagtgt cacctgagtc aaatgaggac atctctacaa ctgtagtata tagaatggaa   2040
agtctgggag agaaaagcta aagaaatggg ttctagtttc agaatgtttc ttcatttaat   2100
ctttcaaaca tctttagctt ttttttgcaa gttataaata tttatttgag gtattttttg   2160
ttctcaatct tgggtgctgg agccataaag cttttttttc cttttaatct ttgtataaag   2220
gcagtagatt aagaagtgca tttgttggtc tttaaaaagt atttacaagt acataaattt   2280
gctttatttt taaaaataca aaaaggaaaa atttaaattt tttttgatgt aattaaaatg   2340
ttaactatgt ggtcagataa tcccatttta caatagtaac agaaaattgt aattcttagt   2400
tctaaaattc acaaattaaa ctcataagtt ttgttgcatt ttgttttttc ttttccattt   2460
ttaaaactaa tgtgatgtct ttagtggcaa tagaaggtac ttctatgcta aatacaaaac   2520
taaaaaggca aaataatgaa ccccaaatta ttttatttaa aatagcagtg gattataaaa   2580
ttagcttgtg tttacattta tgccattttt ggtgatagat tggctttaca ttttaaaaaa   2640
tttatttaaa aatttatcaa atgctttaaa atatgactcc tacttttttt attttgcaac   2700
tcctctgttc tgtcagagtt gttatataca ggagtgtctt atgttactaa aacattccag   2760
ccaaagaatt tcagatgtga gataatgatg tttcatcaat aaaaagctat aatggttagt   2820
tactcagaag gagaaacagt gagtgtcttc aagtgaattg ttcacctaaa caattttatt   2880
ttcatattat ccacataact ttttctatgt tatatttaaa tatgaatggc aaattttggt   2940
ttttagcttt tacattttat tatcttaatt ttataaatgc taatatttct tttgtgataa   3000
gttatagcat ctcataaagt ttgttctatt tgaagttttt tagagtactt gagaaatgaa   3060
tttagtctgc aggtagtaag tatgctacta aaatacgtta gatctaaatc cttttatttg   3120
gtataaaaat gcaatattga gaatcaaaac ttgtttttaa gagaactata gattctacac   3180
aacctgattt caagtaatta ttcatagtat ttatagttgt cttggcaaag tgattgtaaa   3240
attctgtagg acctattcac acttcttcct tcttccatat acttctctgg ttttccccat   3300
agttccccta taatttcaag tttgttgaaa cctgttaatt ttagtggggg attagaagaa   3360
aaacttggtg gtttcttagc atgatggtgt atgtatgtgg taatggaaag tctgtaaaag   3420
taaatatagt gtagcaaaaa agatttcact gagtatttta gatactagtg caaataaaga   3480
tagaaaatct tgatcataat gtcttaagtt tgggaactgt gatattaaga aaagaaattc   3540
ccttctagag gtgctggcca aaaagccttt tgggctaact taagtattaa atttatatat   3600
ttaaataatt atattttaag ttgtagagga ttttcccaag gattttatgc ttacttgaat   3660
gttctttgaa tgttcagatg catatcctaa ctggatgctt ctcaaggcct tactgcatat   3720
ttgtgttgca tatttatgtt agttgcacca gggccatttg tagtttgggc aaccgaatgc   3780
cttaattgga aaaaaggcat tgtggtttcc cctatgatct aaattgttac attttaccat   3840
ttcattccga agttggtttt actttattaa atgaagattt agttttcata tcgtatacat   3900
agctgtatag atttcaaaat taggttgtta atttgtgtca cttactattt ttgtgttggt   3960
aatgctttaa atgcatactt aaaaatgaag tactgttatc taagctactg tgtttagaaa   4020
atgttaagaa tgagcagaaa tttttataga aaagtataaa cggaagaaga gataagatac   4080
tgcgaatagg ccctcaaact taaaaaagaa aaaactttgc cagttttaag gacatatttt   4140
gattctttca gtattcttaa caccttttta aacaaagttc ttgatagtac ccactattat   4200
tgggtttgtt ttatgccatt attgattctt gatattcaag catttacaat gtagcatatt   4260
```

```
tgattttctt ttttctttct ttttttggca tcattaacat ttcatttgaa atgcatattg   4320

ttcttgaagt actttgtttt tagcataaat gttgtgcatt ttatcttagt gtttggatga   4380

aaacatttgt gttgtttagc tttcatttgc tttgtatatt taataatgta cctttatttt   4440

ccagtatgcc tacattttgt attgcacaat aaatttattt taagctgaaa aaaaaaaaaa   4500

aaaaaaaaa                                                           4509
```

<210> SEQ ID NO 16
<211> LENGTH: 4974
<212> TYPE: DNA
<213> ORGANISM: Artificial
<220> FEATURE:
<223> OTHER INFORMATION: cDNA coding for mutated mouse KGA

<400> SEQUENCE: 16

```
tgagcgtcag tctcagtgcg gagctcgcgg cggccagagc aacttcggct ggctgcaggc     60

tgggcggcgg cggcggcgag ggcggcggcg ttggcggcgg gagcggcgga gctggggcca    120

caccccgtcc cggacttttt ctctttccag tcctctcccc gccgtgcggg acacggttcc    180

gggagcagag cggccgccca cgccccaagc atcctcatct gacgagcggg cgccggcggt    240

atgatgcggc tgcgaggctc ggcgatgcta cgggagctgc tcttaaggcc gcccgccgcc    300

gtcggagccg tcctgcggcg cgcgcagccc ctcggcacgc tgtgccggcg cccccggggc    360

gggagccggc cgaccgctgg cctggtggcc gctgcgcgac tccacccgtg gtggggcggg    420

ggcggccgcg cgaagggccc cggcgcgggc ggcctgtcca gttcgccctc ggagatccta    480

caggagctgg ggaagggggg tacgccgcca cagcagcagc agcagcagca gcagcagcca    540

ggggcgtcgc cacccgcagc cccgggcccc aaggacagcc cgggggagac cgacgcgttc    600

ggcaacagcg agggcaagga gatggtggcc gcgggcgaca ataaaataaa acagggtctg    660

ttacctagct tggaagattt gctgttctat acaattgcag aaggacaaga aaagatacct    720

gttcacaagt ttattacagc actcaaatct acaggattgc gaacatctga tcccaggttg    780

aaagagtgta tggatatgtt aagattaact cttcagacaa cgtcagatgg tgtcatgcta    840

gacaaagatc tttttaaaaa gtgtgttcaa agcaacattg ttttgttgac acaagcattt    900

agaagaaagt ttgtcattcc tgactttatg tcttttacct cacacatcga tgagttatat    960

gaaagtgcta aaaagcagtc tggagggaag gttgctgatt atattcctca gctggccaaa   1020

ttcagtcctg atttgtgggg tgtatctgtc tgtactgtag atgggcaaag gcattctatt   1080

ggagatacca aagttccttt ttgtcttcag tcctgtgtaa aacccctgaa atatgcaatt   1140

gctgttaatg acctgggaac tgagtatgta catcgctatg ttggggagga gccaagtgga   1200

ttaagattca acaaactctt tttgaatgaa gatgataaac cacataatcc tatggtaaat   1260

gctggagcaa ttgttgtgac ttctctaata aagcaaggag taaataatgc tgagaagttt   1320

gactacgtga tgcaattttt gaataagatg gctggtaatg aatatgttgg attcagtaat   1380

gcaacgtttc agtctgaacg agaaagtgga aagcgaaatt ttgcaatagg atattactta   1440

aaagaaaaga agtgttttcc agaaggcaca gacatggttg ggatactaga tttttacttc   1500

cagctgtgct ctattgaagt gacatgtgaa tcagcaagtg tgatggctgc caccttggct   1560

aatggtggtt tctgcccaat tactggtgaa agagtcctca gtcctgaggc agttgaaaat   1620

acactgagct tgatgcattc ttgtggcatg tatgacttct cagggcagtt tgcgttccat   1680

gttggtcttc ctgcaaaatc tggagttgct gggggtattc ttttagttgt ccccaacgtc   1740

atgggcatga tgtgttggtc tcctcctctt gacaagatgg gcaacagtgt taagggaatt   1800
```

```
cacttttgtc acgatcttgt ttctctgtgt aacttccata actatgataa tttgagacac   1860
tttgcaaaaa aacttgatcc tcggagagaa ggaggtgatc aaagggtgaa gtcggtgata   1920
aaccttctgt ttgccgcata cactggagat gtgtctgccc tccgaaggtt tgctctgtca   1980
gccatggaca tggagcagcg ggattatgac tccagaacag ccctccatgt cgcagcagca   2040
gagggtcatg ttgaagttgt caagtttttg ctggaagctt gcaaagtaaa ccctttcccc   2100
aaggacaggt ggaataatac ccccatggat gaagcactac actttggaca ccatgatgtt   2160
tttaaaatcc ttcaggaata ccaagttcag tacacacctc aaggggattc tgatgatgga   2220
aagggaaacc agactgtcca caagaatctc gacgggttgc tataatggtc tgcaccccaa   2280
gacttccatt acttacctag tcattgtgga acatgactat ggagagcatt gtatatttct   2340
atctggtagt aatgtgtatt tacaacatct gtcactgcag tgttaccgga gcttccttca   2400
ttgtgcgcac acgacaaatc tgagttcttt gggaaaaaaa tagaaatgaa gcagcctccc   2460
ttcataatgt gagcaatagt tacctcgtgc attgtacaat gtggtgtaaa agagtagtta   2520
ccaatgccag ctgaactgtg tggtcttcat ggtttgcgtt ctgtacattt tcaagccctg   2580
gtgatgatac gctcatatgc acttaggagt gagctttgtt gtacagtctg tccacggggt   2640
cgatgctgtt attaggtgaa aatagtgtga tctttaagac tttaaataca gatttagttt   2700
tgagtgtttg agagaccact acacttgtat ggttgagtgt ttaaaatgtc tatcaccctc   2760
acttcagagt gtgactcttt aaatattaaa atagatacta actgttcata gaacaggccg   2820
attctgatta gattttatca gggaatctgt taagatatgt ttggtgacca aaacgtatgt   2880
gtgaatatag ttctagcact tttaaatttt tcctttccat acaacgcttg ggccagcctc   2940
tctgtgctgc gtggctgtcg gtccccctca gctgggaaag agagcactgg ctcactgtgc   3000
agttttcatg tttcctcagc aagccatcaa gcctcacatc tctaccatca gagatagagc   3060
ttggccattt atctaaggaa gatgagccaa aattatgaca tctaaaataa tcgtcagtct   3120
taagagtaaa gacagcgaaa ctgcacactt ataagttctt ttcagcttct acaataaaga   3180
aaagttcaga aatgctttca gttaccaaag ttataacgat atatttagga aaagctacaa   3240
ataacactta ctttgaatcc tgctgtcaaa tgtctgcatc aagatagcac ccctttgtgg   3300
gaggccctga gtatcttctc ttcctctact gcctaactgt tggtgggctg tatcattcaa   3360
taagatcact tcattttcaa cttagaccca ccgtttcttt tttgttgttt tgttttgttt   3420
ggtttggttt ggttgggttg ggttgttgtt tttggttttt tcgagacagg gtttctctgt   3480
gtagccctgg ctgtcctgga actcactttg tagaccaggc tggccttgaa ctcagaaatc   3540
cgcctgcctc tgcctcccga gtgctgggat taaaggtgca aactaccacg cctggcagac   3600
ccaccatttc tttgctttgg aaaggtaatt tatgattaac ttagataata ggtaaaagcg   3660
accttacaaa aaacataatt atctaggagt cccacatact ggacctaccc tattatacct   3720
ccaagagata aagggtatgt tagtgaggac ttttgcacac aagtgcatgc acacttggca   3780
tacacacaca cacacacaca cacacacaca cacacacaca cacacggact tcttggaaac   3840
tgctttatga agaaactgct ttatgaaata agcaaaattc tcaagtgcac agatactagc   3900
agttatgaca gtaatacagc gtcttctgtg accctcacta cctgcactgc ttgcatccct   3960
gctttatgcc tggtggcaca ttattcaccc ggtaacctcc agctgctttg atcctgtttc   4020
agtcaaagtc agcttcagcc accccctcca ttccctagcc agctccaccc ttgatgaaac   4080
tgtggctaat gttccttcac taggacaggc accatgagtg tgtttctaag ttccagagtc   4140
tgtggggagg atggtgggtg ggcagccagc cctgttgcta tgttgcttct tccacacccc   4200
```

```
ctcaagacag gtgcataggt ggcactggga acatcctacg cagggacaac ctccaaaatt   4260
aatgggtgaa catggttttt ttggaatcaa ctgagataat gctatttcaa tagcggctgg   4320
ctttttgtga ttcagtaact taaatattgc cagtgactga ggatcccctc cagtcatggt   4380
tctgtatatt ctttgagaca ggtgttttca tcttctctca gctcagtgct gttttgtaca   4440
gtctctgtgg cttggttgag tatgctcttt cctgtgccag gtcttgctct ggctgttcgc   4500
tactggctga taataacaag gaccctgtgt gtgtgtgaat gagccgctaa ctgctaccat   4560
ctgtaaactc caaagatctg tttgttttgg ctttacaatc ttagctaatt tttctgtatc   4620
ctggaaccat tacatgatca tgttgctttg aagatctttt tatgccactg tttctgctgt   4680
cttggttctg acacccctgt ctggtgatat gctatacccc agtgctgcct acacgtgctt   4740
tagctgtaga gctgggtata ctgttgatcc agctgtccgt cagggacttg ataacctgat   4800
gtttgatgta gatccctgct ggggagtcca caactatgaa tgtatttact tccaacattt   4860
cccaaaatga aaactataaa ttgcaagtat tctggaattg ggaaatactt attttaaatg   4920
agatcaggta gtgttgcttt ttacagcata ataaatatgt gtattgaaaa caaa         4974
```

```
<210> SEQ ID NO 17
<211> LENGTH: 4419
<212> TYPE: DNA
<213> ORGANISM: Artificial
<220> FEATURE:
<223> OTHER INFORMATION: cDNA coding for mutated mouse GAC

<400> SEQUENCE: 17

tgagcgtcag tctcagtgcg gagctcgcgg cggccagagc aacttcggct ggctgcaggc     60
tgggcggcgg cggcggcgag ggcggcggcg ttggcggcgg gagcggcgga gctggggcca    120
caccccgtcc cggacttttt ctctttccag tcctctcccc gccgtgcggg acacggttcc    180
gggagcagag cggccgccca cgccccaagc atcctcatct gacgagcggg cgccggcggt    240
atgatgcggc tgcgaggctc ggcgatgcta cgggagctgc tcttaaggcc gcccgccgcc    300
gtcggagccg tcctgcggcg cgcgcagccc ctcggcacgc tgtgccggcg cccccggggc    360
gggagccggc cgaccgctgg cctggtggcc gctgcgcgac tccacccgtg gtggggcggg    420
ggcggccgcg cgaagggccc cggcgcgggc ggcctgtcca gttcgccctc ggagatccta    480
caggagctgg ggaagggggg tacgccgcca cagcagcagc agcagcagca gcagcagcca    540
ggggcgtcgc cacccgcagc cccgggcccc aaggacagcc cgggggagac cgacgcgttc    600
ggcaacagcg agggcaagga gatggtggcc gcgggcgaca ataaaataaa acagggtctg    660
ttacctagct tggaagattt gctgttctat acaattgcag aaggacaaga aaagatacct    720
gttcacaagt ttattacagc actcaaatct acaggattgc gaacatctga tcccaggttg    780
aaagagtgta tggatatgtt aagattaact cttcagacaa cgtcagatgg tgtcatgcta    840
gacaaagatc tttttaaaaa gtgtgttcaa agcaacattg ttttgttgac acaagcattt    900
agaagaaagt ttgtcattcc tgactttatg tcttttacct cacacatcga tgagttatat    960
gaaagtgcta aaaagcagtc tggagggaag gttgctgatt atattcctca gctggccaaa   1020
ttcagtcctg atttgtgggg tgtatctgtc tgtactgtag atgggcaaag gcattctatt   1080
ggagatacca aagttccttt ttgtcttcag tcctgtgtaa aaccccctgaa atatgcaatt   1140
gctgttaatg acctgggaac tgagtatgta catcgctatg ttggggagga gccaagtgga   1200
ttaagattca acaaactctt tttgaatgaa gatgataaac cacataatcc tatggtaaat   1260
gctggagcaa ttgttgtgac ttctctaata aagcaaggag taaataatgc tgagaagttt   1320
```

-continued

```
gactacgtga tgcaattttt gaataagatg gctggtaatg aatatgttgg attcagtaat   1380
gcaacgtttc agtctgaacg agaaagtgga aagcgaaatt ttgcaatagg atattactta   1440
aaagaaaaga agtgttttcc agaaggcaca gacatggttg ggatactaga tttttacttc   1500
cagctgtgct ctattgaagt gacatgtgaa tcagcaagtg tgatggctgc caccttggct   1560
aatggtggtt tctgcccaat tactggtgaa agagtcctca gtcctgaggc agttgaaaat   1620
acactgagct tgatgcattc ttgtggcatg tatgacttct cagggcagtt tgcgttccat   1680
gttggtcttc ctgcaaaatc tggagttgct gggggtattc ttttagttgt ccccaacgtc   1740
atgggcatga tgtgttggtc tcctcctctt gacaagatgg gcaacagtgt taagggaatt   1800
cacttttgtc acgatcttgt ttctctgtgt aacttccata actatgataa tttgagacac   1860
tttgcaaaaa aacttgatcc tcggagagaa ggaggtgatc aaaggcattc ctttggacca   1920
ttggactatg agagtctcca gcaagaactt gctttaaaag acacagtatg gaaaaaagtg   1980
tcacctgagt caagtgacga cacctctaca actgtagtat atagaatgga gagtctgggg   2040
gagaggagct agagatgggc tctagctaca gaacagaacg attctccttt taacatcgga   2100
aacatcttta ggcttttgtt tcttgtttat ctttccaaac taagtattta ttcaagtatt   2160
ctattgttat cagttttggg tactggagcc ataaatttaa aaaaaggttc tgttttggtt   2220
tggttttttt tcgcttgtaa tctttgtata aaaaacattt gttatttttt aaaagagcat   2280
ttacaaataa agcaaatttg ctttattttt taaaactttt ttaaaaaatg caatttcctt   2340
aattacatta aaaatttaac tataaaattt ggtaaccaca ttgtttttct tagttctgaa   2400
gcctgcatat taaactgagg cgtattgttg gatttgtctt ttcctttcca gttttataat   2460
tgataggcta tattggtagt gacagaaagt acttccatgc taaatataaa actaaaaagg   2520
caaagtaatc aaaattattt aaaagagtac tagattataa aattagcttt agtttacaca   2580
tatgccagtt atagcggtag attggctttg aatatttaaa atgcaaatac ttttaaatat   2640
gtcttttttt ttgtttgaaa agttctgtcc tgtcagaatc acaatgtatt aggaatgttt   2700
cacatcactg aaacactcca gccaaagaat tgcagatgtg tgagaatggc atgccctgtt   2760
atttaaaagc tacaatggtt agttgctcag aaaaagagtc aataactatc ttcaaaatgg   2820
attgtatttt catattcttc atgtaatttt tttgttgtat ttaagtatga acggtaaatt   2880
ttgctttttt agcttttagt aattttatta tgtttcataa gtgctaatga atattttgtg   2940
ataattataa catctcataa attttgttct ttttgaactt ttattagcat acttatgaaa   3000
tgaatatagt ttgaaggtgt taagtataca actaaaatat ttgttgaatt ggaatgcttc   3060
tgtttatttt taaaatgcaa tattgagaat caaaactttt ttcaagagaa tcataggttc   3120
cattttatct cgtcataaac agatatacat atttttagaa tctatcttgg caaaatgata   3180
ctaatgttct gcaggattta tttacatgtc ttccttcgtg tattttgttt ttctcacaat   3240
ttcaagtttg gtttttcaaa ttcactttta aacttgtaaa ttttgggcaa gtggttgaga   3300
atgaaagcct tattgctttt taaattatgg cacatgtata gtagagcaga ttctgtaact   3360
aaagaaagtg cgggaaaaat agttcactga taggctaagt aagatacagg aaagtcctga   3420
tggtctgatt tgaaactggg aactctgata ttaagaaaag ggttcttctc agaagttcga   3480
ccttaaagcc tttgggctaa cttaagtatt actatttgta tttaaataat tacatggtgg   3540
gttttagaaa ggctggctgt cctgcccctt tggtgttcat atgcattccc cagcctgatg   3600
ctttaaaagc cttgccactg ccctgcttgt ggacactaat catctctttt tcttgtatcc   3660
agagtgactg tgattcaggt aattgagcac catgattgga aaaaagattt taggtttatt   3720
```

```
tcccctccat ttttatgtgt acattttgtt gtttcattca gaagttggat ttactttaca   3780

aaatgactta attttcatat tgtggtcatg tttgtgtaaa cttcaaacta ttttgttaat   3840

ttttggcact tcctatatat aattctagta atgcttgaat gtacacttaa atatgaagta   3900

ggattaagtc agctgctgtg tttaaagaat gctgttaaga acaagcattc aaaactgtat   3960

aggaaggtat tagcttaaga gtaggtaaga taccgtgact gtatctgcag acaagaagag   4020

gaaagaaaag ctttgccagt ttgtggattt atcttaattc ccttcagtat attcaatctc   4080

ttttcaaata aagctctttg agaagtaccc agtattgttg ggtttaattt ttcctactat   4140

tattgattct tgatattcaa gcatttacat gacagcgtat ttttttcttt tccttttttc   4200

tgtttatttt tttttgctat cattaacatt tcatttgaaa tgcatactct tcttgaaata   4260

ttttgttttt agcataaatg ttgtgcattt tatcttagtg tttggattaa aacatttgtg   4320

ttgttgagct ttcttcattt gctttgtata tttaataatg tatctttatt ttccagtatg   4380

cctatttttt gtattgtaca ataaatttat tttaagctg                          4419
```

<210> SEQ ID NO 18
<211> LENGTH: 287
<212> TYPE: PRT
<213> ORGANISM: Artificial
<220> FEATURE:
<223> OTHER INFORMATION: pfam04960 domain
<220> FEATURE:
<221> NAME/KEY: MISC_FEATURE
<222> LOCATION: (32)..(32)
<223> OTHER INFORMATION: X is either I or T

<400> SEQUENCE: 18

```
Gly Lys Val Ala Asp Tyr Ile Pro Gln Leu Ala Lys Phe Ser Pro Asp
1               5                   10                  15

Leu Trp Gly Val Ser Val Cys Thr Val Asp Gly Gln Arg His Ser Xaa
            20                  25                  30

Gly Asp Thr Lys Val Pro Phe Cys Leu Gln Ser Cys Val Lys Pro Leu
        35                  40                  45

Lys Tyr Ala Ile Ala Val Asn Asp Leu Gly Thr Glu Tyr Val His Arg
    50                  55                  60

Tyr Val Gly Lys Glu Pro Ser Gly Leu Arg Phe Asn Lys Leu Phe Leu
65                  70                  75                  80

Asn Glu Asp Asp Lys Pro His Asn Pro Met Val Asn Ala Gly Ala Ile
                85                  90                  95

Val Val Thr Ser Leu Ile Lys Gln Gly Val Asn Asn Ala Glu Lys Phe
            100                 105                 110

Asp Tyr Val Met Gln Phe Leu Asn Lys Met Ala Gly Asn Glu Tyr Val
        115                 120                 125

Gly Phe Ser Asn Ala Thr Phe Gln Ser Glu Arg Glu Ser Gly Asp Arg
    130                 135                 140

Asn Phe Ala Ile Gly Tyr Tyr Leu Lys Glu Lys Lys Cys Phe Pro Glu
145                 150                 155                 160

Gly Thr Asp Met Val Gly Ile Leu Asp Phe Tyr Phe Gln Leu Cys Ser
                165                 170                 175

Ile Glu Val Thr Cys Glu Ser Ala Ser Val Met Ala Ala Thr Leu Ala
            180                 185                 190

Asn Gly Gly Phe Cys Pro Ile Thr Gly Glu Arg Val Leu Ser Pro Glu
        195                 200                 205

Ala Val Arg Asn Thr Leu Ser Leu Met His Ser Cys Gly Met Tyr Asp
    210                 215                 220
```

```
Phe Ser Gly Gln Phe Ala Phe His Val Gly Leu Pro Ala Lys Ser Gly
225                 230                 235                 240

Val Ala Gly Gly Ile Leu Leu Val Val Pro Asn Val Met Gly Met Met
                245                 250                 255

Cys Trp Ser Pro Pro Leu Asp Lys Met Gly Asn Ser Val Lys Gly Ile
            260                 265                 270

His Phe Cys His Asp Leu Val Ser Leu Cys Asn Phe His Asn Tyr
        275                 280                 285


<210> SEQ ID NO 19
<211> LENGTH: 287
<212> TYPE: PRT
<213> ORGANISM: Artificial
<220> FEATURE:
<223> OTHER INFORMATION: Mutated glutaminase domain pfam4960
<220> FEATURE:
<221> NAME/KEY: misc_feature
<222> LOCATION: (32)..(32)
<223> OTHER INFORMATION: Xaa can be any naturally occurring amino acid

<400> SEQUENCE: 19

Gly Lys Val Ala Asp Tyr Ile Pro Gln Leu Ala Lys Phe Ser Pro Asp
1               5                   10                  15

Leu Trp Gly Val Ser Val Cys Thr Val Asp Gly Gln Arg His Ser Xaa
            20                  25                  30

Gly Asp Thr Lys Val Pro Phe Cys Leu Gln Ser Cys Val Lys Pro Leu
        35                  40                  45

Lys Tyr Ala Ile Ala Val Asn Asp Leu Gly Thr Glu Tyr Val His Arg
    50                  55                  60

Tyr Val Gly Glu Glu Pro Ser Gly Leu Arg Phe Asn Lys Leu Phe Leu
65                  70                  75                  80

Asn Glu Asp Asp Lys Pro His Asn Pro Met Val Asn Ala Gly Ala Ile
                85                  90                  95

Val Val Thr Ser Leu Ile Lys Gln Gly Val Asn Asn Ala Glu Lys Phe
            100                 105                 110

Asp Tyr Val Met Gln Phe Leu Asn Lys Met Ala Gly Asn Glu Tyr Val
        115                 120                 125

Gly Phe Ser Asn Ala Thr Phe Gln Ser Glu Arg Glu Ser Gly Lys Arg
    130                 135                 140

Asn Phe Ala Ile Gly Tyr Tyr Leu Lys Glu Lys Lys Cys Phe Pro Glu
145                 150                 155                 160

Gly Thr Asp Met Val Gly Ile Leu Asp Phe Tyr Phe Gln Leu Cys Ser
                165                 170                 175

Ile Glu Val Thr Cys Glu Ser Ala Ser Val Met Ala Ala Thr Leu Ala
            180                 185                 190

Asn Gly Gly Phe Cys Pro Ile Thr Gly Glu Arg Val Leu Ser Pro Glu
        195                 200                 205

Ala Val Glu Asn Thr Leu Ser Leu Met His Ser Cys Gly Met Tyr Asp
    210                 215                 220

Phe Ser Gly Gln Phe Ala Phe His Val Gly Leu Pro Ala Lys Ser Gly
225                 230                 235                 240

Val Ala Gly Gly Ile Leu Leu Val Val Pro Asn Val Met Gly Met Met
                245                 250                 255
```

-continued

```
Cys Trp Ser Pro Pro Leu Asp Lys Met Gly Asn Ser Val Lys Gly Ile
            260                 265                 270

His Phe Cys His Asp Leu Val Ser Leu Cys Asn Phe His Asn Tyr
        275                 280                 285
```